US008815328B2

(12) United States Patent
Riman et al.

(10) Patent No.: US 8,815,328 B2
(45) Date of Patent: Aug. 26, 2014

(54) HYDROXYAPATITE WITH CONTROLLABLE SIZE AND MORPHOLOGY

(75) Inventors: Richard E. Riman, Belle Mead, NJ (US); Alexander Burukhin, Moscow (RU); Eugene Zlotnikov, Highland Park, NJ (US); Dan Haders, Weehawken, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/504,143

(22) PCT Filed: Oct. 26, 2010

(86) PCT No.: PCT/US2010/054146
§ 371 (c)(1),
(2), (4) Date: Dec. 10, 2012

(87) PCT Pub. No.: WO2011/053598
PCT Pub. Date: May 5, 2011

(65) Prior Publication Data
US 2013/0078476 A1    Mar. 28, 2013

Related U.S. Application Data

(63) Continuation-in-part of application No. 11/813,368, filed as application No. PCT/US2005/046209 on Dec. 21, 2005, now Pat. No. 7,998,219.

(60) Provisional application No. 61/255,061, filed on Oct. 26, 2009, provisional application No. 60/641,083, filed on Jan. 4, 2005.

(51) Int. Cl.
*B05D 3/02* (2006.01)
*A61F 2/28* (2006.01)
(Continued)

(52) U.S. Cl.
CPC . *B05D 1/18* (2013.01); *A61L 27/06* (2013.01); *A61L 27/12* (2013.01); *A61L 27/32* (2013.01); *B01J 20/048* (2013.01); *B01J 20/286* (2013.01); *B01J 20/3204* (2013.01); *B01J 20/3236* (2013.01); *B01J 27/1806* (2013.01); *B01J 37/0225* (2013.01); *C01B 25/32* (2013.01); *C04B 28/34* (2013.01); *C23C 22/62* (2013.01); *C23C 22/64* (2013.01); *A61F 2/02* (2013.01)
USPC ........ 427/2.27; 427/2.1; 427/430.1; 427/379; 623/23.57; 623/23.6

(58) Field of Classification Search
CPC ........ A61F 2/30767; A61L 27/32; B05D 1/18
USPC ................ 427/2.27, 379, 430.1; 623/23.57, 6
See application file for complete search history.

(56) References Cited

U.S. PATENT DOCUMENTS 4,097,935 A   7/1978  Jarcho
4,335,086 A   6/1982  Spencer
(Continued)

FOREIGN PATENT DOCUMENTS

JP    06245992 A    9/1994
WO    9717285 A1    5/1997
(Continued)

OTHER PUBLICATIONS

Kim et al. Hydroxyapatite coating on titanium substrate with titania buffer layer processed by sol-gel method. Biomaterials vol. 25, Issue 13, Jun. 2004, pp. 2533-2538.*

(Continued)

*Primary Examiner* — Cachet Sellman
(74) *Attorney, Agent, or Firm* — Fox Rothschild LLP

(57) ABSTRACT

Methods are presented for a continuous, two-step, phase sequenced deposition of hydroxyapatite film over the surface of the substrate.

28 Claims, 39 Drawing Sheets

(51) Int. Cl.

| | |
|---|---|
| A61L 27/32 | (2006.01) |
| B05D 1/18 | (2006.01) |
| A61L 27/06 | (2006.01) |
| A61L 27/12 | (2006.01) |
| B01J 20/04 | (2006.01) |
| B01J 20/286 | (2006.01) |
| B01J 20/32 | (2006.01) |
| B01J 27/18 | (2006.01) |
| B01J 37/02 | (2006.01) |
| C01B 25/32 | (2006.01) |
| C04B 28/34 | (2006.01) |
| C23C 22/62 | (2006.01) |
| C23C 22/64 | (2006.01) |
| A61F 2/02 | (2006.01) |

(56) References Cited

U.S. PATENT DOCUMENTS

| | | | |
|---|---|---|---|
| 4,429,691 | A | 2/1984 | Niwa et al. |
| 4,794,023 | A | 12/1988 | Shimamune et al. |
| 4,871,578 | A | 10/1989 | Adam et al. |
| 4,874,511 | A | 10/1989 | Kawasaki et al. |
| 4,960,646 | A | 10/1990 | Shimamune et al. |
| 5,073,410 | A | 12/1991 | Paz-Pujalt |
| 5,082,566 | A | 1/1992 | Tagaya et al. |
| 5,108,956 | A | 4/1992 | Inoue et al. |
| 5,128,146 | A | 7/1992 | Hirayama et al. |
| 5,128,169 | A | 7/1992 | Saita et al. |
| 5,164,187 | A | 11/1992 | Constantz et al. |
| 5,205,928 | A | 4/1993 | Inoue et al. |
| 5,227,147 | A | 7/1993 | Yoshimura et al. |
| 5,279,831 | A | 1/1994 | Constantz et al. |
| 5,405,436 | A | 4/1995 | Maurer et al. |
| 5,427,754 | A | 6/1995 | Nagata et al. |
| 5,472,734 | A | 12/1995 | Perrotta et al. |
| 5,609,633 | A | 3/1997 | Kokubo |
| 5,652,056 | A | 7/1997 | Pepin |
| 5,676,997 | A * | 10/1997 | Okuyama et al. ............ 427/2.26 |
| 5,723,038 | A | 3/1998 | Scharnweber et al. |
| 5,766,618 | A | 6/1998 | Laurencin et al. |
| 5,830,480 | A | 11/1998 | Ducheyne et al. |
| 5,858,318 | A | 1/1999 | Luo |
| 5,922,025 | A | 7/1999 | Hubbard |
| 6,013,591 | A | 1/2000 | Ying et al. |
| 6,027,742 | A | 2/2000 | Lee et al. |
| 6,153,266 | A | 11/2000 | Yokogawa et al. |
| 6,344,061 | B1 | 2/2002 | Leitao et al. |
| 6,358,532 | B2 | 3/2002 | Starling et al. |
| 6,426,114 | B1 | 7/2002 | Troczynski et al. |
| 6,569,489 | B1 | 5/2003 | Li |
| 6,720,023 | B1 | 4/2004 | Kim et al. |
| 6,777,214 | B1 | 8/2004 | Yamashita |
| 7,008,450 | B2 | 3/2006 | Kim et al. |
| 7,247,288 | B2 | 7/2007 | Kumta et al. |
| 7,390,335 | B2 | 6/2008 | Chow |
| 7,527,687 | B2 | 5/2009 | Genge et al. |
| 7,767,250 | B2 * | 8/2010 | Luan et al. ...................... 427/2.1 |
| 7,879,388 | B2 * | 2/2011 | Clarkson et al. ............ 427/2.27 |
| 7,998,219 | B2 | 8/2011 | Riman et al. |
| 2003/0219466 | A1 | 11/2003 | Kumta et al. |
| 2004/0034141 | A1 | 2/2004 | Aramaki et al. |
| 2005/0196620 | A1 | 9/2005 | Watanabe et al. |
| 2005/0226939 | A1 | 10/2005 | Ramalingam et al. |
| 2006/0062925 | A1 | 3/2006 | Rohanizadeh et al. |
| 2007/0184299 | A1 | 8/2007 | Wei et al. |
| 2008/0206443 | A1 | 8/2008 | Schwartz et al. |
| 2008/0206554 | A1 * | 8/2008 | Riman et al. .................. 428/330 |
| 2008/0220148 | A1 | 9/2008 | Clarkson et al. |

FOREIGN PATENT DOCUMENTS

| | | |
|---|---|---|
| WO | 9932400 A1 | 7/1999 |
| WO | 0003747 A2 | 1/2000 |
| WO | 03000588 A1 | 1/2003 |

OTHER PUBLICATIONS

Haders et al. Phase-Sequenced Deposition of Calcium Titanate/Hydroxyapatite Films with Controllable Crystallographic Texture onto Ti6Al4V by Triethyl Phosphate-Regulated Hydrothermal Crystallization. Crystal Growth and Design. 2009, vol. 9, No. 8 pp. 3412-3422.*

Fujishiro et al. Coating of CaTiO3 on titanium substrates by hydrothermal reactions using calcium-ethylene diamine tetra acetic acid chelate. Journal of Materials Science. Materials in Medicine. vol. 9. (1998) pp. 363-367.*

Varma, HK., et al., "Polymeric precursor route for the preparation of calcium phosphate compounds", Ceramics International. 24(6) (Dec. 31, 1998), p. 467-470.

Haders, D., et al., "TED/EDPA Doubly Regulated Hydrothermal Crystallization of Hydroxyapatite Films on Metal Substrates", Chemistry of Materials, 2008, 20(22), 7177-7187.

Haders, D., et al., "Phase-Sequenced Deposition of Calcium Tinanate/Hydroxyapatite Filims with Controllable Crystallographic Texture onto Ti6Al4V by Triethly Phosphate-Regulated Hydrothermal Crystallization", Crystal Growth & Design, 2009, 9(8), 3412-3422.

Lencka, M., et al., "Thermodynamic Modeling of Hydrothermal Synthesis of Cermaic Powers", Chemistry of Materials 1993(5), 61-70.

Riman, RE., et al. "Solution synthesis of hydroxyapatite designer particulates", Solid State Ionics, Diffusion & Reactions 2002, 151(1-4), 393-402.

Fujishiro, Y.; "Coating of Hydroxyapatite on Titanium Plates Using Thermal Dissociation of Calcium-EDTA Chelate Comples in Phosphate Solutions under Hydrotermal Conditions", Journal of Colloid and Interface Science 1995, 173 (1), 119-127.

Bertoni et al., "Nanocrystals of magnesium and fluoride susbtituted hydroxyapatite", J. Inorg. Biochem., 72 (1):29-35 (1998).

Bigi et al., "Magnesium Influence on hydroxypatite crystalization", J. Inorg. Biochem. 49, 69-78 (1993).

Patel, P.N., "Magnesium Calcium Hydroxylapatite Solid Solutions", J. Inorg. Nucl. Chem, vol. 42, pp. 1129-1132 (1980).

Yasukawa, A. et al., "Preparation and characterization of magnesium-calcium hydroxyapatites", J. Mater. Chem, vol. 6, No. 8, pp. 1401-1405 (1996).

Liao, J. et al., "Synthesis of Ca-Mg Apatite via a Mechanochemical Hydrothermal Process", J. Mater. Synth. Process, vol. 8, No. 5/6, pp. 305-311 (2000).

Yokogawa, Y. et al., "Synthesis of Calcium-Strontium, Calcium-Magnesium, Magnesium-Strontium Apatite Through Mechanochemical Method", Report of National Industrial Research Institute of Nagoya, vol. 45, No. 4, pp. 161-166 (1996).

Riman, R., "Solution synthesis of hydroxyapatite designer particulates," Solid State Ionics 151 (2002); pp. 393-402.

Lopatin et al., "Ion-beam densification of hydroxyapatite thin films," Nucl. Instr. and Meth. in Phys. Res. B 145 (1998); pp. 522-531.

Kothapalli et al., "Influence of temperature and concentration on the sintering behavior and mechanical properties of hydroxyapatite," Acta Materialia 52 (2004); pp. 5655-5663.

Furukawa et al., "Biodegradation behavior of ultra-high-strength hydroxyapatite/poly (L-lactide) composite rods for internal fixation of bone fractures," Biomaterials 21 (2000); pp. 889-898.

Furuzono et al., "Nano-scaled hydroxyapatite/polymer compostie IV. fabrication and cell adhesion properties of a three-dimensional scaffold made of composite material with a silk fibroin substrate to develop a percutaneous devices," J Artif Organs(2004) 7: pp. 137-144.

European Search Report issued for EP Application No. 05854856.1.

* cited by examiner

| Morphological Type of Hydroxyapatite | Crystals Length (diameter) microns | Aspect ratio |
|---|---|---|
| Hexagonal rods | 3-5 | 5 |
| Hexagonal rods | ~30 | 4-5 |
| Barrels | 1-2 | ~2 |
| Tubular | 3-5 | 3 |
| Spheres | 0.5-1 | 1 |
| Platelets | 1-2 | 0.7 |

FIG. 1

| # | Calcium Nitrate m | Tri-ethyl Phosphate m | Ethylendiamine tetracetic acid m | Ammonia m | Potassium Hydroxide m | Time h | Temperature °C | Rotation speed (rpm) |
|---|---|---|---|---|---|---|---|---|
| 1 | 0.5 | 0.2015 | 0.5 | 0 | 2 | 24 | 200 | 0 |
| 2 | 0.05 | 0.02015 | 0.025 | 20 | 0.2 | 25 | 200 | 0 |
| 3 | 0.5 | 0.2015 | 0 | 0 | 2 | 24 | 200 | 300 |
| 4 | 0.5 | 0.25 | 0 | 2 | 0 | 24 | 200 | 200 |
| 5 | 0.5 | 0.2015 | 0 | 2 | 0 | 24 | 200 | 1200 |
| 6 | 0.5 | 0.2015 | 0 | 0 | 2 | 24 | 180 | 0 |
| 7 | 0.15 | 0.07 | 0.15 | 0 | 0.7 | 20 | 180 | 0 |

FIG. 2

| # | Calcium Nitrate m | Tri-ethyl Phosphate m | Ethylendiamine tetracetic acid m | Ammonia m | Potassium Hydroxide m | Time h | Temperature °C | Rotation speed | Substrate |
|---|---|---|---|---|---|---|---|---|---|
| 7 | 0.25 | 0.2015 | 0.25 | 0 | 2 | 24 | 200 | 0 | Ti-foil 0.127 mm (Aldrich) |
| 8 | 0.25 | 0.2015 | 0.25 | 0 | 2 | 24 | 200 | 0 | Stainless Steel 304 |
| 9 | 0.25 | 0.2015 | 0.25 | 0 | 2 | 24 | 200 | 0 | Sapphire |
| 10 | 0.25 | 0.2015 | 0.25 | 0 | 2 | 24 | 184 | 0 | Yttria |
| 11 | 0.25 | 0.2015 | 0.25 | 0 | 2 | 24 | 200 | 0 | Teflon |
| 12 | 0.25 | 0.2015 | 0.25 | 0 | 2 | 24 | 200 | 0 | Titanium sponge (McMaster) |
| 13* | | | 0.25 | 0 | 2 | 18.5 | 200 | 0 | Stainless Steel 316 |
| 14* | | | 0.25 | 0 | 2 | 27 | 200 | 0 | Titanium alloy Ti 4Al-4V F136 |
| 15* | | | 0.25 | 0 | 2 | 27 | 200 | 0 | Titanium Alloy Ti 4Al-4V F136 B348 |
| 16* | | | 0.25 | 0 | 2 | 18 | 200 | 0 | Cobalt Chrome Alloy F75 |
| 17 | 0.25 | 0.2 | 0 | 2 | 0 | 6 | 180 | 200 | Titanium wire (McMaster) diameter 0.25 mm |

FIG. 3

| Temperature °C | Time Hours | EDTA g | Ca(NO₃)₂*4 H₂O g | TEP g | KOH | Water | Aspect Ratio | Length microns |
|---|---|---|---|---|---|---|---|---|
| 200 | 20 | 4.38 | 3.54 | 2.20 | 6.72 | 43.15 | 1.33 | 2.23 |
| 200 | 20 | 1.58 | 2.13 | 1.32 | 4.03 | 50.94 | 1.70 | 10.22 |
| 200 | 40 | 4.38 | 3.54 | 2.20 | 6.72 | 43.15 | 2.05 | 18.17 |
| 200 | 40 | 1.58 | 2.13 | 1.32 | 4.03 | 50.94 | 1.84 | 13.94 |
| 180 | 20 | 4.38 | 3.54 | 2.20 | 6.72 | 43.15 | 0.74 | 2.88 |
| 180 | 20 | 1.58 | 2.13 | 1.32 | 4.03 | 50.94 | 0.58 | 1.53 |
| 180 | 40 | 4.38 | 3.54 | 2.20 | 6.72 | 43.15 | 1.04 | 5.26 |
| 180 | 40 | 1.58 | 2.13 | 1.32 | 4.03 | 50.94 | 1.56 | 7.66 |

| Substrate | Roughness, Ra (nm) | Identified Phase(s) | Ti - (0002)/(10-11) | Austenite - (200)/(111) | Co - (0002)/(10-11) |
|---|---|---|---|---|---|
| Ti6Al4V | 414 | Ti | 1.19 | - | - |
| Ti | 1172 | Ti | 2.16 | - | - |
| Rough- Ti6Al4V | 3569 | Ti, Corundum | 0.36 | - | - |
| Stainless Steel | 531 | Austenite | - | 0.05 | - |
| Co28Cr6Mo | 678 | Co | - | - | 3.24 |
| PDF 44-1294 | - | Ti | 0.3 | - | - |
| PDF 33-0397 | - | Austenite | - | 0.45 | - |
| PDF 05-0727 | - | Co | - | - | 0.6 |

| Substrate | HA Crystallinity (%) | (0002)/(21-31) | Avg Particle Diameter (μm) | Thickness (μm) | Adhesion Rating |
|---|---|---|---|---|---|
| Ti6Al4V | 99 | 15.26 | 12 +/- 4 | 22 +/- 8 | 5A |
| Ti | 99 | 14.51 | 12 +/- 4 | 13 +/- 3 | 5A |
| Rough-Ti6Al4V | 99 | 4.04 | 11 +/- 2 | 18 +/- 4 | 5A |
| Stainless Steel | 99 | 0.66 | 8 +/- 5 | 16 +/- 7 | 4A |
| Co28Cr6Mo | 99 | >>100 | 8 +/- 5 | 12 +/- 7 | 3A |

HYDROXYAPATITE WITH CONTROLLABLE SIZE AND MORPHOLOGY

CROSS-REFERENCE TO RELATED APPLICATIONS

The instant application is the U.S. National Phase of International Patent Application Serial No. PCT/US10/54146, filed Oct. 26, 2010, which claims 35 U.S.C. §119(e) priority to U.S. Provisional Patent Application Ser. No. 61/255,061 filed Oct. 26, 2009. International Patent Application Serial No. PCT/US10/54146 is also a continuation-in-part under 35 U.S.C. §120 to U.S. patent application Ser. No. 11/813,368 filed Jul. 5, 2007, which is the U.S. National Stage entry of International Patent Application Serial No. PCT/US05/46209 filed Dec. 21, 2005, which in turn claims priority under 35 U.S.C. §119(e) to U.S. Provisional Patent Application Ser. No. 60/641,083 filed on Jan. 4, 2005. The foregoing applications are incorporated herein by reference in their entireties.

BACKGROUND OF THE INVENTION

Hydroxyapatite (HAp, chemical formula $Ca_{10}(PO_4)_6(OH)_2$) has attracted the attention of researchers over the past thirty years as an implant material because of its excellent biocompatibility and bioactivity. HAp has been extensively used in medicine for implant fabrication. It is commonly the material of choice for the fabrication of dense and porous bioceramics. Its general uses include biocompatible phase-reinforcement in composites, coatings on metal implants and granular fill for direct incorporation into human tissue. It has also been extensively investigated for non-medical applications such as a packing material/support for column chromatography, gas sensors and catalysts, as a host material for lasers, and as a plant growth substrate.

Previously explored methods of hydroxyapatite synthesis for particles include conventional solid-state reactions, sol-gel, phase transformation, hydrothermal, chemical precipitation, and precipitation in simulated body fluid. Solid-state reactions utilize high temperature processes (600-1250° C.) using powders of compounds such as tricalcium phosphate and calcium hydroxide. The product of the high temperature reaction is communited to a powder of a desired size range. However, materials made with this approach do not have controlled morphology. Further, they have broad size distributions and wear of the milling media and container introduces impurities. Sol-gel reactions require a sintering step to obtain crystalline product, which is not always phase-pure. A similar downfall is seen with phase transformation—the product is rarely phase-pure and does not have controllable size or morphology. Aqueous precipitation methods have been widely used, but generally either produce fiber morphologies or large agglomerates of nanostructured particles with no well-defined morphology. Simulated body fluid syntheses have not been demonstrated to make particles with controlled size and morphology and have a very low process yields, making them impractical for manufacturing.

Various morphological types of hydroxyapatite have been disclosed in patent literature. For example, U.S. Pat. No. 5,227,147 claims the production of whiskers i.e. fibers with aspect ratio above 10 for biomedical applications. The length of the whiskers according to this invention varies from 1 to 1000 microns.

A hydrothermal process for the preparation of plate-like hexagonal hydroxyapatite particles in the presence of water-miscible organic solvents is described in U.S. Pat. No. 5,427,754. The size (maximum diameter) of hydroxyapatite platelets obtained according to this invention generally falls between 50 and 200 nm.

U.S. Pat. No. 6,358,532 reveals a sol-gel method of microbead formation. The microbeads have a diameter of 0.1-6 mm and a wall thickness from 20 to 230 microns.

U.S. Pat. No. 4,335,086 describes the preparation of hydroxyapatite by heating an aqueous suspension of brushite to prepare rosette-shaped crystals. These crystals are between 40 and 70 microns in size.

Further, there are numerous patents related to production and application of spherical hydroxyapatite particles. For example, U.S. Pat. No. 5,082,566 describes a calcium-phosphate type hydroxyapatite from 0.5 to 50 microns in diameter. Hydroxyapatite is produced by spray-drying a gel or slurry form of an aqueous calcium phosphate solution into a high-temperature air stream ranging from 100-200° C. This instantaneously dries the granular apatite, which is then fired at 400-700° C.

U.S. Pat. Nos. 5,108,956 and 5,205,928 describe processes for preparing sintered microspherical hydroxyapatite particles by spray-firing a suspension of hydroxyapatite dispersed in an inflammable solvent.

The application of spherical hydroxyapatite particles of 10-100 microns in diameter as a filler for biodegradable polymers (U.S. Pat. No. 5,766,618) or an ingredient of an injectable composition (U.S. Pat. No. 5,922,025) have been speculated, but with no specific details on the production of the particles available.

Spherical hydroxyapatite aggregates (1-10 microns) built of about 0.1 micron crystals are described in U.S. Pat. No. 4,874,511 as an adsorbent for chromatograph columns. 5 mm long hydroxyapatite filaments with diameter not greater than 5 microns are disclosed in U.S. Pat. No. 5,652,056.

Spherical hydroxyapatite crystals are described in U.S. Pat. No. 6,013,591. The particles of 20-150 nm in size were sintered by pressurizing and calcination. Hollow spheres and doughnuts are disclosed in U.S. Pat. No. 5,858,318 with sizes from 1 to 8 microns.

Coatings of hydroxyapatite find use in many applications, such as, for example, biomedical devices (prosthesis, implants), protection of metal surfaces against corrosion, aggressive chemicals and environment, and strengthening of the various surfaces. The properties of hydroxyapatite depend, to a great extent, on the size and shape of the particles. Therefore, the morphology of the particles is extremely important for production of high quality coatings. However, numerous patents related to coatings are not directed to the morphology and size of hydroxyapatite particles.

U.S. Pat. No. 6,426,114 discloses a ceramic coating with a thickness of 1-5 microns made by a sol-gel method at relatively low temperature (350° C.).

U.S. Pat. No. 4,871,578 discloses the hydroxyapatite coating of metal and ceramic surfaces made by coating a substrate with tri-calcium phosphate and the subsequent transformation of this phase into hydroxyapatite by interaction with water at elevated temperature.

U.S. Pat. Nos. 4,794,023 and 4,960,646 disclose the coating of a metal substrate (titanium, titanium alloys, and stainless steel) by treatment with a nitric acid solution containing dissolved hydroxyapatite. After drying, the substrate undergoes fire treatment at 300° C., which turns the coating into hydroxyapatite. An essentially similar method is disclosed in U.S. Pat. No. 5,128,169. This patent recites metal, ceramic, and glass as possible substrates. Particles of hydroxyapatite constituting a coating have ranges from 0.1 to 1 micron.

U.S. Pat. No. 5,128,146 discloses the plasma spray coating of titanium and ceramic substrates with hydroxyapatite particles of 10 to 30 microns in diameter.

U.S. Pat. Nos. 5,164,187 and 5,279,831 disclose the solution treatment of a metal substrate that coats it with a multi-layered film of hydroxyapatite made of whiskers 1-40 microns long and 0.01-20 microns in diameter. In order to control the size of hydroxyapatite crystals, these patents change the concentration of the precursor.

U.S. Pat. No. 5,609,633 recites a hydroxyapatite coating of titanium or titanium alloys in an alkaline media comprising an inner layer of amorphous titanate and an outer layer of crystalline hydroxyapatite. The thickness of the layers varies from 0.1 to 10 microns for the inner layer and above 1 micron for the outer layer.

U.S. Pat. No. 5,676,997 discloses the coating process with a precursor having salts with phosphoric acid and calcium in the presence of chelating agents, in particular, ethylenediaminetetraacetic acid with no specification of the hydroxyapatite morphology produced.

U.S. Pat. No. 5,676,997 discloses the use of ethylendiaminetetracetic acid and other chelating agents to control the synthesis of hydroxyapatite on metal substrates. According to this patent the synthesis/coating process includes the preparation of a homogeneous precursor, submerging the substrate into the precursor, and drying the precursor solution on the substrate. Thus, this method totally excludes the possibility of homogeneous nucleation of hydroxyapatite.

Degradable components as a source of phosphate are described in U.S. Pat. No. 6,426,114. The patent discloses the use of hydrolysable tri-ethyl phosphite in a sol-gel process and includes a calcination step. Another disadvantage of this method is the immiscibility of tri-ethyl phosphite with water, even in presence of organic solvents such as ethyl alcohol.

The use of water miscible tri-ethyl phosphate is described by H. K. Varma, S. N. Kalkura and R. Sivakumar in Ceramics International. 24 (1998), p. 467. The synthesis of hydroxyapatite according to this publication includes dissolution of calcium nitrate in tri-ethyl phosphate with further heating to 500° C. At this temperature, the degradation of tri-ethyl phosphate takes place with the formation of tri-calcium phosphate. Further calcination of tri-calcium phosphate leads to the formation of hydroxyapatite or a mixture of tri-calcium phosphate with hydroxyapatite. The final product has no controllable morphology and, according to XRD data, is contaminated with tri-calcium phosphate and/or calcium oxide.

Therefore, the need exists for hydroxyapatite having a controllable morphology and methods for producing the same.

Moreover, the need exist for a method of deposition of HA films over a substrate surface. Commercially, the plasma spray process (PS-HA) is the method most often used to deposit HA films on metallic implants. Films applied to the clinically relevant $Ti_6A_{14}V$ alloy (alloyed titanium with 6 wt. % aluminum and 4 wt. % vanadium), however, lack a Ti—HA chemical intermediate bonding layer such as $CaTiO_3$, and rely on mechanical interlock rather than chemical bonding to adhere the film to the substrate. As a result, in vivo coating delamination has been reported due to the greater interfacial strength between HA and bone, than between HA and titanium. Concerns have also been raised about the consequences of PS-HA's low crystallinity, lack of phase purity, passivation properties, and line-of-sight-limitations. In addition, plasma sprayed HA films fail to take advantage of pseudo-hexagonal HA crystallography to functionalize the film surface with the bioactive $\{10\bar{1}0\}$ crystallographic face and actively engineer protein adhesion. Molecular modeling and in vitro studies have shown that acidic bone proteins and other proteins found to bind HA with high affinity, bind to the $\{10\bar{1}0\}$ face of HA, which is prominently displayed on the six equivalent faces of the pseudo-hexagonal HA lattice[21-23]. HA films deposited by other techniques including sol-gel, pulsed laser deposition, magnetron sputtering, ion-beam deposition, and biomimetic crystallization share all or some of PS-HA's limitations. Therefore, there is a need to develop inexpensive reproducible HA film crystallization processes for substrates that deposit HA films with intermediate bonding layer over a substrate surface.

SUMMARY OF THE INVENTION

The present invention meets the need for hydroxyapatite having a controllable morphology, methods for producing such films and method for deposition of such films with intermediate bonding layer over a substrate surface.

In one embodiment, a continuous, two-step, phase sequenced apatite film deposition method includes dissolving a source of divalent ions, a source of hydroxide ions, and an organophosphate source of reactive phosphate anions in a common solvent; placing a metal substrate into the solution; heating the solution at a first temperature below the temperature at which said organophosphonate undergoes hydrolysis to release phosphate anions but at or above the temperature at which said divalent metal ions react with the metal substrate in the absence of phosphate anions to form with said metal substrate a layer of a binary oxide of said divalent metal ions and said substrate metal on said metal substrate; and heating the solution at a second temperature equal to or greater the temperature at which said organophosphate hydrolysis occurs, so that the organophosphate hydrolyzes to form reactive anions ions that react with said divalent metal and hydroxide ion sources in solution and with said binary oxide layer to form an apatite layer on said binary oxide layer.

Apatite layers according to the present invention include hydroxyapatites and other mineral apatites. Hydroxyapatites according to the present invention include stoichiometric and non-stoichiometric hydroxyapatites. Non-stoichiometric hydroxyapatites form when the Ca/P ratio (or divalent ion/phosphorous ratio for other mineral apatites) is or greater or less than 1.67 (5 divalent ion atoms such as calcium for 3 Phosphates). Numbers such as 1.56 or as high as 1.75 are examples where an aptatite phase is the only phase present. Hydroxy-apatites according to the present invention also include phase pure hydroxyapatite.

In one aspect, the divalent metal ions are chelated. In further aspects the divalent metal ions are calcium ions, which may be provided from a source selected from calcium hydroxide, calcium carbonate, calcium acetate, calcium halides, calcium oxide, calcium nitrate, calcium phosphate, and combinations thereof. Divalent ions of the instant invention are not necessarily limited to these embodiments and may also include one or a combination of divalent metal ions within the group Group II metals, divalent transition metals, or divalent lanthanides. In any of the foregoing embodiments, the divalent metal ions may be provided in an effective amount to achieve the process steps provided herein.

In another embodiment, the organophosphate source includes one or more compounds having the formula $(RO)_3PO$, wherein R represents hydrogen or an organic hydrocarbon radical hydrolysis derivative of organophosphate, provided that at least one R is not a hydrogen. In one aspect, the R group comprises one or more alkyl groups with hydrophilic substituents or hydrophilic groups with alkyl components. In further embodiments, the organophosphate source is selected from the group consisting of mono-, di-, and tri-substituted phosphoric acid esters. In even further embodiments, the organophosphate source is a tri-substituted phosphoric acid ester selected from the group tri-ethyl phosphate, tri-methyl phosphate, tri-butyl phosphate and combinations thereof. One or any combination of the foregoing organophosphate sources may be provided to produce the reactive anions of the instant invention, such as, but not limited to, $PO_4^{3-}$ ions.

In further embodiments, the source of the hydroxide ions is selected from the group ammonium hydroxide, calcium hydroxide, sodium hydroxide, potassium hydroxide, ammonia, calcium oxide, and combinations thereof.

In another embodiment, the metal substrate is selected from the group titanium, titanium alloy, steel, stainless steel, cobalt-chrome, and combinations thereof. In further embodiments of the instant invention, the common solvent is selected from the group water, ethylene glycol, 1,4-butanediol, ethanol, and combinations thereof.

In further embodiments the divalent metal ions, organophosphate source and ion concentrations are selected so that the apatite layer is a hydroxyapatite layer.

In even further embodiments of the foregoing, a source of dopant ions may be added to the solution at any point during the foregoing process. The addition of dopants can have a number of results. The dopants can be used to modulate solubility. They can also have effects on lattice parameters, growth rates, crystal/grain morphology, and crystallinity. Some dopants like silver can be used to add antimicrobial properties to the film. Dopants also play a significant role in how implant materials resorb. Also, the dopants can affect bioactivity, as hydroxyapatite is bioinert but becomes bioactive when dopants are added. Catalytic supports can be doped with catalyst elements. Dopant ions may be selected from divalent dopant ions, trivalent dopant ions, tetravalent dopant ions, pentavalent dopant ions, hexavalent dopant ions, heptavalent dopant ions, and the like.

Additional embodiments of the instant invention relate to a biocompatible hard tissue implant having a metal surface to which a phase pure hydroxyapatite film according to the present invention has been applied and a chromatography column or gas sensor or catalytic support having a metal surface to which an apatite film according to the present invention has been applied. The coated metal surfaces are prepared by a process comprising the steps of dissolving a source of divalent ion, a source of hydroxide ions, and an organophosphate source of reactive phosphate anions in a common solvent; placing a substrate into the solution; heating the solution at a first temperature below the temperature at which said organophosphonate undergoes hydrolysis to release phosphate anions but at or above the temperature at which said divalent metal ions react with the substrate in the absence of phosphate anions to form with said substrate a layer of a binary oxide of said divalent metal ions on said metal substrate; and heating the solution at a second temperature equal to or greater the temperature at which said organophosphate hydrolysis occurs, so that the organophosphate hydrolyzes to form reactive anions ions that react with said divalent metal and hydroxide ion sources in solution and with said binary oxide layer to form an apatite layer on said binary oxide layer.

Further embodiments include a method for preparing a metal surface for painting by applying an apatite film to the metal surface by a method according to the present invention. Another embodiment includes a method for protecting a metal surface from corrosion by applying an apatite film to the metal surface by a method according to the present invention.

BRIEF DESCRIPTION OF THE DRAWINGS

FIG. 1 is a table summarizing the characteristics of hydroxyapatite powders;

FIG. 2 is a table summarizing the conditions of the syntheses of exemplary hexagonal, spherical, tubular, barrel, and platelet hydroxyapatite particles;

FIG. 3 is a table summarizing the conditions of the syntheses of hydroxyapatite coatings;

DETAILED DESCRIPTION OF THE INVENTION

The present invention is related to hydroxyapatite particles and coatings having a controllable morphology. Methods of preparing the particles and coatings are also presented.

The ability to produce hydroxyapatite powders and films with controlled physical and chemical characteristics offers tremendous advantages for a wide range of applications suitable for this material. Hydroxyapatite has reported uses for biomedical, chromatographic, and piezoelectric applications. The primary focus has been to make these materials with a high degree of phase purity, that is, materials that possess a low concentration of tricalcium phosphate (TCP) or amorphous calcium phosphate (ACP) because impurities such as these are easily resorbed into aqueous solution.

However, the impact of using hydroxyapatite with a wide range of sizes and morphol-ogies has not been considered. Further, the applicants are unaware of any quantitative assessments of degree of agglomeration or aggregation of hydroxyapatite powder. For film synthesis, methods have been reported that produce dense films, however, no attention was focused on the morphology of the grains in the structure or their specific orientation.

There is a range of morphologies useful in the present invention. For example, hexag-onal morphologies, typically found in natural hydroxyapatite found in bone and teeth, are an important because such materials would have similar biological interactions. The present invention demonstrates that novel morphologies based on primary single crystalline particles or polycrystalline particles of controlled secondary morphology based on controlled aggregation of primary particles of controlled morphology is feasible.

Relevant morphologies on primary or secondary hierarchy include spheres, hexagons, tubular, platelets, barrels, and cube-shaped structures. Particles having such morphologies include particles that essentially have the morphologic shape. For example, for particles that are hexagons, the particles need not be perfect hexagons.

Using orthogonal a-b-c axes as a reference frame, several morphologies are defined as follows:

The term "spheres" is used herein to mean equiaxed particles having either a primary or secondary particle structure.

Figure 8:
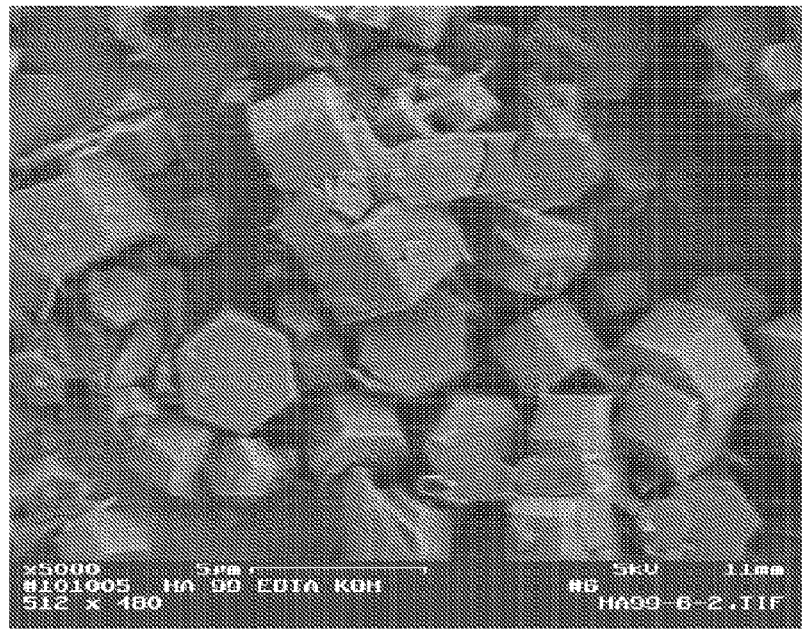
FIG. 8 is a scanning electron microscopy image of hexagonal hydroxyapatite particles having a low aspect ratio.

The term "platelets" is used herein to mean particles in the shape of a hexagon with an aspect ratio less than 1. Exemplary platelets are shown in FIG. 8.

Figure 9:
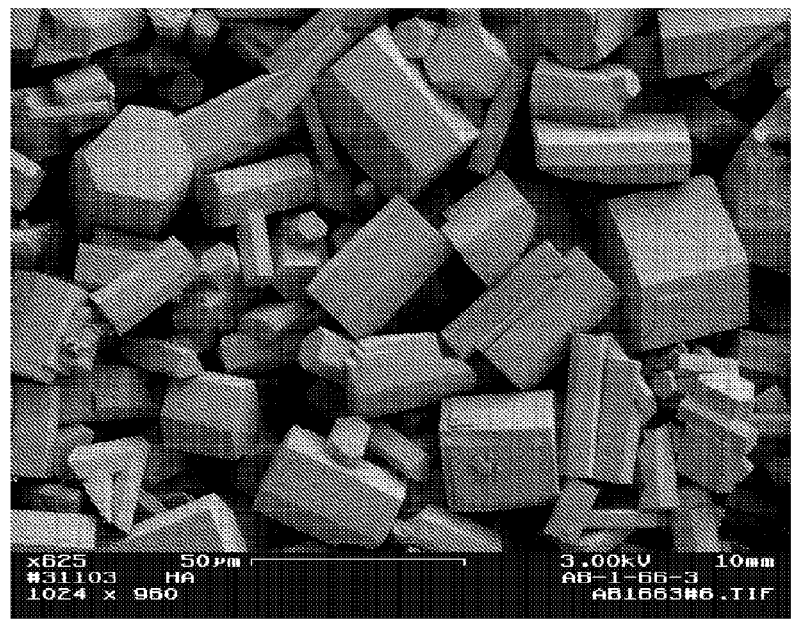
FIG. 9 is a scanning electron microscopy image of hexagonal hydroxyapatite particles having a high aspect ratio.

The term "hexagons" is used herein to mean equiaxed particles in the shape of a hexagon with an aspect ratio of 1-3. Exemplary hexagons are shown in FIGS. 8 and 9.

Figure 12:
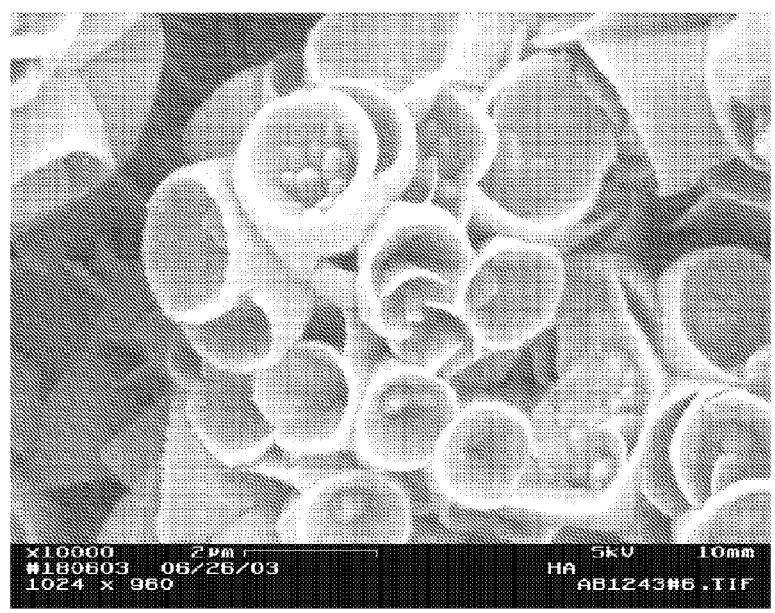
FIG. 12 is a scanning electron microscopy image of tubular hydroxyapatite particles.

The term "tubular" is used herein to mean short tubes with an aspect ratio of about 1, but hollowed out to give the appearance of coral. Exemplary tubular hydroxyapatite is shown in FIG. 12.

Figure 11:
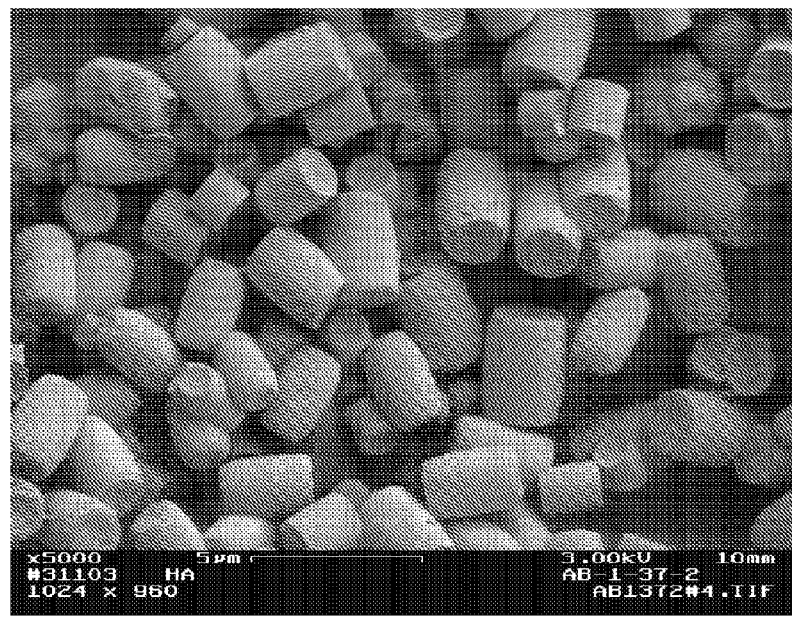
FIG. 11 is a scanning electron microscopy image of barrel hydroxyapatite particles.

The term "barrel" is used herein to mean truncated ellipsoidal particles that appear similar in shape to wooden barrels used to store liquid. Exemplary barrel particles are shown in FIG. 11.

The term "cube-shaped" is used herein to mean any orthogonal single-crystal particles in which the faces are square, rectangular, or both, which possess a cubic morphology. This definition also includes non-perfect cubes, that is, particles with an essentially cubic structure.

Figure 4:
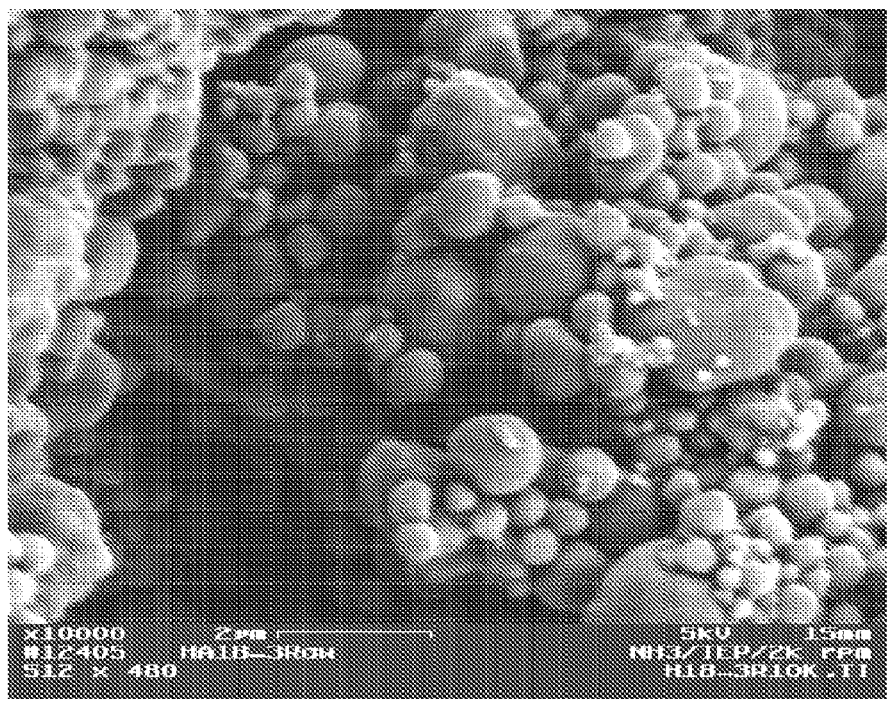
FIG. 4 is a scanning electron microscopy image of smooth spherical hydroxyapatite particles.
Figure 5:
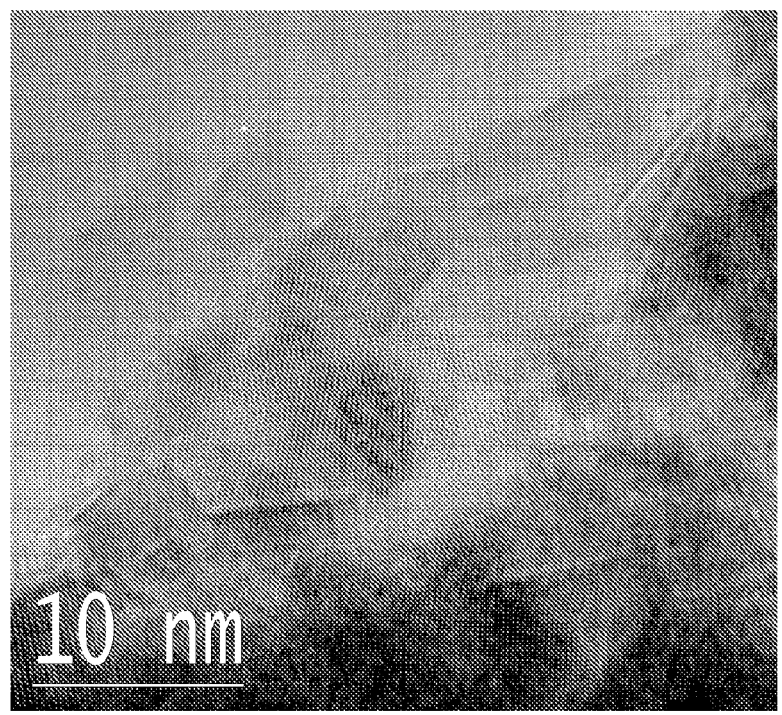
FIG. 5 is a TEM image of the interior surface of the smooth spherical hydroxyapatite particles.

The term "smooth" is used herein to mean a surface that has asperities smaller than the average thickness of the surface. An exemplary smooth particle is shown in FIG. 4.

Figure 6:
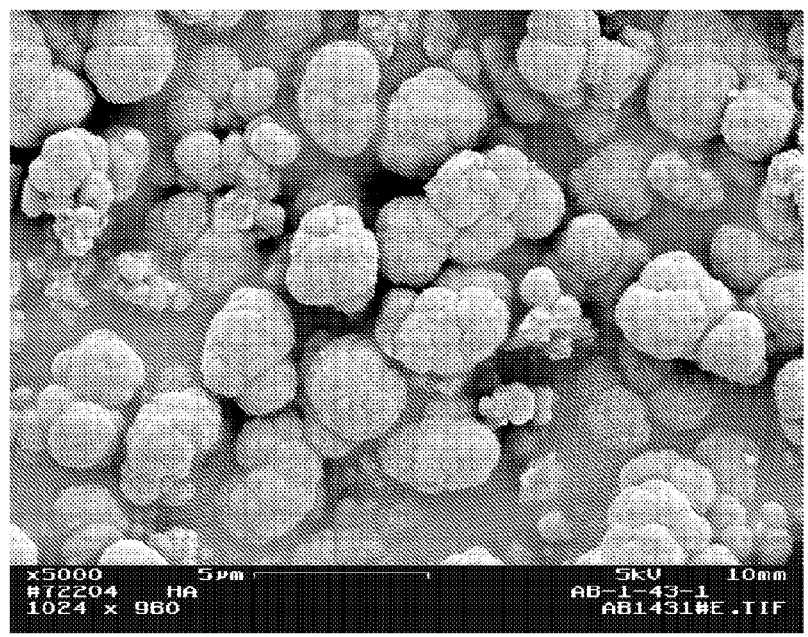
FIG. 6 is a scanning electron microscopy image of rough spherical hydroxyapatite particles.

The term "rough" is used herein to mean a surface that has asperities larger than the average thickness of the surface. An exemplary rough particle is shown in FIG. 6.

The term "passivate" is used herein to mean the formation of a hard and non-reactive dense film on the surface of a substrate that will inhibit corrosion of the substrate. The terms "passivation film" or "passivation coating" are used herein interchangeably to mean a film or coating formed over the surface of a substrate to inhibit gas or liquid media in contact with the film surface from interacting or communicating with the underlying substrate, thereby inhibiting processes such as corrosion and/or dissolution, for example by covering all or part of the substrate surface such that essentially no pores or pinholes extend from the substrate surface to the film surface.

The term "delayed-release organophosphate" is used herein to mean an organophosphate that does not fully hydrolyze to release reactive phosphate anions below a certain pre-defined temperature. In specific embodiments, the term "delayed-release organo-phosphate" means an organophosphate that does not fully hydrolyze to release reactive phosphate ions below 180° C.

The term "reactive phosphate anions" is used herein to mean the mono-valent, divalent or trivalent anions, or combination thereof, resulting from organophosphate hydrolysis, that are capable of reacting with solution divalent metal cations, hydroxide anions and the binary oxide layer to form an apatite layer.

"Room temperature" is defined herein as 25° C.

"Water-soluble" ion sources are defined as being materials having a solubility in water of at least about 2.0 g/L.

The morphology of the non-agglomerated non-aggregated phase-pure hydroxyapatite of the present invention is controllable. Preferred morphologies include: hexagons with a length that can be controlled from about 50 nm to about 5000 nm and an aspect ratio from about 0.5 to about 5; spheres having hexagonal primary particles and a secondary particle size that can be controlled from about 50 nm to about 5000 nm; tubular particles with a length that can be controlled from about 50 nm to about 5000 nm with an aspect ratio from about 0.5 nm to about 5 nm; and barrel-shaped particles with a length that can be controlled from about 50 nm to about 5000 nm with aspect ratio from about 0.5 to about 5.0.

Preferably, the non-agglomerated non-aggregated phase-pure hydroxyapatite is present in a powder form. The powder may contain one morphology or a mixture of different morphologies.

The characteristics of some exemplary morphologies are set out in FIG. 1.

The present invention is not limited to the preparation of hydroxyapatite, which is the calcium containing form or apatite. Replacement of calcium atoms in the hydroxyapatite structure with other divalent ion atoms in the method of the present invention provides other mineral apatites. The apatites of the present invention can also be used in a film form, which is made up of grains of apatite. The morphology of the grains in the apatite films can be controlled. Preferred morphologies for the grains include the same as noted above for the non-agglomerated non-aggregated phase-pure apatites.

The apatite films can be used to passivate the surface of a substrate, such as, metals, metal oxides, alloys, and polymers stable in alkaline media at elevated temperatures. A preferred metal substrate is titanium. Preferred alloy substrates include mild steel, stainless steel, cobalt/chrome, and titanium alloy. Preferred polymeric substrates include fluoro-polymers, polyvinylchloride, and polyethylene terephtalate. Particularly preferred film grain morphology and substrate combinations include a hexagonal grain film on a sapphire single crystal substrate and a cube-shaped grain film on zirconia.

Because the film of the present invention is preferably applied to a substrate by immersing the substrate in a solution and precipitating the film onto the substrate, the film can be coated onto substrates having simple as well as complex shapes with otherwise hard to view interior portions. In this case, reactive sites on the substrate surface define the locations where coatings will occur and the yield of the precipitation reaction will define the thickness of the coating. A reactive site is a surface where the precipitate from the solution can deposit by virtue of a range of bonding mechanisms including, but not limited to, van der Waals, covalent, ionic and metallic mechanisms. Thus, a substrate can be immersed in a liquid and a coating will result of uniform thickness in all locations of the object which have a substrate-liquid interface. Preferred substrate forms include porous substrates, wire meshes, wires, rods, bars, ingots, sheets, and free-form shapes.

The crystalline apatite grains may be oriented in a similar direction on the substrate.

Additionally, the crystalline grains on the substrate surface can have varying lengths.

The texture of the apatite films may be manipulated as discussed below to produce a smooth or rough film surface.

Synthetic routes of production of non-agglomerated non-aggregated apatites and apatite films with controllable morphologies are also presented herein. The methods are based on the controlled supply of the ingredients of the precursor to the reaction mixture by using slow degradable components and, optionally, chelating agents. The application of chelating agents makes homogeneous precipitation of apatites possible.

In this invention, a solvothermal method is presented that enables apatites to be crystallized as a powder or film with controlled crystal size and morphology. In a solvothermal process, single phase or multi-phase reactions using solutions, suspensions, or gels are reacted to crystallize oxides directly from solution typically at temperatures that range from room temperature to about 350° C. and pressures that range from 1 to 500 atm. The solvent medium is typically water where the process is referred to as a hydrothermal process. However, reactions commonly utilize non-aqueous liquids, such as, ethylene glycol, 1,4-butanediol, and ethanol, which can also be co-mixed with water.

Solvothermal synthesis can also use precipitation from homogeneous solution (PFHS) methods for crystallization, giving greater control over morphology and size. In a PFHS reaction, a precipitation reaction is regulated by a chemical reaction that releases a soluble species that is capable of supersaturating a solution and precipitating the thermodynamically and kinetically favored phase. PFHS systems are uniform single-phase solutions that transform to a multi-phase system containing the powder or film of interest. PFHS systems function by controlling the crystallization kinetics, namely the rates of nucleation, growth and even ageing, which are the processes responsible for size and morphology control. For these types of processes, it is important to find the appropriate reactant concentrations, tempera-tures and pressures where crystallization kinetics are controlled. Compositional, temperature, and pressure uniformity are critical to ensure that all processes occurring the reactor are occurring uniformly. Thus, finding a precipitation process that uses the same chemical components alone is not sufficient to define a suitable PFHS system. PFHS reactions for hydroxyapatite have been developed for both ceramics and films. However, in all of these reactions, attention has been paid to release of the divalent metal ion species but not the organophosphonate species.

In the current invention, the release of phosphorous species is controlled and in some cases, the release of divalent metal ion species is also controlled. The organophosphate source of such reactive phosphate anions may be represented by the phosphoric acid esters of general formula $(RO)_3PO$. In the formula, R is a hydrolyzable water soluble or miscible organophosphate ester leaving group. Examples include hydrogen or an organic hydrocarbon radical hydrolysis derivative of the organophosphate, provided that at least one R is not H. The solubility of tri-organo phosphates decreases with the increase of radical molecular weight. Trimethyl- and triethylphosphates are water miscible. Solubility of tripropyl phosphate is 6450 mg/L at 25° C. Solubility of tributyl phosphate is about 1000 mg/L at 4° C. and decreases with temperature, achieving $2.85 \times 10^{-4}$ mg/L at 50° C.

The release of phosphate ion is a multi-step process comprising the set of chemical reactions:

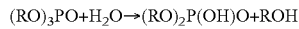

$(RO)_3PO + H_2O \rightarrow (RO)_2P(OH)O + ROH$

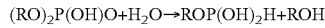

$(RO)_2P(OH)O + H_2O \rightarrow ROP(OH)_2H + ROH$

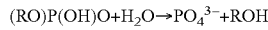

$(RO)P(OH)O + H_2O \rightarrow PO_4^{3-} + ROH$

In alkaline media, substituted phosphoric acids formed in these reactions dissociate according to the equations:

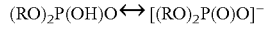

$(RO)_2P(OH)O \leftrightarrow [(RO)_2P(O)O]^-$

$ROP(OH)_2O \leftrightarrow [ROP(OH)O]^- \leftrightarrow +[ROP(O)O]^{2-}$

Reactive phosphate anions include $PO_4^{3-}$ anions and intermediate species that are capable of reacting with solution divalent metal cations, hydroxide anions and the binary oxide layer to form an apatite layer. The optimum balance of solubility and rate of hydrolysis is achieved in tri-ethyl phosphate, although tri-methyl and tri-butyl phosphate can be useful. Derivatives of phosphoric acid esters such as mono- and di-substituted acids also can be used in this process. Other suitable organophosphates include organophosphates in which the organic hydrocarbon groups are alkyl groups with hydrophilic substituents or hydrophilic groups with alkyl components such as alkoxy groups, alkyl carboxylate groups, and the like.

Until now, alkaline hydrolysis of tri-ethyl phosphate (TEP) was limited to hydrolysis of the first ester group with formation of di-ethyl phosphoric acid or its salts. Accordingly, the application of tri-ethyl phosphate in hydroxyapatite synthesis was limited to high temperature processes i.e. above 350 presumably 500° C. At such conditions, however, the uncontrollable degradation of tri-ethyl phosphate occurs.

The present invention employs a hydrothermal tri-ethyl phosphate hydrolysis in which complete hydrolysis of all ester groups is achieved in a relatively slow mode at temperatures below about 300° C., preferably from about 180 to about 250° C., with a controlled release of the phosphate ion. Because of the homogeneous nature of tri-ethyl phosphate hydrolysis in this process, phosphate ion is supplied uniformly over the entire reaction volume with the onset of total hydrolysis of tri-ethyl phosphate, which takes place at about 180° C. Hydrolysis of the first and the second ester groups takes place at lower temperature in agreement with the data of previous researchers.

One of the synthetic routes according to this invention utilizes hydrothermal hydrolysis of TEP in the presence of weak alkali (ammonia). During the first and second steps of hydrolysis, divalent metal ions, such as calcium ions, added as a water-soluble salt (nitrate, chloride etc.), partially precipitate at elevated temperature as a metal hydroxide.

The second route of apatite synthesis according to the present invention includes using chelating agents, preferably ethylene diamine tetracetic acid (EDTA) and its salts. The function of EDTA in this process is to serve as a chelating agent for the metal, preventing the formation of the metal hydroxide even in the presence of strong alkali (KOH). For calcium, the reaction is according to the following:

$Ca^{2+} + EDTA \leftrightarrow [Ca^{2+}EDTA]$

This shifts the process to homogeneous nucleation, having both the phosphate decomposition and the calcium-EDTA complex decomposition as the rate limiting steps. It is believed that hydrolysis of tri-ethyl phosphate triggers the release of calcium ions from the calcium-EDTA complex with further bonding of the calcium and phosphate moieties into the apatite structure.

The instant invention is not limited to the use of calcium ions, or to chelated calcium ions and may be performed using any divalent metal ions, which may be optionally chelated. Such divalent metal ions may be selected from divalent group II metals, divalent transition metals, divalent lanthanides, and the like, including magnesium, strontium, iron, and so forth. The divalent ions used may be provided in any amount effective to achieve the process steps provided herein.

An exemplary method for producing an apatite in accordance with the present invention includes dissolving a water-soluble organic or inorganic divalent metal ion salt in a solvent; adding a hydrolyzable organophosphate of general formula $(RO)_3PO$ to the solution, wherein R represents an organic hydrocarbon radical, hydrogen, or a hydrolysis derivative of the organophosphate; adding a hydroxide ion source to the solution; and applying heat to the solution.

Also presented is a method for producing an apatite film, which involves dissolving a chelating agent in a solvent; adding a water-soluble organic or inorganic divalent metal ion salt to the solution; adding a hydrolyzable organophosphate of general formula $(RO)_3PO$ to the solution, wherein R represents an organic hydrocarbon radical, hydrogen, or a hydrolysis derivative of the organophosphate; adding a hydroxide ion source to the solution; placing a substrate into the solution; and applying heat to the solution and substrate.

Examples of specific reaction conditions are set out in the Examples section below, and in FIGS. 2 and 3.

Examples of calcium ion sources include calcium hydroxide, calcium carbonate, calcium acetate, calcium halides, calcium oxide, calcium nitrate, calcium phosphate, and the like. Equivalent sources of other divalent metal ions may also be used. Suitable solvents include water and organic solvents.

The optional chelating agent is used for the preparation of films, and also the following particle morphologies: platelets, hexagons, barrels, and tubular structures. Suitable chelating agents include ethylendiamine tetracetic acid and the like.

The solubility of the organophosphate in water is, preferably, not less than 5% by weight at room temperature. Additionally, a preferred organophosphate is one that is miscible with water at room temperature. Examples of suitable organophosphates include tri-ethyl phosphate, tri-methyl phosphate, tri-butyl phosphate, and the like. Derivatives of phosphoric acid esters such as mono- and di-substituted acids also can be used in this process. Organophosphates with hydrophilic alkyl-containing groups can also be used, such as alkoxy groups or alkyl groups with hydrophilic substituents.

Suitable hydroxide ion sources include hydroxide-containing compounds such as ammonium hydroxide, calcium hydroxide, sodium hydroxide, potassium hydroxide, and the like, and compounds that generate hydroxide ion in aqueous solution, such as ammonia, calcium oxide, and the like.

The solution is preferably heated to a temperature less than 300° C. Preferred heating temperatures range from about 180° C. to about 250° C. The solution is preferably reacted in a sealed pressure vessel, such as an autoclave at autogenous pressure up to 500 atm. An autogenous pressure between about 20 and about 25 atm is preferred.

Applicants have unexpectedly discovered that below 180° C. incomplete hydrolysis of organophosphates, such as tri-ethyl phosphate, and the absence of free phosphate ions delays HA crystallization. This discovery was originally reported in Haders, D.; Burukhin, A.; Zlotnikov, E.; Riman, R. E. *Chemistry of Materials*, 2008, 20, 7177-7187, and Haders, D., Burukhin, A., Huang, Y., Cockayne, D. J. H., Riman, R. E. Crystal Growth & Design, 2009, 9, 3412-3422, which are incorporated herein by reference in their entireties. By delaying release of uncomplexed phosphate ions, reactions involving calcium ions and the substrate are initiated to form an adherent interfacial layer that enables chemical bonding of the apatite film to the substrate surface. Above 180° C., complete organophosphate hydrolysis occurs and the release of free phosphates initiates the deposition of apatite film on the interfacial layer.

Accordingly, another embodiment of the current invention provides a continuous, two-step, phase sequenced apatite film deposition method. This method is especially suitable for the deposition of hydroxyapatite film over the surface of a substrate such as titanium or titanium alloys. The method includes dissolving a chelated source of calcium ions, a source of hydroxide ions, and a delayed-release organophosphate source in a common solvent; placing a substrate into the solution; heating the solution at a first temperature below the temperature at which said organophosphonate undergoes hydrolysis to release phosphate anions but at or above the temperature at which said calcium ions react with the substrate in the absence of phosphate ions to form an oxide of calcium on said substrate; and heating the solution at a second temperature equal to or greater the temperature at which said organo-phosphate hydrolysis occurs, so that the delayed-release organophosphate hydrolyzes to form $PO_4^{3-}$ ions that react with said calcium and hydroxide ion sources to deposit hydroxyapatite on said substrate. Substitution of other divalent ions for calcium will produce other mineral apatites.

In specific embodiments, the first temperature is less than or equal to about 180° C. and the second temperature is equal to or greater than about 180° C. Accordingly, the solution may be preheated to 180° C. and then heated to between about 180° C. and about 300° C., and more preferably between about 180° C. and about 250° C. Alternatively, the solution may be preheated to 180° C. and maintained at that temperature until an apatite film of desired quality is formed. The step of preheating the solution to 180° C. may last between 0 and about four hours. The solution may be maintained at the second temperature for at least 6 hours.

The texture of the apatite films of the present invention can be controlled by adjusting the amount of time the substrate is left in the reactor. For example, the longer the substrate is left in the reactor, the rougher the surface becomes. Surface smoothness or roughness can be verified through visual appearance using SEM. (See FIGS. 4 and 6, for example). In the case of the films of the present invention, steel was observed to provide a smoother film surface than titanium.

In the present invention, texture relates to two aspects: crystallographic orientation and surface shape. In an example of crystallographic orientation, the c-axis of multiple hexgonal rods can be oriented approximately normal to the surface of the substrate. This would create the appearance of the hexagonal rods being vertical. When the rods all have the same approximate length, the rods form a film with just a portion of the rods exposed at the surface of the film. However, when the rods are of varying lengths, the rods protrude at varying lengths from the surface of the film and lead to a varying film topography. These "hills and valleys" of the surface can play a big role in controlling bioactivity. For example, U.S. Pat. No. 6,419,491 a patent recently issued by Ricci that discusses this for dental materials. The disclosure of the Ricci patent is incorporated herein by reference.

There are many reasons why control of the size and morphology of a powder or film would provide utility for devices based on hydroxyapatite. In the biomedical field, materials with controlled morphology means that surfaces have specific crystallographic faces. These faces offer means by which proteins can selectively adsorb. Such an implant would mineral-ize bone at the interface and thus be osteoconductive. The excellent protein selectivity of this interface would enable the mineralization to proceed faster than a conventional material not having controlled morphology and hence poor protein selectivity. At the same time, it is con-ceivable that presentation of the appropriate interface in a material can influence biochemist-try in a manner where cells in the body can differentiate into bone-producing cells, which could enable bone mineralization in regions where an implant surface is absent. These types of materials are osteoinductive. It has also been reported that the piezoelectric properties are relevant to biomedical applications where bone healing is important.

For applications where piezoelectricity is important, control of the orientation of the crystal relative has a major effect on its electromechanical properties. In many cases, piezoelectric materials are used as mass balances and sensors where adsorption onto its interface can control resonance properties. Thus, the combination of selective adsorption properties and ability to control orientation of apatite crystals present novel device opportunities for applications such as selective chemical sensing and even frequency control.

In addition to the foregoing, in one aspect of the process, one or more dopant ions are optionally added to the solution. Apatites can accommodate a lot of different ions, practically the whole periodic table. J. C. Elliot, Structure and Chemistry of the Apatites and Other Calcium Orthophosphates, Elsevier, 1994, discloses that almost every anion and cation imaginable that can go into solid solution, whether its the elemental ion or a complex ligand, like carbonate or $SeO_4^{2-}$ can be inserted into an apatite structure. The valences vary from mono-valent to a valence of 7 ($ReO_5^{3-}$ for example has Re as +7), i.e., divalent, trivalent, tetravalent, etc. To this end, the dopant ions may be added at any point during the process. The dopant ions may be provided in any concentration effective to achieve the foregoing.

In the field of drug delivery, particles or films with well-defined morphology can present numerous advantages. Morphology control offers preferred crystallographic faces that can preferentially adsorb specific drug molecules. By controlling the size of the particles, the solubility and dissolution of the drug can be enhanced as the size of the particles are reduced. In addition, these materials can be synthesized as dispersible colloids. The surface topology or roughness of a film can also be used to enhanced or restrict dissolution. It is also conceivable to incorporate cations and anions to tailor the dissolution properties of apatites using ions such as magnesium or carbonate.

For applications such as chromatography, access to crystalline apatite with controlled size and morphology can enhance selectivity. Crystals with controlled morphology may selectively adsorb species in a flow stream because the crystallographic faces present specific adsorption sites that are compatible with some molecules and not others. Apatite coatings thus have utility for proteomics and for protein separations. By controlling the size, the probability of access to that surface is increased as the size decreases since there is a concomitant increase in surface area.

Corrosion protection is a novel application for coatings of apatites not previously considered. Such a consideration is reasonable because apatites are highly insoluble in aqueous solutions. Furthermore, growth of an adherent insoluble passivating apatite layer on a metallic substrate should exhibit excellent performance. The use of sandblasting and other surface roughening techniques allows better film adhesion, giving it limitless metal substrate possibilities.

Given that apatites such as hydroxyapatite have no toxicity and the components are low cost, such a technology presents great promise for a range of applications including, but not limited to, architectural, automotive, chemical processing, and other applications where corrosion resistance for metallic surfaces is desired. Because apatites are insoluble in aqueous solution, these coatings can serve as an effective primer coat. Further, their white color can also provide opportunities for aesthetically white finishes. Varying of synthesis conditions provides an opportunity for dense and porous films as desired. A dense film is defined as a coating where the surface cannot be penetrated far enough to reach the substrate and a porous film is defined as a coating where the substrate is readily and easily accessible to fluid or other mediums.

Devices based on apatites are typically in the form of polycrystalline ceramics, polymer-ceramic composites, or films on a metallic surface such as titanium. The powders produced in this invention could be used in conventional processes to make all three forms of materials, using conventional methods such as solid state sintering for polycrystalline ceramics, polymer-melt processing for polymer-ceramic composites and plasma spraying for hydroxyapatite-coated titanium metal. The films in this invention can be used to grow films directly onto the metal surfaces without the need for any high temperature processing. Because apatites are insoluble in aqueous solution, these coatings will not dissolve.

The hydroxyapatite of the present invention are also useful in the preparation of compounds for use as granular fill for direct incorporation into the hard tissues of humans or other animals, and as bone implantable materials. The present invention thus includes granular fill compounds, bone implant materials, tooth filling compounds, bone cements and dentifrices containing the HAp particles and films of the present invention. The products are formulated and prepared by substituting the HAp of the present invention for HAp in conven-tional HAp-based products. The compounds may be prepared in the form of metallic and polymeric HAp composites.

EXAMPLES

Example 1

Synthesis of Spherical Hydroxyapatite Particles 59 g of calcium nitrate tetrahydrate ($Ca(NO_3)_2*4H_2O$ Fisher Scientific) were placed into 482 g of de-ionized water and dissolved under magnetic stirring. After total dissolution of calcium nitrate, 18.3 g of tri-ethyl phosphate (TEP, Aldrich, 99.8+%) were added to the solution and stirred for 10 minutes. Then, 34 g of aqueous ammonia (28%) were added and mixed 5-10 min.

The resulting solution was then filtered through a 0.22 m Millipore filter and loaded into Teflon™ liner. The loaded liner was placed into 1 L autoclave (Model 4531, Parr Instruments) equipped with electrical heater, cooling coil, thermocouple and blade stirrer. Stirring of the reaction mixture was started immediately after the autoclave closing and remained at 1200 rpm during the entire synthesis.

Heat control of the synthesis included heating of the reaction mixture from ambient temperature to 200° C. (1 hour), maintaining temperature of 200±2° C. (24 hours) and cooling to ambient temperature (~20 minutes).

After completion of the synthesis, the reactor was unloaded and product was separated by filtration through a 0.22 m Millipore filter. Hydroxyapatite was washed on the filter 5 times by de-mineralized water and then dried at 85° C. in the laboratory oven.

The prepared HA powder was characterized by powder X-ray diffraction by Kristalloflex D500 diffractometer (Siemens) with Ni-filtered CuKa radiation over the 2 q range 10-80° by a step of 0.02°. Only hydroxyapatite peaks were found. Particle size and morphology were investigated by a field emission scanning microscope (FESEM, Model DSM 962 Gemini, Carl Zeiss-Leo; Philips XL30 FEG-SEM) (FIG. 4) on gold-coated samples. Number mean particles size was determined by light scattering technique (Coulter) as 0.098±0.09 microns.

Example 2

Control of Spherical Hydroxyapatite Particle Size 59 g of calcium nitrate tetrahydrate ($Ca(NO_3)_2*4H_2O$ Fisher Scientific) were placed into 482 g of de-ionized water and dissolved under magnetic stirring. After total dissolution of calcium nitrate, 18.3 g of tri-ethyl phosphate (TEP, Aldrich, 99.8+%) were added to the solution and stirred for 10 minutes. Then, 34 g of aqueous ammonia (28%) were added and mixed 5-10 min.

The solution was then filtered through a 0.22 m Millipore filter and loaded into a Teflon™ liner. The loaded liner was placed into a 1 L autoclave (Model 4531, Parr Instruments) equipped with an electrical heater, cooling coil, thermocouple, and blade stirrer. Stirring of the reaction mixture was started immediately after the autoclave closing and sustained during the entire synthesis at the chosen rotation speed. In consequent syntheses with the identical recipe 200, 700 and 1700 rpm were maintained through the entire synthesis.

Heat control of the synthesis included heating the reaction mixture from ambient temperature to 200° C. (1 hour), maintaining temperature of 200±2° C. (24 hours) and cooling to ambient temperature (~20 minutes).

After completion of the synthesis, the reactor was unloaded and the product was separated by filtration through a 0.22 m Millipore filter. Hydroxyapatite was washed on the filter 5 times by de-mineralized water and then dried at 85° C. in the laboratory oven.

Figure 7:
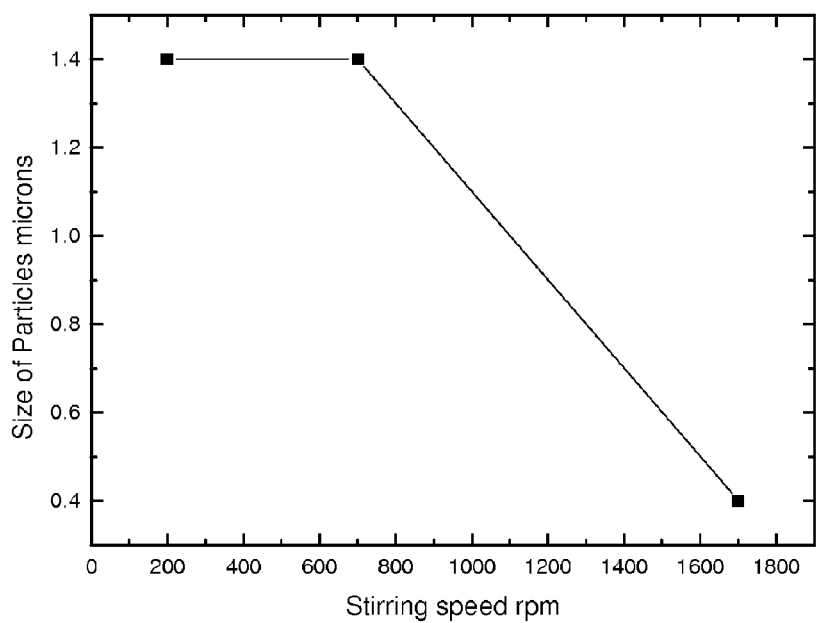
FIG. 7 is a graph showing spherical particle size as a function of stirring speed.

The prepared HAp powder was characterized by powder X-ray diffraction by Kristalloflex D500 diffractometer (Siemens) with Ni-filtered CuKa radiation over the 2 q range 10-80° by a step of 0.02°. Only hydroxyapatite peaks were found. Particle size and morphology were investigated by a field emission scanning microscope (FESEM, Model DSM 962 Gemini, Carl Zeiss-Leo; Philips XL30 FEG-SEM) on gold-coated samples. Spherical hydroxyapatite morphologies are shown in FIGS. 4 and 6. Dependence of size of the particles vs rotation speed is presented in FIG. 7.

Example 3

Synthesis of Hexagonal Hydroxyapatite Particles 0.44 g of EDTA (Fisher Scientific) were dissolved in 58.3 g of de-mineralized water. Then, 0.35 g of calcium nitrate tetrahydrate ($Ca(NO_3)_2*4H_2O$ Fisher Scientific) were placed into solution and dissolved under magnetic stirring. After total dissolution of calcium nitrate, 0.22 g of tri-ethyl phosphate (TEP, Aldrich, 99.8+%) were added to the solution and stirred for 10 minutes. Then, 0.67 g of potassium hydroxide were added and mixed until total dissolution.

The solution was then filtered through a 0.22 m Millipore filter and loaded into a Teflon™ liner. The loaded liner was placed into a 125 ml autoclave (Model 4748, Parr Instruments). The reactor was placed in a preheated to 180° C. laboratory oven (Fisher Scientific Isotemp oven, model 655G) for 20 hours. Due to high thermal inertia of the massive autoclave, working temperature was achieved in about 4 hours.

After completion of the synthesis, the reactor was cooled by quenching in running cold tap water for 30 minutes, unloaded, and product was separated by filtration through a 0.22 m Millipore filter. Hydroxyapatite was washed on the filter 5 times by de-mineralized water and then dried at 85° C. in the laboratory oven.

The prepared HA powder was characterized by powder X-ray diffraction by Kristalloflex D500 diffractometer (Siemens) with Ni-filtered CuKa radiation over the 2 q range 10-80° by a step of 0.02°. Only hydroxyapatite peaks were found. Particle size and morphology were investigated by a field emission scanning microscope (FESEM, Model DSM 962 Gemini, Carl Zeiss-Leo; Philips XL30 FEG-SEM) on gold-coated samples.

For the preparation of low aspect ratio hexagons, 2.63 g EDTA, 2.13 g $Ca(NO_3)_2$, 1.32 g TEP, and 4.03 g KOH were dissolved in 49.89 ml of de-mineralized water. The oven was preheated to 200° C. and total duration of synthesis was 25 hours. Cooling of the reactor, washing, separation and characterization of hydroxyapatite followed the procedure described above. Morphology of the obtained in this synthesis hydroxyapatite is illustrated by microphotograph in FIG. 8.

Example 4

Control of Hexagonal Hydroxyapatite Particle Size

Figures 10, 10A:
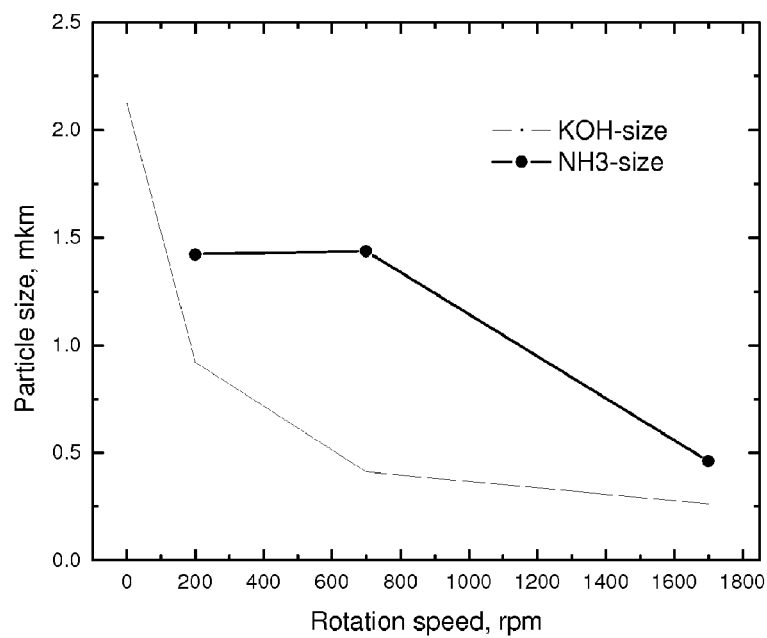
FIG. 10 is a table summarizing conditions for controlling the synthesis of exemplary hexagonal hydroxyapatite particles.
FIG. 10a is a graph showing the effect of rotation speed on particle size.

Control over the aspect ratio and size of hexagonal hydroxyapatite particles was achieved by variation of reagent concentration, temperature, and time of synthesis. Amounts of EDTA, $(Ca(NO_3)_2*4H_2O$, TEP, and KOH are presented in FIG. 10.

EDTA (Fisher Scientific) was dissolved in de-mineralized water. Then, calcium nitrate tetra hydrate ($Ca(NO_3)_2*4H_2O$ Fisher Scientific) were placed into solution and dissolved under magnetic stirring. After total dissolution of calcium nitrate, tri-ethyl phosphate (TEP, Aldrich, 99.8+%) was added to the solution and stirred for 10 minutes. Then, potassium hydroxide was added and mixed until total dissolution.

The solution was then filtered through a 0.22 m Millipore filter and loaded into a Teflon™ liner. The loaded liner was placed into a 125 ml autoclave (Model 4748, Parr Instruments). The reactor was placed into a laboratory oven preheated to working temperature specified in FIG. 10 (Fisher Scientific Isotemp oven, model 655G) for 20 or 40 hours.

After completion of the synthesis, the reactor was cooled by quenching in running cold tap water for 30 minutes, unloaded, and product was separated by filtration through a 0.22 m Millipore filter. Hydroxyapatite was washed on the filter 5 times by de-mineralized water and then dried at 85° C. in the laboratory oven.

The prepared HAp powder was characterized by powder X-ray diffraction by Kristalloflex D500 diffractometer (Siemens) with Ni-filtered CuKa radiation over the 2 q range 10-80° by a step of 0.02°. Only hydroxyapatite peaks were found. Particle size and morphology were investigated by a field emission scanning microscope (FESEM, Model DSM 962 Gemini, Carl Zeiss-Leo; Philips XL30 FEG-SEM) on gold-coated samples.

Aspect ratio and length of the particles were measured directly in the images using Adobe Photoshop 5.5.

Example 5

Synthesis of Barrel-Type Hydroxyapatite Particles 0.44 g of EDTA (Fisher Scientific) were dissolved in 58.3 g of de-mineralized water. Then, 0.35 g of calcium nitrate tetra hydrate ($Ca(NO_3)_2*4H_2O$ Fisher Scientific) were placed into solution and dissolved under magnetic stirring. After total dissolution of calcium nitrate 0.22 g of tri-ethyl phosphate (TEP, Aldrich, 99.8+%) were added to the solution and stirred for 10 minutes. Then, 0.67 g of potassium hydroxide were added and mixed to total dissolution.

The solution was then filtered through a 0.22 m Millipore filter and loaded into a Teflon™ liner. The loaded liner was placed into a 125 ml autoclave (Model 4748, Parr Instruments). The reactor was mounted on a magnetic stirrer and heated with electrical tape to working temperature of 230° C. during 1 hour. Total duration of the synthesis is 24 hours.

After completion of the synthesis, the reactor was cooled at the room temperature of about 25° C. during 2 hours, unloaded and product was separated by filtration through a 0.22 m Millipore filter. Hydroxyapatite was washed on the filter 5 times by de-mineralized water and then dried at 85° C. in the laboratory oven.

The prepared HA powder was characterized by powder X-ray diffraction by Kristalloflex D500 diffractometer (Siemens) with Ni-filtered CuKa radiation over the 2 q range 10-80° by a step of 0.02°. Only hydroxyapatite peaks were found. Particle size and morphology were investigated by a field emission scanning microscope (FESEM, Model DSM 962 Gemini, Carl Zeiss-Leo; Philips XL30 FEG-SEM) on gold-coated samples. Morphology of the obtained in this synthesis hydroxyapatite is illustrated by microphotograph in FIG. 11.

Example 6

Synthesis of hydroxyapatite film 0.44 g of EDTA (Fisher Scientific) were dissolved in 58.3 g of de-mineralized water. Then, 0.35 g of calcium nitrate tetrahydrate ($Ca(NO_3)_2 \cdot 4H_2O$ Fisher Scientific) were placed into solution and dissolved under magnetic stirring. After total dissolution of calcium nitrate 0.22 g of tri-ethyl phosphate (TEP, Aldrich, 99.8+%) were added to the solution and stirred for 10 minutes. Then 0.67 g of potassium hydroxide were added and mixed till total disolution.

Solution was filtered through a 0.22 m Millipore filter and then loaded into a Teflon™ liner. The loaded liner was placed into a 125 ml autoclave (Model 4748, Parr Instruments). Sample of the mild steel 1008 was roughened with sand paper #320 and then placed into autoclave in inclined position under the angle about 60°. Reactor was placed in a preheated 195° C. laboratory oven (Fisher Scientific Isotemp oven, model 655G) for 15.3 hours.

Following completion of the reaction, the reactor was air cooled at room temperature about 25° C. during 2 hours. The coated sample was washed 5 times by de-mineralized water and then air dried at room temperature.

Figure 13:
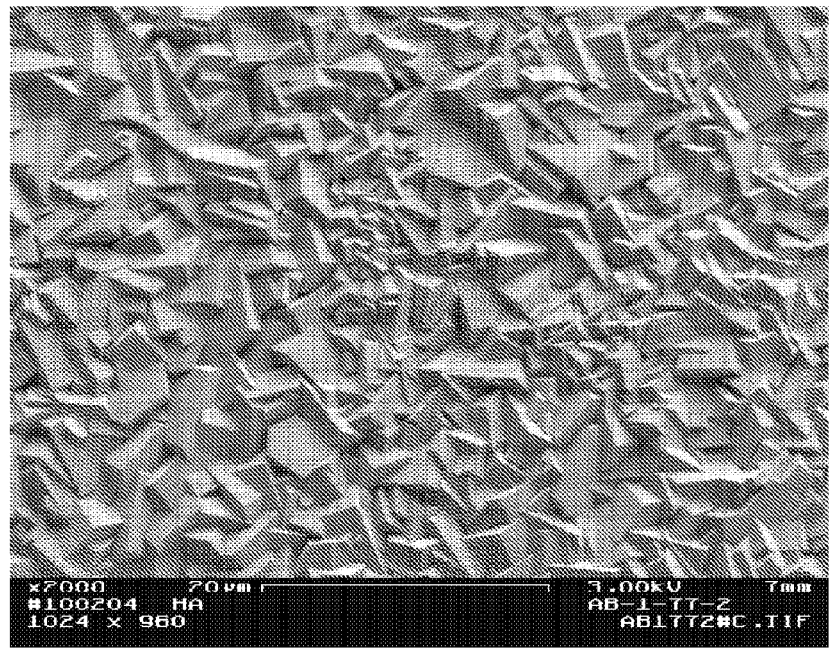
FIG. 13 is a scanning electron microscopy image of a hydroxyapatite coating on mild steel.
Figure 14:
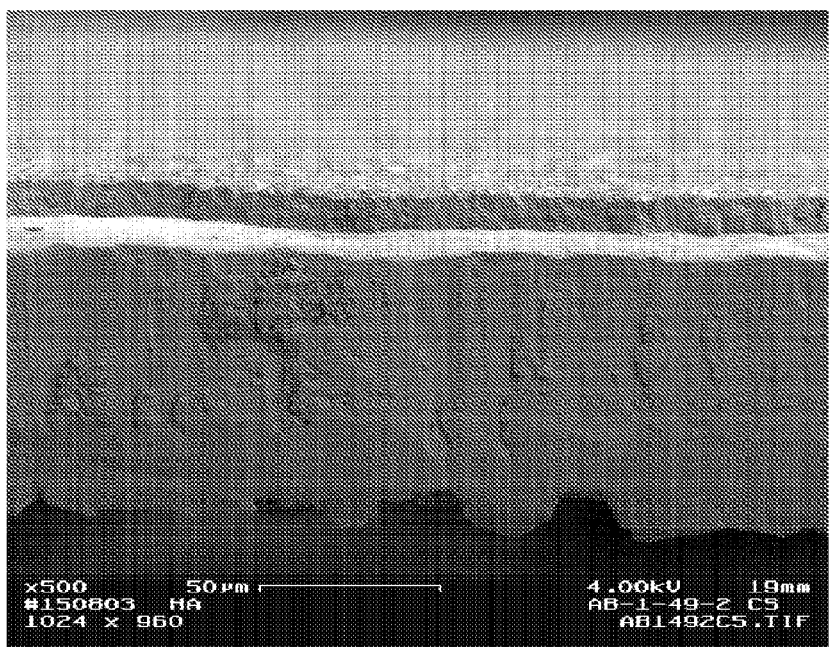
FIG. 14 is a scanning electron microscopy image of a hydroxyapatite coating on stainless steel.
Figure 15:
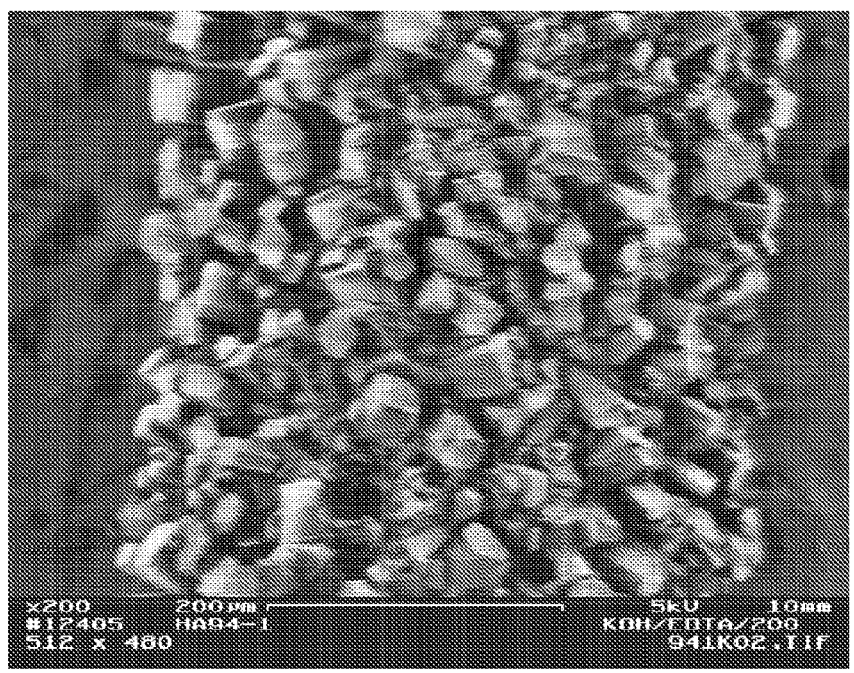
FIG. 15 is a scanning electron microscopy image of a hydroxyapatite coating on titanium wire.
Figure 16A:
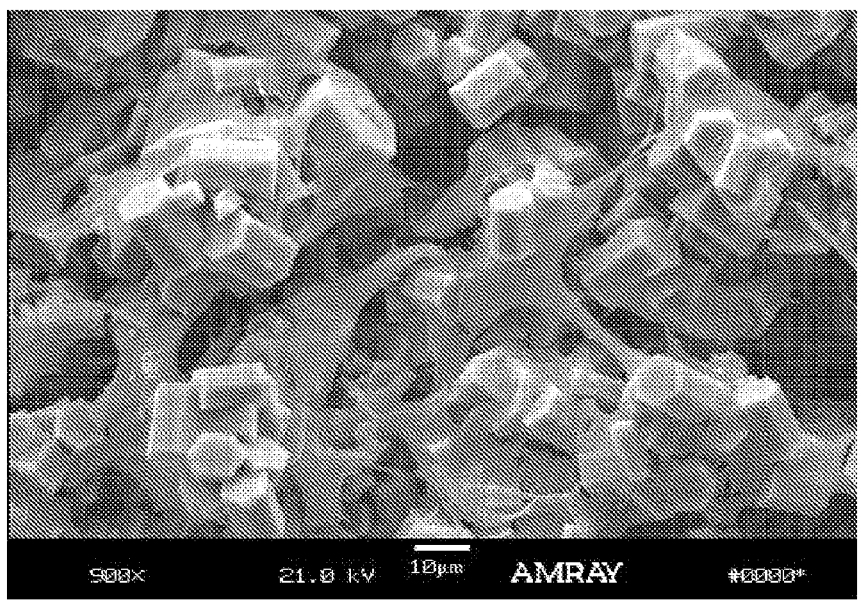
FIGS. 16a-d are scanning electron microscopy images of cell spreading on hexagonal hydroxyapatite.
Figure 16B:
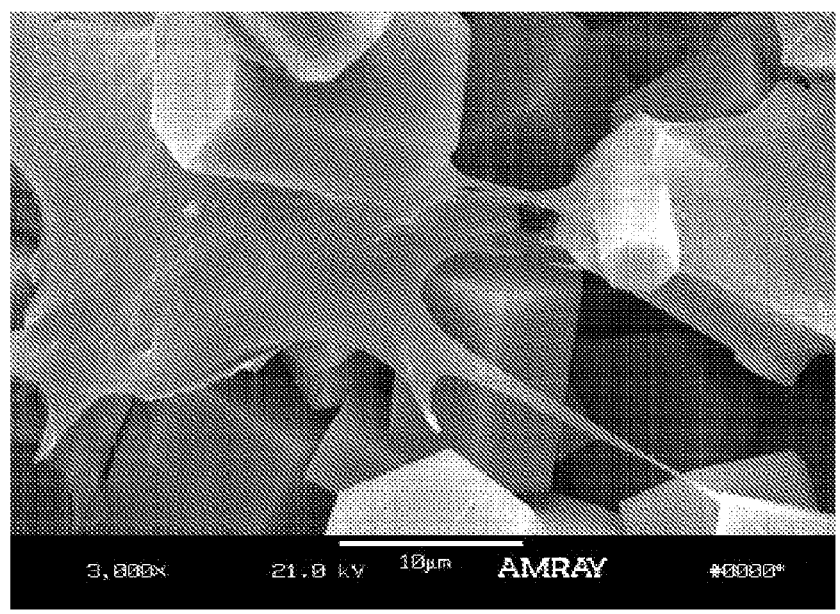
Figure 16C:
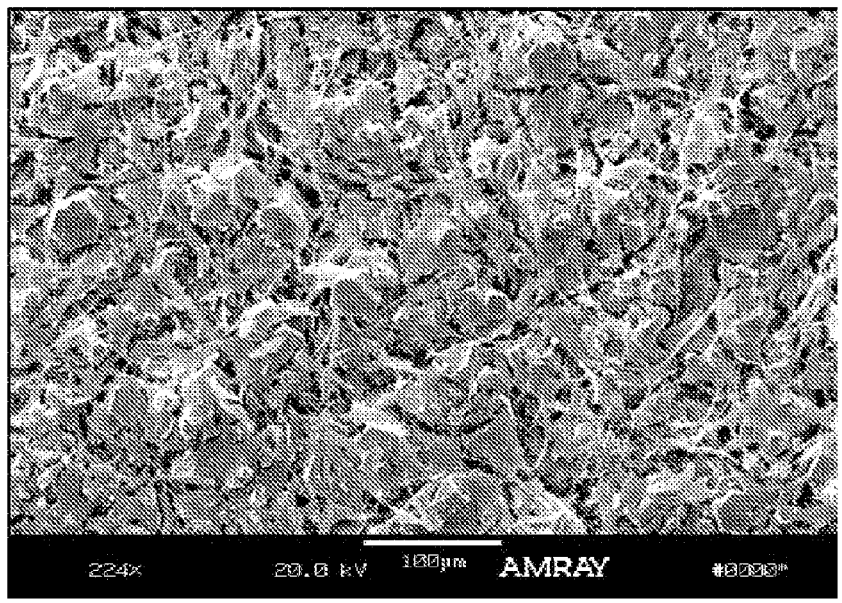
Figure 16D:
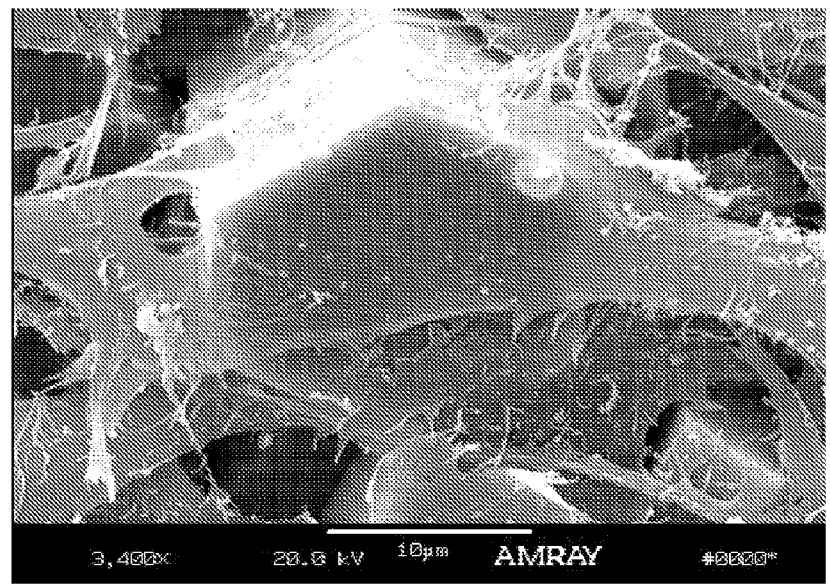

The coating was investigated by a field emission scanning microscope (FESEM, Model DSM 962 Gemini, Carl Zeiss-Leo; Philips XL30 FEG-SEM) on gold-coated samples. Images of hydroxyapatite coatings are found in FIGS. 13-15.

Coatings were additionally deposited on grit blasted substrates at 14 and 26 hours to evaluate the film deposition process. FIGS. 21a-b and 22a-b illustrate the results of XRD analysis of these samples. All 2Theta XRD scans demonstrate that the HA 002 peak, at approximately 25.80, whose intensity in a random sample is 33-40% (PDF 60-9633, 09-0432) of the HA 211 100% peak at 31.70, has a higher absolute intensity than the 211 peak. This suggests that there are more 002 planes diffracting, more c-axis's orthogonal to the substrate surface, than observed in a randomly oriented/textured sample.

002 pole figures for these samples quantify this observation. Nearly all 002 planes are distributed from 0-600 from the substrate's orthogonal in a roughly gaussian manner, with increasing intensity (002 plane population) as the lower psi angles are approached. Further inspection of pole figure data indicates that an increase in the magnitude of or a refinement of the texturing may occur with increasing with synthesis time. From 14 hours to 26 hours, the peak intensity increases steadily from 10,322 a.u. at 50 psi to 13,133 a.u. at 1.00 psi.

Example 7

Biocompatibility of Hydroxyapatite Films

To test the basic biocompatibility of the hydroxyapatite coating, osteoblast adhesion (spreading) was observed by SEM and osteoblast proliferation was quantitatively measured with the CyQuant DNA binding dye. Cell spreading is a qualitative means used to measure the cellular biocompatibility of a surface because cells tend to maximize their surface area in contact with desirable/biocompatible surfaces by spreading out and tend to minimize their surface area in contact with non-biocompatible surfaces by becoming spherical. Cell proliferation is measured to evaluate the surface's ability to maintain a cell population.

Two hydroxyapatite coated samples synthesized for 18.5 hours were used for testing cell adhesion. MC3T3-E1 pre-osteoblast cells were seeded onto the coatings as well as onto tissue culture plastic that served as controls. Cells were incubated at 370 and 5% $CO_2$ in cell media (a-MEM, 10% FBS+ P/S/glu). After 93 hours and 190.25 hours, samples were fixed and prepared for examination by SEM. Three hydroxyapatite coated samples synthesized for 20.5, 18, and 18 hours were used for CyQuant cell proliferation testing. MC3T3-E1 pre-osteoblast cells were seeded onto the samples and onto tissue culture plastic controls. The CyQuant assay was carried out as per kit instructions.

FIGS. 16a-d are representative micrographs of the osteoblast cells on the coating at 93 hours and 190.25 hours. It can be observed that the cells are extensively spread out on the coating surface. In fact, many cells are observed to have increased their cell surface area in contact with the coating to such an extensive degree that the sharp contours of the underlying crystals are seen through the cells. Cell processes can also been seen spanning the troughs between crystals. By comparing the micrographs from 93 hours and 190.25 hours, cell proliferation on the coating can easily be observed qualitatively.

Figure 17:
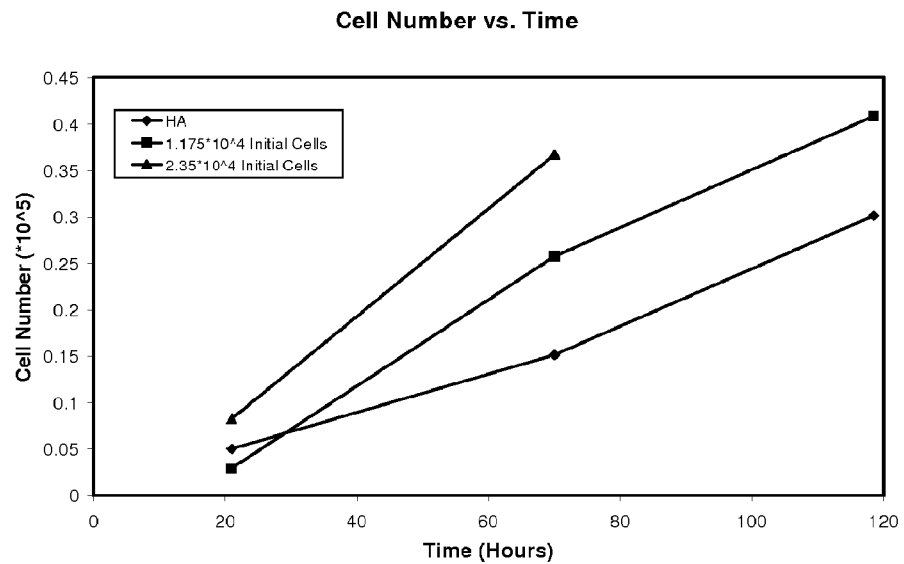
FIG. 17 is a graph showing cell proliferation with CyQuant DNA content as a function of time.

FIG. 17 illustrates the results of the cell proliferation assay. Over the first 70 hours (3 days) osteoblasts proliferate on the HA coating, but at a slower rate than that seen on tissue culture plastic controls. Between 3 and 5 days, however, the proliferation rate is roughly equal on both substrates. It is observed that the cell numbers calculated at 20 hours are systematically less than the seeded density, which is assumed to be due to an error in the dilution series used to make the standard curve. The standard curve for this assay is a straight line, thus, only the absolute cell number is incorrect. As a measure of biocompatibility the results above indicate that the HA coating is indeed biocompatible—osteoblasts actively maximize their surface area in contact with the coating and the coating supports cell proliferation.

Osteoblast Cell Activity

Figure 18:
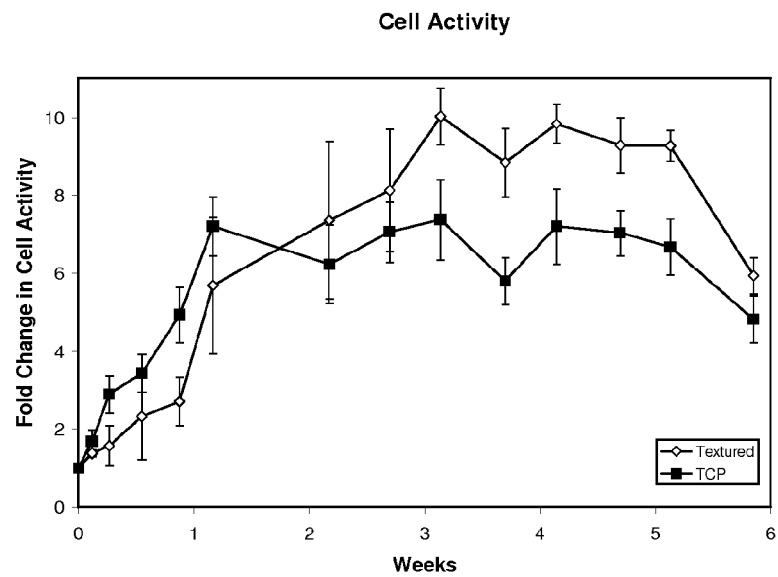
FIG. 18 is a graph comparing cell metabolic activity for hydroxyapatite versus TCP.

Alamar blue, a dye that is reduced by the metabolic intermediates NADPH/NADP, FADH/FAD, FMNH/FMN, and NADH/NAD was used to measure total metabolic activity of cells seeded onto textured HA coatings, randomly oriented HA coatings, and tissue culture plastic (TCP). FIG. 18 demonstrates that cell activity increases slightly slower on textured HA coating than TCP over the first week in culture, on average. However, after week one, activity is higher on textured coatings, and significantly higher from 3-5 weeks in culture. Furthermore, peak activity on HA is almost 36% greater than peak intensity on TCP.

Figure 19:
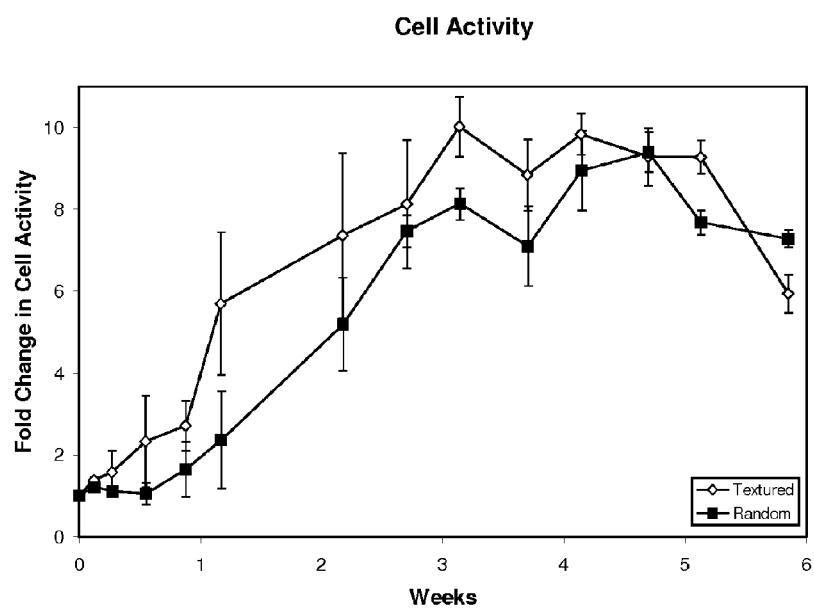
FIG. 19 is a graph comparing the effect of texture on cell metabolic activity.
Figure 20A:
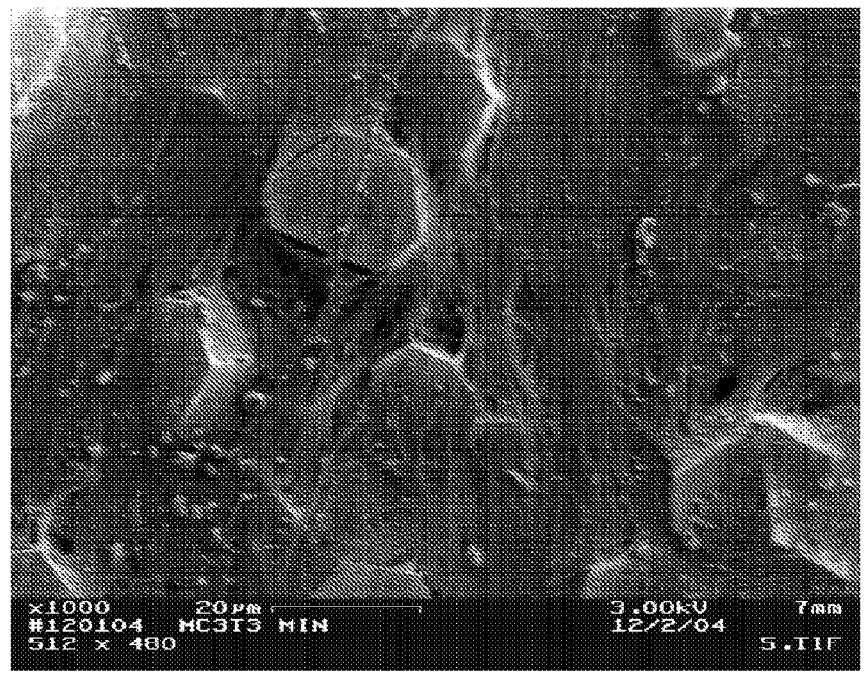
FIGS. 20a-d are scanning electron microscopy images of osteoblast mineralization on hydroxyapatite.
Figure 20B:
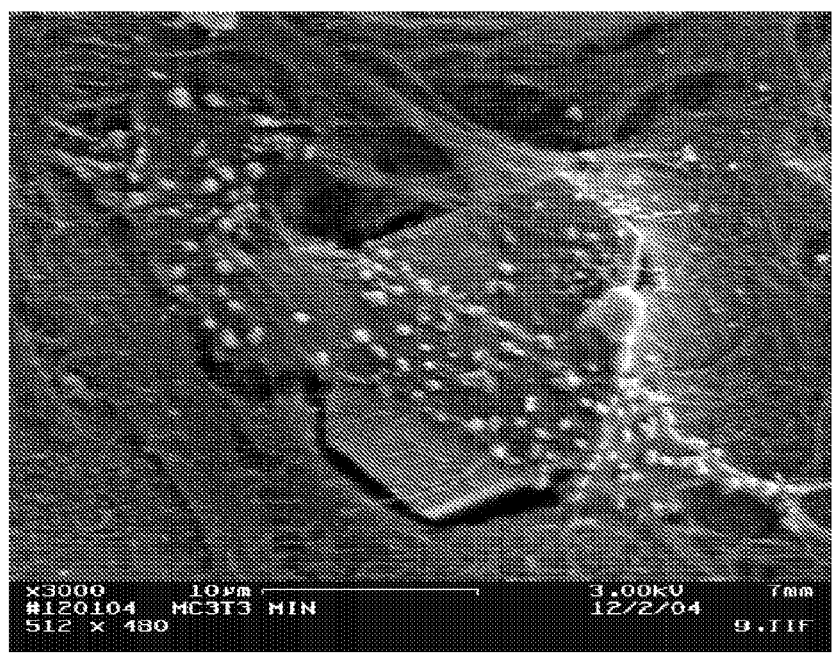
Figure 20C:
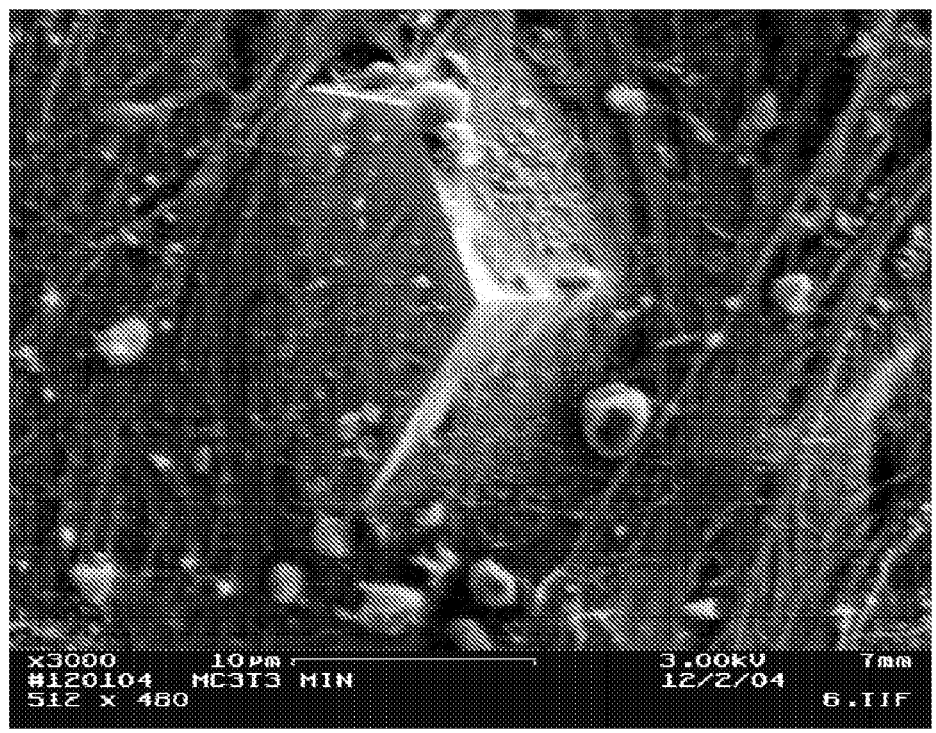
Figure 20D:
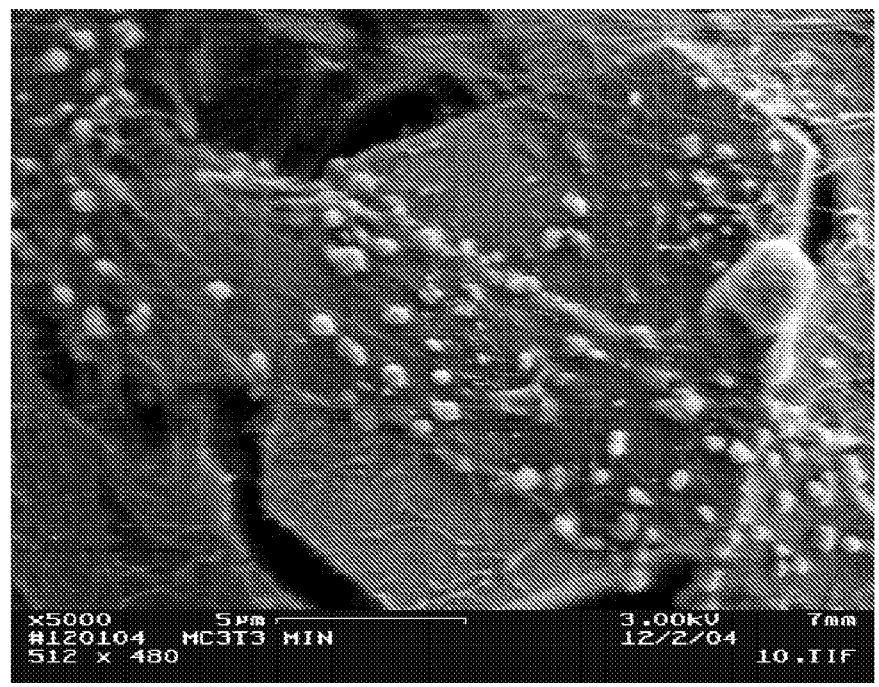
Figure 21A:
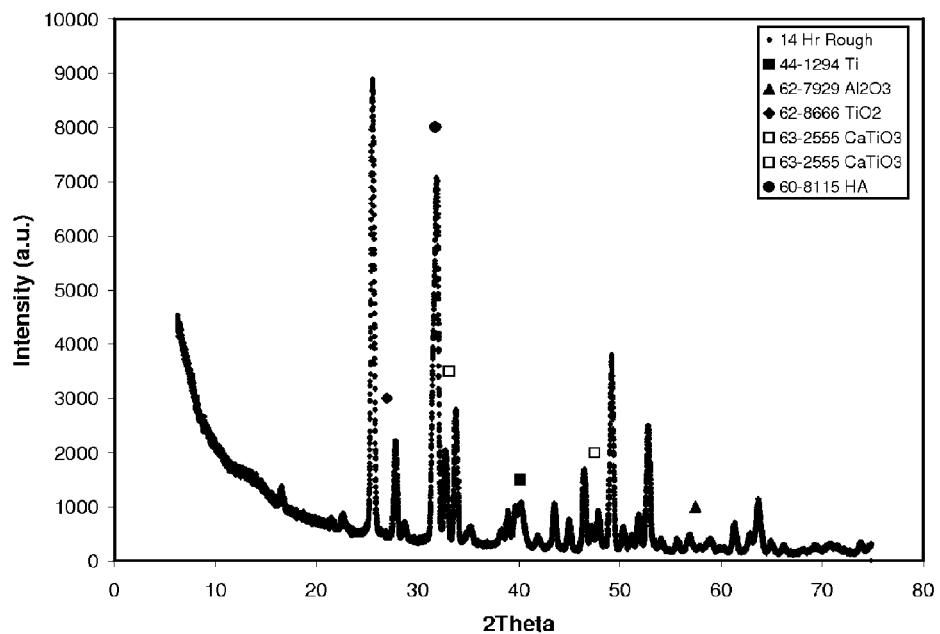
FIG. 21a is an XRD pattern of a hydroxyapatite coating after 14 hours.
Figure 21B:
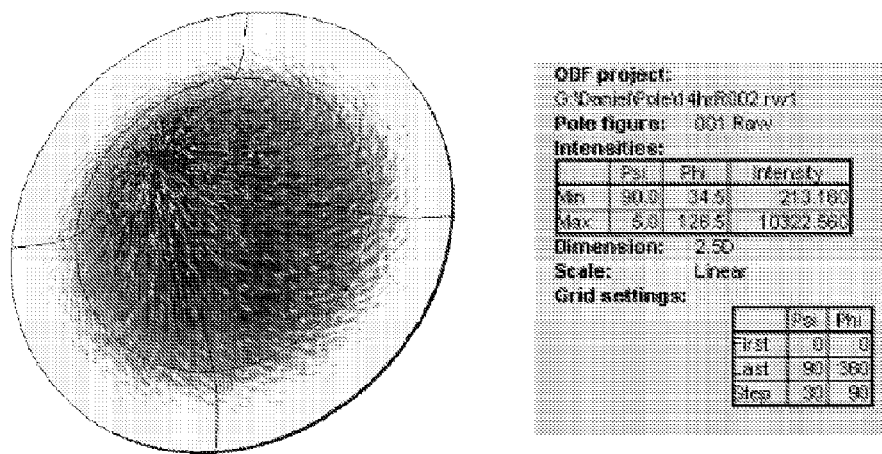
FIG. 21b is a pole figure of a hydroxyapatite coating after 14 hours.
Figure 22A:
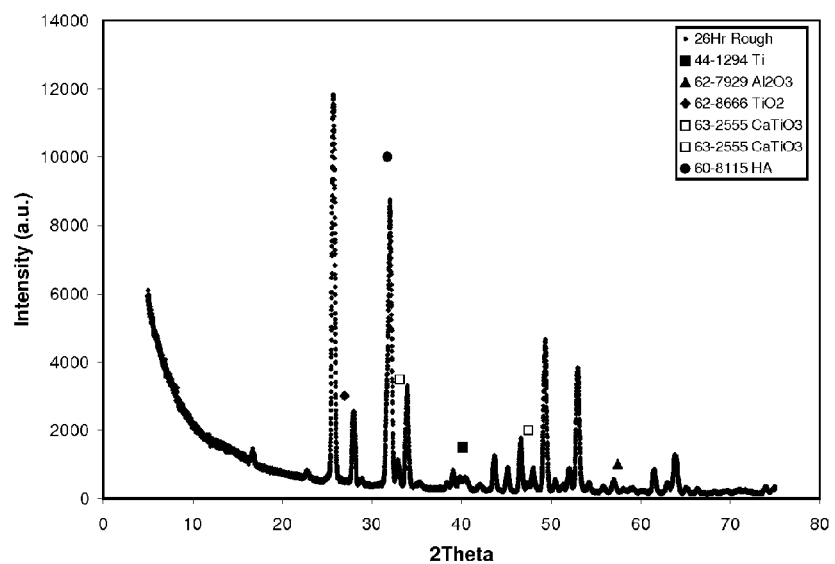
FIG. 22a is an XRD pattern of a hydroxyapatite coating after 26 hours.
Figure 22B:
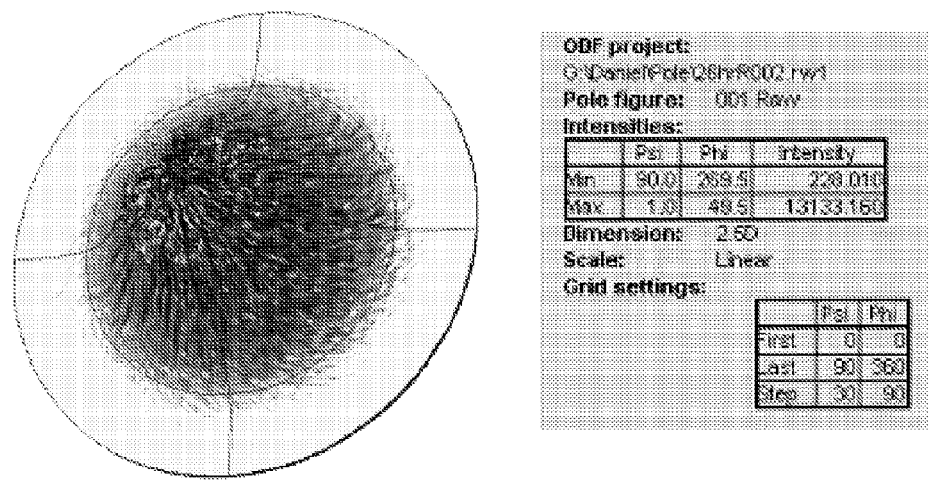
FIG. 22b is a pole figure of a hydroxyapatite coating after 26 hours.

FIG. 19 compares cell activity on textured and randomly oriented samples. For all data points up to nearly five weeks activity is increased on oriented samples as compared to randomly textured samples, including two points where activity is significantly greater. The most prominent difference between the two plots is the 3-4 day period where activity is flat on the randomly oriented substrate. This lag could be due to cells needing additional time to form a proper interface between themselves and the random coating because of differences in protein adhesion to the random surface versus the oriented surface. Regardless, if this is the exact explanation or not, this data illustrates for the first time in an applied system that crystal orientation has, at the very least, a small but significant affect on osteoblast bioactivity.

Osteoblast Mineralization

The ability of the hydroxyapatite coating to facilitate osteoblast differentiation, extracellular matrix product, and matrix mineralization was examined in multi-week cell culture.

A hydroxyapatite coated substrate synthesized for 18 hours was used for testing. MC3T3-E1 pre-osteoblast cells were seeded onto the coating. Two control wells were also seeded with cells. Cells were incubated and induced using 50 mg/mL ascorbic acid and 10 mm beta-glycerol-phosphate in cell media after 3 days in culture. On day 24, the FBS was changed due to a lack of mineralization in control samples. Controls were found to stain positive for alizarin red, a dye used to confirm mineralization, on day 48. On day 48, the HA coated sample was fixed and prepared for examination by SEM. Mineralization was also monitored using a second cell line, CK17 passage 8 OPN −/− pre-osteoblast cells using a coated sample synthesized for 18 hours. An identical procedure was used except D-MEM media was used and the cells were first induced after 7 days. Controls were found to stain positive for alizarin red on day 24. The experiment was ended after 24 days, 17 days after induction.

Mineralization and therefore normal cell differentiation was concluded to successfully have occurred on two different coating samples using two different osteoblast cell lines MC3T3-E1 and CK17. In each case, controls stained positive for mineral as well. FIGS. 20a-d show SEM micrographs of the sample plated with MC3T3-E1 cells after 48 days of incubation (45 days post induction). It can be seen that the cells and their matrix have filled in all the surface topography of the sample.

Example 8

Deposition of Hydroxyapatite Films Over Titanium Substrate

This example reports the first use of EDTA/TEP doubly-regulated hydrothermal crystallization of hydroxyapatite films on multiple substrates. The example explores the kinetics of TEP hydrolysis and the thermodynamics of free calcium concentration and HA phase equilibria, as well as the effect of substrate on the microstructure, thickness, constituent phases, crystallinity, and adhesion of HA films.

Thermodynamic Process Simulation

Thermodynamic phase equilibria models were calculated using thermo-chemical simulation software (OLI Systems, Inc., Morris Plains, N.J.). The fundamental basis for the algorithms used in the software is reported in Lencka and Riman (*Chemistry of Materials* 1993, 5, 61-70). HA thermodynamic phase equilibria models for the $CaO-P_2O_5-NH_4NO_3-H_2O$ chemical system are reported in Riman et al. (*Solid State Ionics, Diffusion & Reactions* 2002, 151, 393-402.)

Experimental conditions for hydrothermal crystallization of HA films in the $Ca(NO_3)_2$-EDTA-TEP-KOH—$H_2O$ chemical system were chosen based upon calculated phase boundaries of the $Ca(NO_3)_2$-EDTA-$H_3PO_4$— KOH—$H_2O$ system in the presence of titanium, 316 stainless steel (Fe—Cr—Ni), and Co—Cr at 200° C. These metals were considered representative of the substrates used in this work ($Ti_6A_{14}V$, grit blasted $Ti_6A_{14}V$, Ti, 316 stainless steel, $Co_{28}Cr_6Mo$, see below), which were chosen based on their current or prior use in clinical load bearing orthopedic applications. The software database does not contain TEP because there is no reported thermodynamic data for TEP in the literature. Thus, $H_3PO_4$ was utilized in its place for thermodynamic calculations. The use of this acid allows the model to account for products of TEP hydrolysis, $PO_4^{3-}$ and $3H^+$, without the explicit use of TEP. This substitution was justified by reviewing the phosphate chemical species calculated to be present at 200° C. in the 0.232 molal $Ca(NO_3)$-0.232 molal EDTA-0.187 molal $H_3PO_4$-1.852 molal KOH—Ti—$H_2O$ chemical system. The data demonstrated that $H_3PO_4$ is calculated to have a concentration of less than $1*10^{-10}$ molal at 200° C., which indicates that $H_3PO_4$ "releases" free phosphate and is a reasonable model for TEP at 200° C. TEP kinetics results, reported below, indicate that complete hydrolysis occurs at 180° C., which validates the substitution of $H_3PO_4$ for TEP in the model at 200° C. The third product of TEP hydrolysis, $C_2H_5OH$, was ignored due to its dilute state in the solution, 0.561 molal, after full TEP hydrolysis. This omission was justified by comparing the phase diagrams of the 0.232 molal $Ca(NO_3)$-0.232 molal EDTA-0.187 molal $H_3PO_4$-1.852 molal KOH—Ti—$H_2O$ chemical system and the 0.232 molal $Ca(NO_3)$-0.232 molal EDTA-0.187 molal $H_3PO_4$-0.561 molal $C_2H_5OH$-1.852 molal KOH—Ti—$H_2O$ chemical system at 200° C. A comparison of the two diagrams demonstrated no differences in the position of phase boundaries at pH relevant to the work in this study. After the creation of phase diagrams the specific pH/$Ca^{2+}$ combination for the 0.232 molal $Ca(NO_3)_2$-0.232 molal EDTA-0.187 molal $H_3PO_4$-1.852 molal KOH—$H_2O$ chemical system used for synthesis in this paper, see below, in the presence of each substrate at 200° C. was calculated and plotted on each respective diagram.

TEP Hydrolysis Kinetics and Reactor Heating Dynamics

To characterize the release of phosphate ions from TEP, model mixtures containing KOH (Fisher Scientific Hampton, N.H.) and TEP (Sigma Aldrich, St. Louis, Mo.) were prepared. KOH and TEP were dissolved in de-ionized water at the same concentrations used for synthesis, see below, and loaded into a 1 L stirred Teflon®-lined autoclave (Model 4531, Parr Instruments, Moline, Ill.). The autoclave was equipped with a needle valve with dip tube that allowed sampling at elevated pressure and temperature. Excess calcium nitrate tetrahydrate (Fisher Scientific) was added to samples of reaction products of TEP hydrolysis taken from the reactor at various temperatures to monitor free phosphate formation. The solution was filtered and assayed for the presence of Ca—P precipitate. To evaluate the heating rate of the reaction solution autoclave heating dynamics were investigated by directly placing K-type thermocouples into 125 mL Parr 4731 autoclaves filled with a model non-volatile liquid, technical grade glycerol. Autoclaves were placed in an oven pre-heated to 200° C. and internal changes in temperature were monitored with time. Heating dynamics were compared to TEP hydrolysis kinetics to determine the reaction time above which uncomplexed $PO_4^{3-}$ was available for formation of HA.

Equilibrium $Ca^{2+}$ Concentration

Equilibrium $Ca^{2+}$ concentrations were calculated using commercial thermo-chemical simulation software referred to previously (OLI Systems, Inc.). The equilibrium concentration of $Ca^{2+}$ was calculated for temperatures from 25-180° C. in the 0.232 molal $Ca(NO_3)_2$-0.232 molal EDTA-1.852 molal KOH—$H_2O$ system in the presence of Ti. This model predicts the concentration of $Ca^{2+}$ prior to complete TEP hydrolysis (see below). Due to the absence of TEP in the software database (see above) the results from the model do not take into account the products of partial TEP hydrolysis, $2H^+$ and $2C_2H_5OH$. The omission of $C_2H_5OH$ is justified in section a (Thermodynamic Process Simulation), above. The omission of $2H^+$ is justified by comparing the pH calculated for the 0.232 molal $Ca(NO_3)_2$-0.232 molal EDTA-1.852 molal KOH—Ti—$H_2O$ system at 180° C. (pH=10.91) and the 0.232 molal $Ca(NO_3)_2$-0.232 molal EDTA-0.187 molal $H_3PO_4$-1.852 molal KOH—Ti—$H_2O$ at 180° C. (pH=10.6). A comparison of the pH of each solution demonstrates that the addition ~0.561 molal of $H^+$ from the dissociation of $H_3PO_4$, nominally TEP, at 180° C. minimally changes the pH of the solution. For comparison, the concentration of $Ca^{2+}$ was calculated for temperatures from 25-160° C. (initial HA deposition temperature) in the 0.05 molal $Ca(EDTA)^{2-}$-0.05 molal $NaH_2PO_4$—NaOH—$H_2O$—Ti hydrothermal synthesis system, demonstrated by Fujishiro et al. to form phase pure HA 38. Equilibrium $Ca^{2+}$ concentrations at the initial HA deposition temperature of the system presented here, 180° C. (see below), and the system reported by Fujishiro et al., 160° C., were compared to evaluate the thermodynamic effect of pH and temperature on uncomplexed $Ca^{2+}$ concentration and to predict/explain morphological differences between the two films.

Film Synthesis

Metal substrates ($Ti_6A_{14}V$, grit blasted $Ti_6A_{14}V$, Ti, 316 stainless steel, $Co_{28}Cr_6Mo$) were chosen based on their current or prior use in clinical load bearing orthopedic applications. The choice of substrates enabled an investigation of the ability of the crystallization process to uniformly coat substrates with various chemistries and surface roughnesses with HA. The choice of substrates also enabled an investigation of the effect of crystallography on HA deposition —$Ti_6A_{14}V$, grit blasted $Ti_6A_{14}V$, Ti, and $Co_{28}Cr_6Mo$ have hexagonal crystal lattices and 316 stainless steel has a cubic lattice.

Prior to synthesis, 1 in diameter rods of $Ti_6A_{14}V$ alloy (ASTM-B348 Grade 5, McMaster Carr, Dayton, N.J.), titanium (98.9% pure, ASTM-B348 Grade 2, McMaster Carr), 316 stainless steel (ASTM-A276, McMaster Carr), and $Co_{28}Cr_6Mo$ alloy (ASTM-F75, Stryker Orthopaedics, Mahwah, N.J.) were cut into discs, 1 in (diameter)×⅛ in (thickness), and used as substrates. Where indicated, $Ti_6A_{14}V$ alloy substrates were grit blasted using 35-100 $Al_2O_3$ media (McMaster Carr) to roughen the surface. Grit was removed by cleaning in an ultrasonic bath (FS30, Fisher Scientific). All substrates, titanium foil (0.127 mm, 99.7%, Sigma-Aldrich) substrate holders, and Teflon®reaction vessel liners (125 mL, Parr Instrument) were cleaned with Citronox detergent (Alconox, White Plains, N.Y.), acetone (Fisher Scientific), ethyl alcohol (Pharmco-AAPER, Brookfield, Conn.), and deionized water and dried in a 60° C. oven prior to synthesis.

Aqueous stock solutions of 0.232 molal calcium nitrate tetrahydrate, $Ca(NO_3)_2 \cdot 4H_2O$ (99.38%, Fisher Scientific), 0.232 molal ethylenediamine-tetraacetic acid (EDTA), $C_{10}H_{16}N_2O_8$ (99.4%, Fisher Scientific), 0.187 molal triethyl phosphate (TEP), $C_6H_{15}O_4P$ (99.8+%, Sigma Aldrich), and 1.852 molal potassium hydroxide, KOH (89.3%, Fisher Scientific) were used for hydrothermal reactions and prepared as follows: Calcium nitrate tetrahydrate, EDTA, and TEP were mixed together and dissolved in deionized $H_2O$. In a second container KOH was dissolved in deionized $H_2O$. Once dissolved, the KOH solution was placed in a cold-water bath to cool to room temperature. When cool, the KOH solution was added to the former solution and stirred until visible particulates had dissolved. The stock solution was then filtered (220 nm pore size, Nalgene, Rochesrter, N.Y.) and stored in a tightly sealed container.

Figure 23:
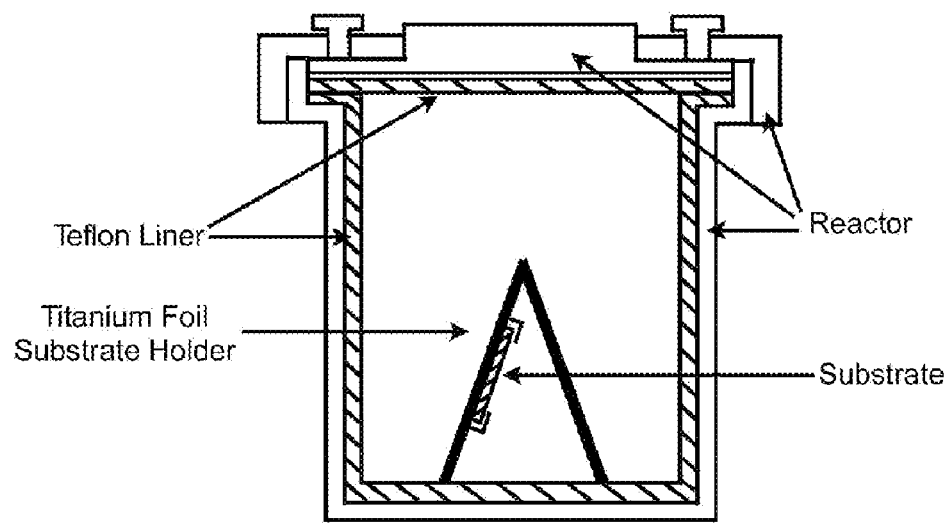
FIG. 23 is a cross-sectional diagram Parr (Model 4731) reactor.

The typical hydrothermal reaction was conducted as follows: The substrate was fixed in the substrate holder and placed inside a 125 ml Teflon®-lined reaction vessel (4731 reactor, Parr Instrument). The substrate holder placed the sample in a position that inhibited the settling of homogeneously formed nuclei onto the surface by means of gravity (FIG. 23). Stock solution, 70 mL, was added to the reaction vessel, which was then sealed. The reactor was then placed in an oven pre-heated to 200° C. for 24 hours. The reactor was removed from the oven and allowed to cool to room temperature in air. The substrate was removed from the reactor and rinsed for several minutes in running tap water and then in deionized water. The sample was then placed in a 60° C. oven to dry.

Substrate and Film Characterization

A profilometer (scan length 500 μm, Dektak 3030, Veeco, Woodbury, N.Y.) was used to measure the surface roughness, Ra, of each substrate. Field emission scanning electron microscopy (FESEM) (DSM 982 Gemini, Carl Zeiss, Oberkochen, Germany) was used to examine the bare substrate and film microstructure in cross-section, top-on, and after adhesion experiments. Cross sectional samples were prepared by cutting two cross-sections from each substrate-film sample with a diamond saw (Vari/Cut VC-50, Leco Corporation, St. Joseph, Mich.). These were then embedded face-to-face in epoxy (SPI-PON® Epoxy Embedding Kit, SPI Supplies, West Chester, Pa.), polished until substrates achieved a mirror finish, and sputter coated with a conducting 25 nm Au/Pd film (Balzers SCD 004, OC Oerlikon Balzers AG, Balzers, Liechtenstein). Film thickness was computed by direct measurement of the thickness of FESEM cross-sections at 22 μm intervals (10 points) along the length of the micrograph using commercial image analysis software. Grain diameter was determined by direct measurement of 10 randomly selected grains shown in top-on FESEM micrographs using commercial image analysis software. Average film thickness, average grain diameter, and the standard deviation of the means were calculated using Excel (Microsoft, Redmond, Wash.). A two-tailed, heteroscedastic t-test was used to determine if differences in grain diameters were significant ($\alpha$=0.5, Microsoft Excel). An estimate of grain aspect ratio was calculated by dividing average film thickness by average grain diameter. The calculation assumes that grains run continuously from the substrate surface to the film surface. X-ray diffraction (XRD) (step size=0.005°, 1 step/sec, 45 KV, 40 mA, Ni-filtered $CuK_\alpha$ radiation, parallel beam optics, Philips Hi-Resolution X'PERT X-Ray Diffractometer, PANalytical B.V., Almelo, Netherlands) was used to determine the phases present in the films and the substrate. XRD patterns from $Co_{28}Cr_6Mo$ and 316 stainless steel substrates were obtained using an additional graphite diffracted beam monochromator (PANalytical B.V.) to remove background fluorescence. Experimental XRD patterns were matched to patterns in the Powder Diffraction File (PDF, ICDD, Newtown Square, Pa.) database using Jade 6.5 software (MDI, Livermore, Calif.). Subsequent to curve fitting (Jade 6.5, MDI), the crystallinity of hydroxyapatite was calculated by comparing the area of HA crystalline peaks in the range 28-35° and of the amorphous calcium-phosphate (ACP) hump centered at approximately 30-31° (2θ) using the following equation:

$$X\% = \left[\frac{\sum_{i=1}^{c} A_c}{\left(\sum_{i=1}^{c} A_c + \sum_{i=1}^{a} A_a\right)}\right] * 100\% \quad (4)$$

where, $\Sigma A_c$ is the sum of the areas under all the HA crystalline peaks and $A_a$ is the sum of the area under the ACP hump. Peak intensities were also used to calculate HA (0002)/(21$\bar{3}$1) peak ratios. Peak de-convolution was used to determine (21$\bar{3}$1) peak intensity due to the overlapping peak profiles of the (21$\bar{3}$1) and (11$\bar{2}$2) peaks in the HA profile (Jade 6.5). The adhesion of the film to the substrate was measured using the ASTM (American Society for Testing and Materials, West Conshohocken, Pa.) standard D3359-02 tape test A. Adhesion was rated on a scale of 0-5 with 5 representing no peeling and 0 representing complete removal, as specified by ASTM. Four measurements were averaged and reported for each film. For comparison purposes, Metalastic DTM Acrylic Modified Enamel (Cleveland, Ohio, Sherwin Williams) with an ASTM D3359 adhesion rating of 5 and Industrial Shop Primer (Gardnerville, Nev., Aervoe Industries Incorporated) with an ASTM D3359 adhesion rating of 3 were used as standards.

Thermodynamic Process Simulation

Figure 24:
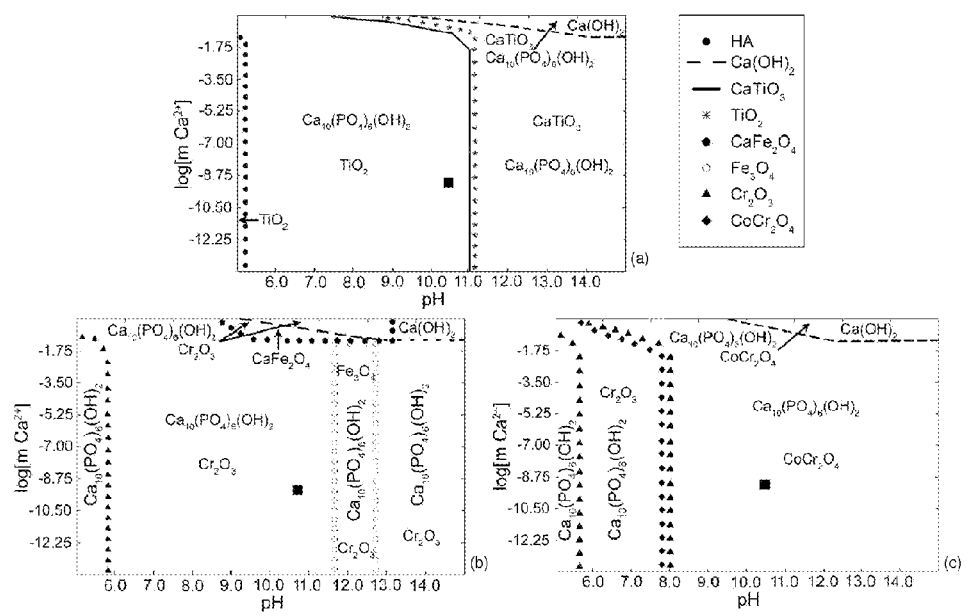
FIG. 24 is a calculated thermo-chemical phase equilibria diagram for the 0.232 molal $Ca(NO_3)_2$-0.232 molal EDTA-0.187 molal $H_3PO_4$-1.852 molal KOH—$H_2O$ chemical system at 200° C. in the presence of various substrates (a) Titanium, (b) 316 Stainless steel, (c) Co—Cr.

Computed phase stability diagrams for the $Ca(NO_3)_2$-EDTA-$H_3PO_4$—KOH—$H_2O$ system in the presence of titanium, 316 stainless steel, and Co—Cr substrates at 200° C. are shown in FIG. 24. The diagrams illustrate a wide stability range for HA under these conditions. The diagrams also illustrate that titanium, 316 stainless steel, and Co—Cr substrates are not thermodynamically stable, leading to the formation of oxides. The specific pH/[$Ca^{2+}$] point for the 0.232 molal $Ca(NO_3)_2$-0.232 molal EDTA-0.187 molal $H_3PO_4$-1.852 molal KOH—$H_2O$ system in the presence of each respective substrate is marked. For each substrate the pH/[$Ca^{2+}$] data point lies in a region where both an oxide and hydroxyapatite are stable. These diagrams demonstrate that the formation of Ca—P (calcium-phosphate) phase pure HA is thermodynamically favored in the presence of all substrates under these reaction conditions, and confirm the stability of HA in alkaline solutions.

TEP Kinetics

Figure 25:
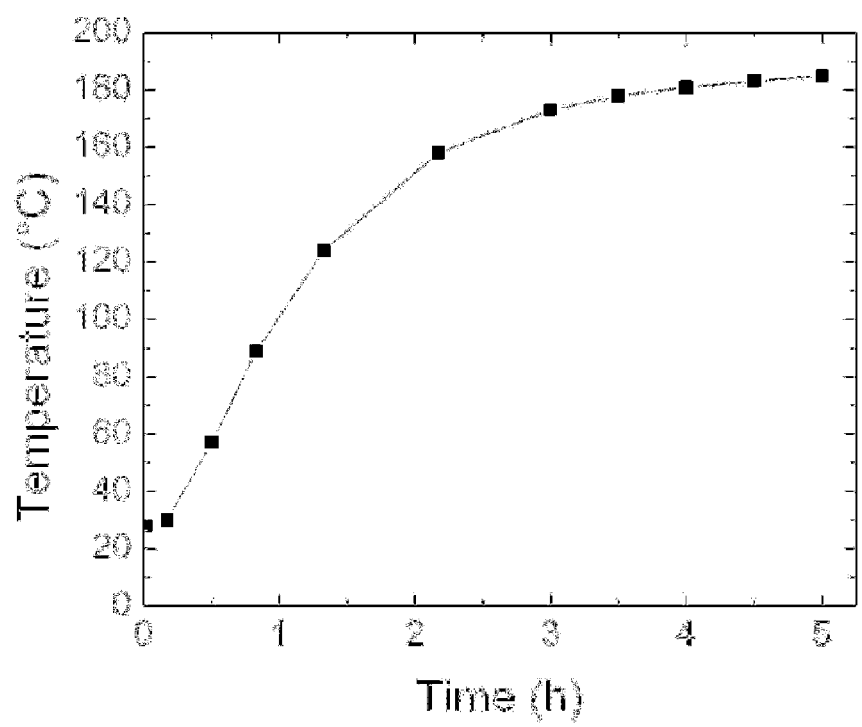
FIG. 25 presents autoclave heating dynamics of an oven pre-heated to 200° C. and filled with a model non-volatile liquid, technical grade glycerol.

TEP hydrolysis kinetics were examined under alkaline hydrothermal conditions. Results revealed that Ca—P particles precipitated in samples taken from solutions with temperatures above 180° C., after the addition of excess calcium nitrate. This agrees with hydrolysis results from the literature, which suggest that temperatures above 110° C. are needed to hydrolyze the second and third ethyl groups in basic solutions. The heating dynamics for the autoclave used in this study were also examined. Heating from room temperature to 180° C. was observed to take 4 h (FIG. 25). Thus, the use of TEP necessitates a two-step film deposition process. The first step, which occurs between 0-4 hours, encompasses the heating of the reaction mixture from room temperature to 180° C. During this step incomplete TEP hydrolysis and the absence of free phosphate ions exclude the possibility of HA crystallization. In the second step, after 4 hours, the autoclave is heated from 180° C. to the final isothermal temperature of 200° C., complete TEP hydrolysis occurs, and free phosphate is available for the formation of HA.

Equilibrium $Ca^{2+}$ Concentration

Figure 26:
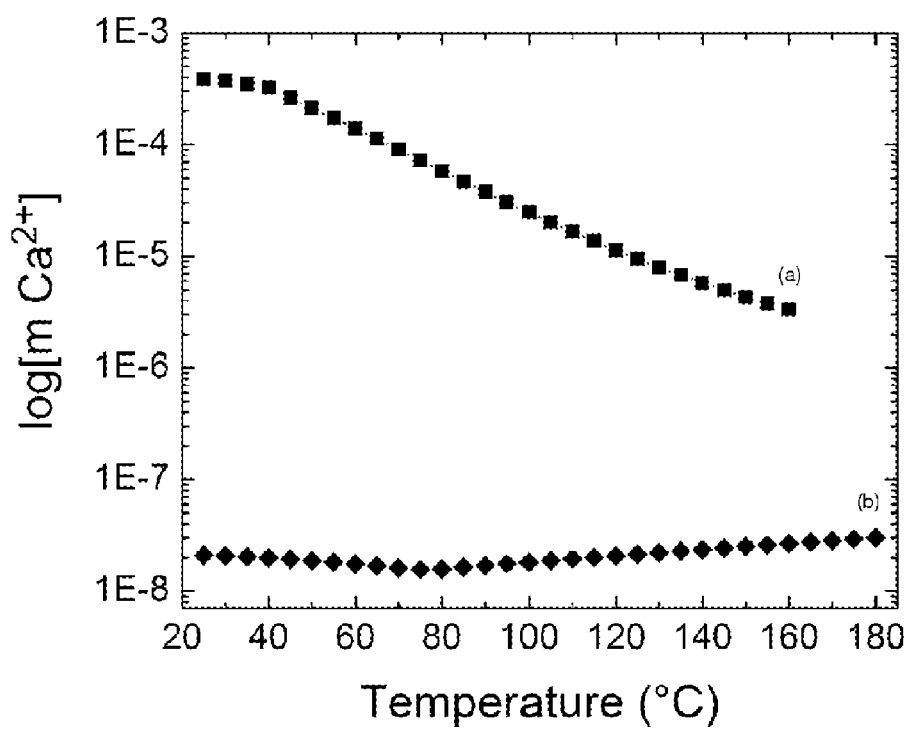
FIG. 26 presents thermo-chemical modeling of $Ca^{2+}$ concentration (m=molal) versus temperature as a function of ionic calcium species in a hydrothermal reaction solution containing (a) 0.05 molal $CaCl_2$-0.05 molal $Na_2H_2EDTA$-0.05 molal $NaH_2PO_4$—NaOH—$H_2O$ (b) 0.232 molal $Ca(NO_3)_2$-1.852 molal KOH-0.232 molal EDTA-$H_2O$ both in the presence of titanium.

The equilibrium concentration of uncomplexed $Ca^{2+}$ in the 0.232 molal $Ca(NO_3)_2$-1.852 molal KOH-0.232 molal EDTA-Ti reaction mixture used in this study is displayed in FIG. 26. When phosphate is first available from TEP hydrolysis at 180° C. (see above), the model calculates an uncomplexed $Ca^{2+}$ concentration of $3.02*10^{-8}$ molal at a pH of 10.91. For comparison, the concentration of uncomplexed $Ca^{2+}$ in the 0.05 molal $Ca(EDTA)^{2-}$-0.05 molal $NaH_2PO_4$—NaOH—$H_2O$—Ti hydrothermal synthesis system, demonstrated by Fujishiro et al. to form phase pure HA in this system, was modeled (Fujishiro, Y.; Fujimoto, A.; Sato, T.; Okuwaki, A. *Journal of Colloid and Interface Science* 1995, 173, 119-127). Thermochemical modeling of the system reported by Fujishiro et al. predicts an uncomplexed $Ca^{2+}$ concentration of $3.31*10^{-6}$ molal at their initial HA deposition temperature and pH, 160° C., pH 6. Results demonstrate that Fujishiro et al.'s system has a two order of magnitude greater concentration of uncomplexed $Ca^{2+}$ than the system reported here, at each system's respective initial HA deposition temperature. The concentration of calcium precursor used in the study reported here, however, is nearly 5-fold greater than the concentration of calcium precursor used by Fujishiro et al. The explanation for this result is pH. The literature has reported that increasing the pH of a solution decreases the ability of the Ca-EDTA$^{2-}$ complex to dissociate. At 180° C. the pH of the solution used in this study is thermodynamically calculated to be 10.91, at 160° C. the pH of Fujishiro et al.'s solution is 6. Thus, by using EDTA$^{4-}$, increasing pH, and having a lower concentration of uncomplexed $Ca^{2+}$ this synthesis process should favor crystal growth over crystal nucleation resulting in films that have a characteristic shape, and high crystallinity. In addition, multiple authors have reported that the length and/or aspect ratio of HA crystals formed in solution by non-stirred homogeneous precipitation using EDTA are a function of $Ca^{2+}$ concentration together with $PO_4^{3-}$ concentration, EDTA/Ca ratio, temperature, and pH, indicating that a variation in grain aspect ratio should be expected from that reported elsewhere.

Substrate Characterization

Figure 27:
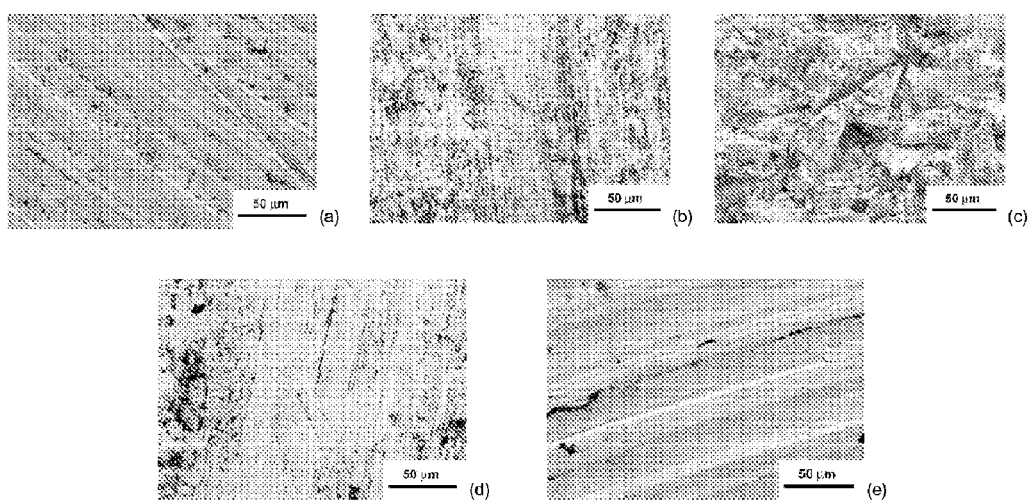
FIG. 27 presents scanning electron micrographs of various substrates before hydrothermal treatment. (a) $Ti_6A_{14}V$, (b) Ti, (c) Roughened $Ti_6A_{14}V$, (d) 316 Stainless Steel, (e) $Co_{28}Cr_6Mo$ alloy (Magnification ×500).
Figures 28, 29:
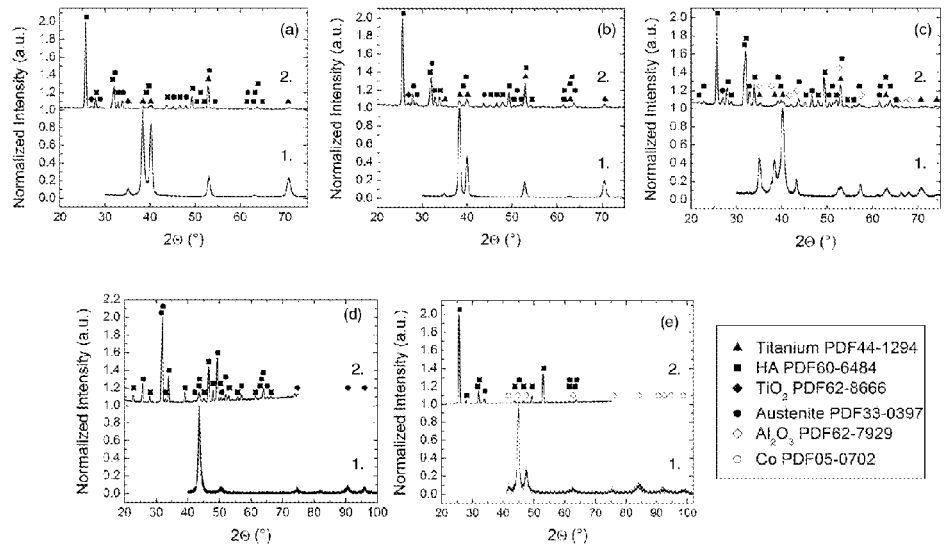
FIG. 28 presents X-ray diffraction patterns of various substrates before and after hydrothermal treatment for 24 h at 200° C. (a) $Ti_6A_{14}V$, (b) Ti, (c) Roughened $Ti_6A_{14}V$ (d) Stainless Steel, (e) $Co_{28}Cr_6Mo$ alloy. For each substrate: (1) pre-hydrothermal treatment, (2) post-hydrothermal treatment.
FIG. 29 presents substrate roughness, phase, and relevant XRD peak ratios data.

FIGS. 27 and 28 display complementary scanning electron micrographs and X-ray diffraction patterns of $Ti_6A_{14}V$, Ti, roughened $Ti_6A_{14}V$, stainless steel, and $Co_{28}Cr_6Mo$ substrates prior to hydrothermal treatment. SEM micrographs demonstrate that all non-roughened substrates lack distinct features or topography except for periodic polishing marks. The grit-blasted $Ti_6A_{14}V$ substrate, on the other hand, has an irregular crevassed surface with numerous pits of different sizes and shapes. These differences in surface topography are reflected in the profilometer surface roughness results reported in FIG. 29. Phase analysis of XRD patterns, reported in FIG. 29, confirm the expected identity of each material. Corundum is found in the roughened Ti substrate due to the use of $Al_2O_3$ media, and its implantation into the substrate during the grit-blasting process.

This finding is in agreement with other authors using the same roughening technique. Peak ratio texture analysis results are reported in FIG. 29 as well. Through comparison with Powder Diffraction File standards it can be concluded that all substrates display some degree of preferred crystallographic orientation.

Film Phase and Crystallinity

FIG. 28. displays X-ray diffraction patterns of films deposited on $Ti_6A_{14}V$, Ti, roughened $Ti_6A_{14}V$, stainless steel, and $Co_{28}Cr_6Mo$ substrates after hydrothermal treatment. Phase analysis confirms that HA is the only Ca—P phase formed on each substrate. The films formed on the $Ti_6A_{14}V$, Ti, and roughened $Ti_6A_{14}V$ also display a small peak at 26.98° that is at the same position of the 100% $TiO_2$ (110) peak. All films were calculated to have crystallinity indexes of 99% because no ACP hump was identified by the analysis software for any sample as presented in FIG. 30. The lack of an amorphous hump made any affect of preferred orientation, see below, on peak areas and, thus, the crystallinity calculation moot. Nonetheless, a crystallinity index less than 100% is reported due to the inherent error in the calculation. These results demonstrate that the hydrothermal crystallization process presented here deposits highly crystalline, Ca—P phase pure HA regardless of substrate chemistry, crystallography, or surface roughness (FIGS. 27-30). Phase pure, high crystallinity HA is a requirement of next generation HA films due to the lower solubility and higher bone apposi-tion percentages that have been reported for HA coatings with increasing chemical stability.

Film Morphology and Orientation

Figures 30, 31:
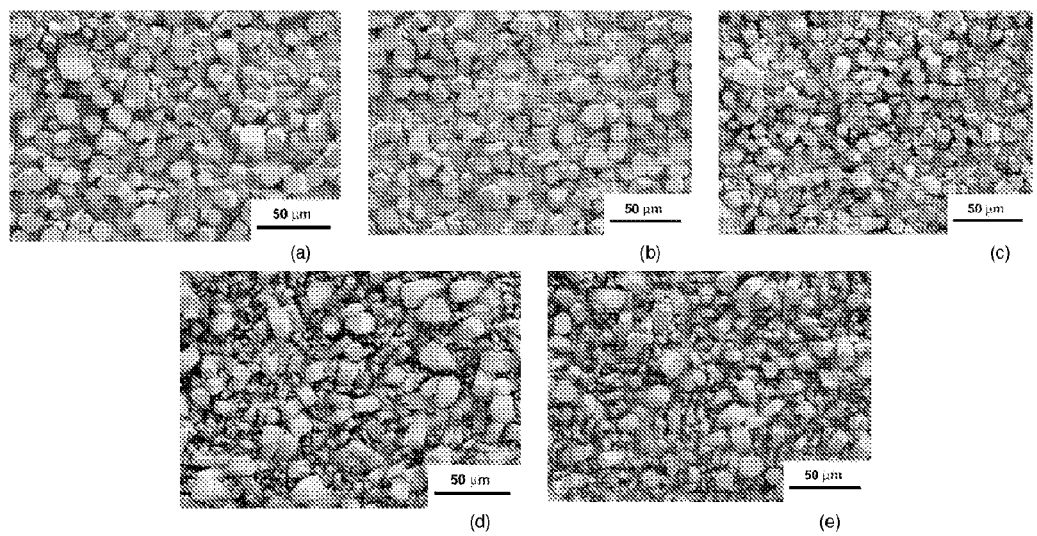
FIG. 30: presents deposited film crystallinity, (0002)/(21$\overline{3}$1) peak ratio, particle size, thickness, and adhesion rating data.
FIG. 31 presents scanning electron micrographs of films deposited on various substrates after hydrothermal treatment for 24 h at 200° C. (a) $Ti_6A_{14}V$, (b) Ti, (c) Roughened $Ti_6A_{14}V$, (d) Stainless Steel, (e) $Co_{28}Cr_6Mo$ alloy (Magnification ×500).

FIG. 31 displays scanning electron micrographs of films deposited on $Ti_6A_{14}V$, Ti, roughened $Ti_6A_{14}V$, stainless steel, and $Co_{28}Cr_6Mo$ substrates after hydrothermal treatment. Deposited films are composed of uniform hexagonally faceted grains that appear to have grown perpendicular to the substrate surface on all substrates. The hexagonal prism is one of the idealized forms of crystals in HA's 6/m crystal class. The formation of grains of this type indicates that these films form through a low energy growth controlled process. This HA morphology is important biologically as it known to display crystallographic faces that bind bone proteins and bone protein amino acid sequences with high affinity.

Average grain diameter and grain diameter uniformity are observed to vary from titanium-based substrates, 12+/−4 μm, to non-titanium substrates, 8+/−5 μm (FIGS. 30-31). t-test analysis of results demonstrate, however, that differences are not significant for α=0.05. From this result it may be concluded that substrate chemistry and surface roughness do not play a significant role in grain nucleation and growth. Average grain diameters are larger than elsewhere in the literature, and 3-4 fold larger than those reported by Fujishiro et al., at the synthesis conditions modeled above. Assuming that grains are continuous from the substrate surface to the film surface, a rough estimate of grain aspect ratio of 1-2 may be calculated by comparing average grain diameter to average film thickness, reported below, for each substrate. Grain aspect ratios for HA films reported elsewhere in the homogeneous precipitation hydrothermal literature are on the order of 10. Thus, it may be concluded that the synthesis conditions reported here compose a novel set that enable the growth of near equiaxed grains of HA.

X-ray diffraction peak ratio texture analysis results report (0002)/(21 $\bar{3}$ 1) HA peak ratios that are larger than what is predicted for randomly oriented grains, 0.28, by the Powder Diffraction File, for films formed on all substrates (FIGS. 28 and 30). From these results it may be concluded that hexagonal grains within all HA films are preferentially oriented with respect to the (0002) crystallographic plane regardless of substrate. Peak ratios vary from 0.66 to greater than 100 (FIG. 30), however, it is not appropriate to draw conclusions from these differences. Peak ratio texture analysis is a qualitative technique used to determine the presence or lack or crystallographic texture in a sample, not the degree of texture. Techniques such as X-ray diffraction pole figures are required to determine the degree of texture. In a follow-up manuscript we will report detailed time elapsed XRD, SEM, and X-ray pole figure analysis of crystallographic orientation evolution on alloyed titanium with 6 wt. % aluminum and 4 wt. % vanadium ($Ti_6A_{14}V$) substrates as a function of hydrothermal reaction time.

Analysis of substrate XRD patterns report that $Ti_6A_{14}V$, grit blasted $Ti_6A_{14}V$, Ti, and CoCrMo substrates have (0002) crystallographic orientation and hexagonal crystal lattices (FIGS. 28-29). Because HA also has a hexagonal crystal lattice, these results, together with the results of HA film preferred orientation analysis (FIGS. 28-29), suggests that (0002) HA crystallographic orientation is due to epitaxy. The film formed on the non-hexagonal non-(002) oriented 316 stainless steel, however, has a (0002)/(21 $\bar{3}$ 1) ratio larger than the value reported in PDF 60-6484. Thus, it may be concluded that the source of grain orientation is not epitaxy, but instead a process such as competitive growth, which also results in preferentially oriented films. This conclusion agrees with results from the hydrothermal literature that also report larger than predicted (0002)/(21 $\bar{3}$ 1) HA peak ratios for films formed on non-hexagonal iron and alumina after hydrothermal treatment.

Passivation

Figure 32:
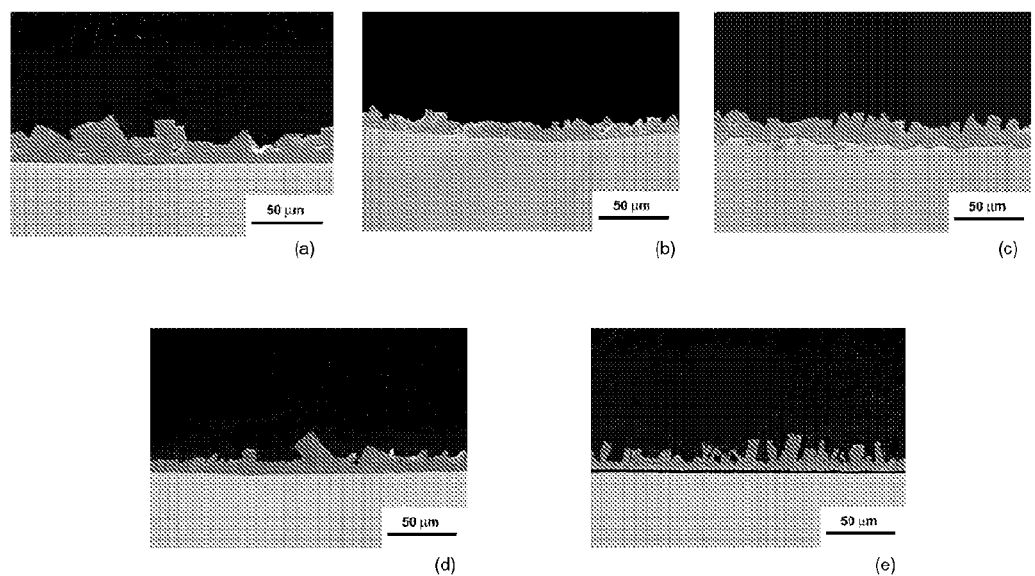
FIG. 32 presents scanning electron micrographs of the cross-sections of films deposited on various substrates after 24 h of hydrothermal treatment at 200° C. (a) $Ti_6A_{14}V$ (b) Ti (c) Roughened $Ti_6A_{14}V$ (d) Stainless Steel (e) $Co_{28}Cr_6Mo$ alloy (Magnification ×500).

Scanning electron micrographs are displayed in FIG. 32 of cross-sections from films deposited on $Ti_6A_{14}V$, Ti, roughened $Ti_6A_{14}V$, stainless steel, and $Co_{28}Cr_6Mo$ substrates after hydrothermal treatment. All micrographs display an irregular structure with grains emanating from underlying dense, continuous, passivating films. The delamination of the film formed on $Co_{28}Cr_6Mo$ could be an artifact of the polishing process or be related to film-substrate adhesion results reported below (FIG. 32e.). Passive film growth models and results report that the formation of a passivating film occurs through a single process—an initial 2D film is formed followed by 3D growth. Thus, the formation of passivating films on all substrates indicates that the nucleation and growth process is similar on each substrate. Average film thickness values vary from 22+/−8 μm ($Ti_6A_{14}V$) to 12+/−7 μm ($Co_{28}Cr_6Mo$) (FIG. 30). Due to the limited area sampled by a cross-section and the topology of the samples it is not possible to draw conclusions regarding differences in film thickness from one substrate to another. Nonetheless, the formation of a dense, passivating film is important because it has the potential to inhibit the dissolution of toxic metal ions from substrates into the surrounding tissue. The chemical stability of crystalline HA together with the passivation of the substrate surface may make this crystallization process appropriate for anti-corrosion applications as well.

Adhesion

Figure 33:
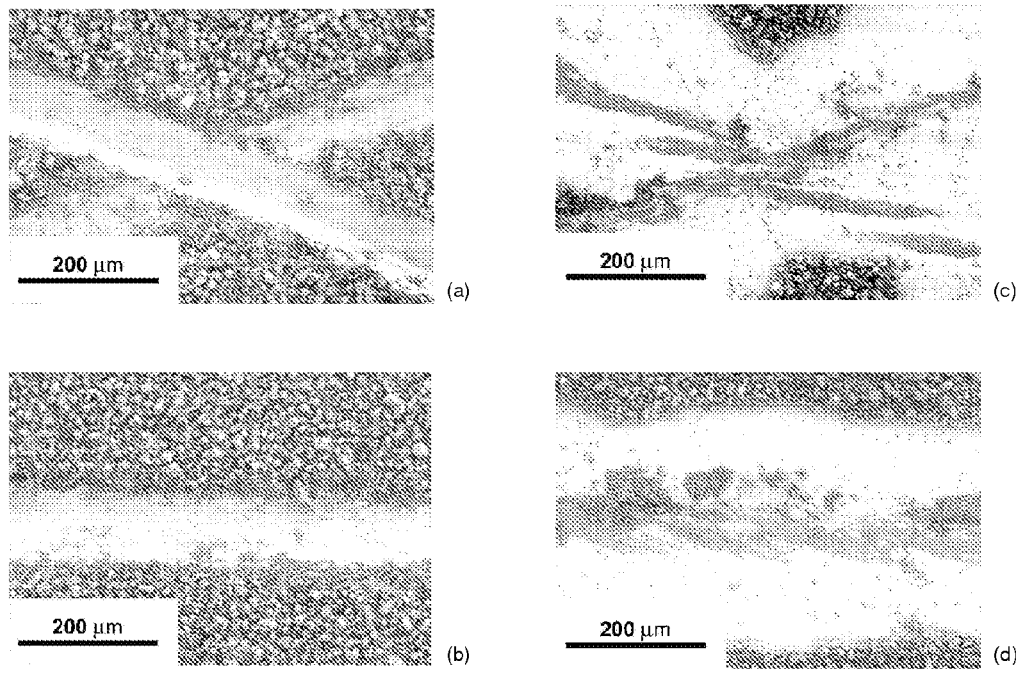
FIG. 33 presents scanning electron micrographs of the surface of representative hydroxyapatite films deposited on substrates by hydrothermal treatment (24 h at 200° C.) after adhesion testing. (a) Roughened $Ti_6A_{14}V$, (b) Roughened $Ti_6A_{14}V$, (c) $Co_{28}Cr_6Mo$ alloy, (c) $Co_{28}Cr_6Mo$ alloy.

Results of adhesion testing are reported in FIGS. 30 and 33. According to the standardized ASTM-D3359-02 adhesion scale of 0-5, the films deposited on $Ti_6A_{14}V$, Ti, and roughened $Ti_6A_{14}V$ substrates scored a 5. Further, scanning electron microscopy analysis of the surface of a representative titanium substrate indicates no peeling or film removal outside the line directly cut with a razor blade. At the intersection of the cross cut, the film forms sharp points indicating strong film adhesion. The films deposited on 316 stainless steel substrates scored an average rating of 4. These films demonstrated variability in adhesion, however. Two of four samples received a rating of 4, one sample received a rating of 5, and one sample received a rating of 3. Films deposited on $Co_{28}Cr_6Mo$ substrates scored an adhesion rating of 3. Scanning electron micrographs of the surface of a representative $Co_{28}Cr_6Mo$ substrate display consistent and jagged film removal on either side of the original cut. Extensive film removal inhibits the formation of sharp points at the intersection of the cross cut. Next generation HA films require high HA film-substrate adhesion to eliminate in vivo coating delamination and its resulting complications, which are known to increase the failure rate of PS-HA coating.

Discussion

TEP hydrolysis kinetics studies revealed that under the chosen reaction conditions free phosphate was not available for HA synthesis until 180° C. at 4 hours synthesis time (FIG. 26). Thus, the use of a delayed release phosphate source provided the opportunity to deposit HA-substrate intermediates prior to TEP hydrolysis, and HA post-hydrolysis in a continuous crystallization process. This is in contrast to processes reported in the literature, which require multiple reaction solutions to form $CaTiO_3$—HA films on titanium substrates that improve film-substrate adhesion. Results from ASTM-D3359-02 tape test A demonstrated that films formed on titanium-based substrates, regardless of alloying components or surface roughness, possessed superior adhesion properties to films formed on 316 stainless steel and $Co_{28}Cr_6Mo$ alloy (FIGS. 29, 30 and 33). Consequently, the explanation for this result is likely the formation of a substrate-HA chemical intermediate on titanium based substrates, $CaTiO_3$. Due to the thickness of the HA film and the limited detection cap-abilities of x-ray diffraction, it is possible an interfacial phase could go undetected by XRD.

Thermodynamic process simulation facilitated the choice of reaction conditions that both were in the region of HA phase stability and regulated the amount of uncomplexed $Ca^{2+}$. Thermodynamic process simulation results reported a two-order-of-magnitude lower $Ca^{2+}$ ion concentration for the hydrothermal system in this study, than the hydrothermal system reported by Fujishiro et al., at their respective HA deposition temperature and pH. (FIG. 25). Based on the results of other hydrothermal HA film crystallization processes, this is a result of the decreased ability of the Ca-$EDTA^{2-}$ complex to dissociate in solutions with increasing pH. By lowering $Ca^{2+}$ concentration it was hypothesized that the reaction conditions used here would favor crystal growth over crystal nucleation.

Growth-dominated film crystallization processes typically result in films with grains that have a characteristic shape and high crystallinity. Results reported above show that uniform morphological films composed of phase pure, high crystallinity, hexagonal faceted HA grains were formed on all substrates. Therefore, it may be concluded that the use of pH together with the Ca-$EDTA^{2-}$ complex regulate the HA hydrothermal crystallization process by reducing the concentration of supersaturating $Ca^{2+}$ ions, enabling the engineering of a growth-controlled crystallization process.

Grain aspect ratio is reportedly a function of $Ca^{2+}$ concentration along with $PO_4^{3-}$ concentration, EDTA/Ca ratio, temperature, and pH. Results reported above demonstrate that the HA grains formed in this study have the largest diameters (8-12 μm) and smallest aspect ratios (1-2) reported in the homogeneous precipitation hydrothermal HA film literature. A comparison of results from the literature cited above demonstrates an interdependence of the crystallization variables noted above, which makes it difficult to definitively conclude why a nearly equiaxed aspect ratio was achieved in this study. Nonetheless, these conditions may be added to the literature to aid further understanding of the relation between grain aspect ratio and synthesis conditions.

Figure 34:
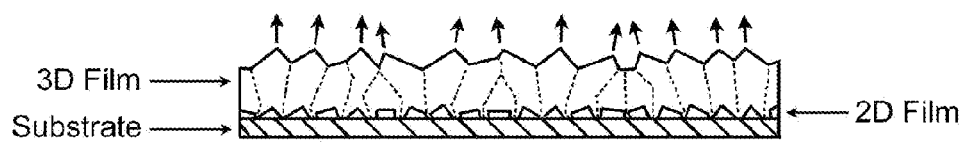
FIG. 34 presents proposed film growth mechanism—competitive polycrystalline film growth—as concluded from cross-sectional SEM and XRD orientation results using square facetted grains with a (111) fast growth direction to explain the process. Initially, a passive 2D film is formed. Subsequently, thickening of the initial 2D film leads to the termination of grains with (010), (100), and (001) texture by crystals with (111) texture. This occurs because the crystals with (111) texture are oriented to have their fast growth direction normal to and in the plane of the film.

The growth mechanism of the films may be inferred from cross-sectional SEM and top-on SEM results (FIGS. 31 and 32). Evaluation of cross sectional samples revealed the formation of dense, continuous, passivating films on all substrates. Based on passive film growth theory and data, film formation occurs through the development of an initial 2D film followed by 3D growth. Evaluation of the surface and the cross-section of films indicate that after the formation of a passive 2D film, hexagonal grains grow independently and vertically, with their c-axis orthogonal to the substrate surface. The topology of the surface confirms this observation. This growth model follows XRD orientation results (FIGS. 28 and 30), which suggest polycrystalline film thickening by competitive growth theory. FIG. 34 graphically illustrates this growth process.

Example 9

Sequenced Deposition of Hydroxyapatite Films Over Titanium Substrate

This example analyzes the potential of utilizing the delayed-release phosphate source TEP to engineer a single hydrothermal crystallization process that deposits $CaTiO_3$ and then HA in a phase sequenced process. The study then investigates the HA film growth mechanism and the development of [0001] crystallographic texture with synthesis time.

Experimental Procedure $Ti_6A_{14}V$ alloy was chosen as the substrate for this study due to its clinical use in load-bearing orthopedic applications. $Ti_6A_{14}V$ was also chosen due to the perfect adhesion value (5, ASTM D3359) reported for HA films previously synthesized by this method on this substrate. $Ti_6A_{14}V$ samples were treated hydrothermally for various times and characterized to investigate the phases deposited by this hydrothermal method, hexagonal grain crystallography, the film growth mechanism, and [0001] crystallographic orientation with synthesis time. Thermodynamic phase diagrams, based on previously reported TEP kinetics studies, were then created to validate/explain experimental results.

Film Synthesis $Ti_6A_{14}V$ samples were treated hydrothermally for various times to investigate the film growth process in terms of previously reported TEP kinetics and autoclave heating dynamics, and time. One-inch diameter rods of $Ti_6A_{14}V$ alloy (ASTM-B348 Grade 5, McMaster Carr, Dayton, N.J.) were cut into discs, 1 in (diameter)×⅛ in (thickness), and used as substrates. All substrates, titanium foil (0.127 mm, 99.7%, Sigma-Aldrich, St. Louis, Mo.) substrate holders, and Teflon® reaction vessel liners (125 mL, model 4731, Parr Instrument, Moline, Ill.) were cleaned with Citronox detergent (Alconox, White Plains, N.Y.), acetone (Fisher Scientific), ethyl alcohol (Pharmco-AAPER, Brookfield, Conn.), and deionized water and dried in a 60° C. oven prior to synthesis.

One set of solution conditions was used for all hydrothermal experiments. Aqueous stock solutions of 0.232 molal calcium nitrate tetrahydrate, $Ca(NO_3)_2 \cdot 4H_2O$ (99.38%, Fisher Scientific), 0.232 molal EDTA, $C_{10}H_{16}N_2O_8$ (99.4%, Fisher Scientific), 0.187 molal TEP, $C_6H_{15}O_4P$ (99.8+%, Sigma Aldrich), and 1.852 molal potassium hydroxide, KOH (89.3%, Fisher Scientific) were prepared as follows: Calcium nitrate tetrahydrate, EDTA, and TEP were mixed together and dissolved in deionized $H_2O$. KOH was dissolved in a second container in deionized $H_2O$. Once dissolved, the KOH solution was placed in a cold-water bath and cooled to room temperature. When cool, the KOH solution was added to the former solution and stirred until visible particulates had dissolved. The stock solution was then filtered (220 nm pore size, Nalgene, Rochester, N.Y.) and stored in a tightly sealed container.

The typical hydrothermal reaction was conducted as follows: The substrate was fixed in the substrate holder and placed inside a 125 ml Teflon®-lined reaction vessel (4731 reactor, Parr Instrument). The substrate holder placed the sample in a position that inhibited the settling of homogeneously formed particles onto the surface by means of gravity. Stock solution, 70 mL, was added to the reaction vessel, which was then sealed. The reactor was then placed in an oven pre-heated to 200° C. for 2, 4, 6, 8, 10, 12, 14, 24, or 46 h. Previously reported autoclave heating dynamics indicate that the reactor was heated from room tempera-ture to 180° C. in 4 h. The reactor was removed from the oven and allowed to cool to room temperature in air. The substrate was removed from the reactor and rinsed for several minutes in running tap water and then in deionized water. The sample was then placed in a 60° C. oven to dry.

Film Characterization

X-ray diffraction (step size=0.005°, 1 step/sec, 45 KV, 40 mA, Ni-filtered CuK$_\alpha$ radiation, parallel beam optics, Philips Hi-Resolution X'PERT X-Ray Diffractometer, PANalytical B.V., Almelo, Netherlands) was used to determine the phases present in the films and the substrate. Field emission scanning electron microscopy (FESEM) (3 kV, DSM 982 Gemini, Carl Zeiss, Oberkochen, Germany) was used to examine the substrate and films. Transmission electron microscopy and EDX samples were prepared one of two ways. Samples, 2 mm×3 mm×500 µm, were cut from a 46 h sample using a diamond saw (Vari/Cut VC-50, Leco Corporation, St. Joseph, Mich.). Samples were mechanically polished to a thickness of less than 50 µm and mounted on a copper grid. A 1 µm wide area of the film-substrate interface was then polished to electron transparency, approximately 100 nm, using a Focused Ion Beam (FIB) (FIB 200, FEI, Hillsboro, Oreg.) and an H-bar technique. The FIB was used to directly cut electron transparent samples from a 6 h sample using a lift-out technique, which were then mounted on copper grids for analysis. Transmission electron microscopy analysis was carried out on a Philips CM20 (200 kV, FEI, Hillsboro, Oreg.) and EDX analysis was carried out on an attached Oxford Instruments Inca energy dispersive X-ray spectrometer (Whitney, Oxon, United Kingdom). For EDX line-scan data the background was calculated at each position on the sample by averaging the background counts at three unique points on the keV spectrum (keV=3, 6.5, 15) that did not overlap with an elemental peak. A standard deviation of the background was then calculated and added to the average background value at each position on the sample. This value was then subtracted from the element counts at each corresponding position on the sample to remove the background.

CaTiO$_3$ film thickness was computed by direct measurement of the thickness of TEM cross-sections at 10 equally spaced points along the length of the micrograph using image analysis software (Adobe Photoshop, Adobe Systems Inc., San Jose, Calif.). Average film thickness and the standard deviation of the mean were calculated using Excel (Microsoft, Redmond, Wash.). The [0001] crystallographic texture of films was evaluated by collecting pole figures of the (0002) HA crystallographic plane using a Philips Hi-Resolution X'PERT X-Ray Diffractometer (PANalytical, Netherlands, 45 KV, 40 mA, Ni-filtered CuK$_\alpha$ radiation, Φ: 0°-360° (substrate rotation), 1°/sec, Ψ: 0°-90° (substrate tilt—relative to the substrate orthogonal), 1°/step) for films deposited for 8, 10, 14, and 24 h as well as for a randomly oriented HA powder sample synthesized in-house. Intensity plots, which represent the population distribution of (0002) planes relative to the substrate surface, are normalized to the most intense psi/phi combination in each plot, varying from 0-1 arbitrary units. To further describe the crystallographic texture, the intensity of phi from 0°-360° was totaled for each degree of psi to give an intensity distribution versus psi. This distribution was then divided by the psi intensity distribution of the randomly oriented powder sample to correct for changes in illumination area with tilt angle and defocus, and to provide data in terms of multiples random distribution (MRD), which is given by the following expression:

$$MRD^{X^0} = \frac{\psi_S^{X^0}}{\psi_{ROPS}^{X^0}} \quad (4)$$

where $\psi_S^{X^0}$ is the x-ray intensity at Ψ=X° for the sample, $\psi_{ROPS}^{X^0}$ is the x-ray intensity at Ψ=X° for the randomly oriented powder sample, and MRD$^{X^0}$ is the multiples random of the sample at Ψ=X°. To determine if hexagonal grains were single crystals, the 6 internal angles of 5 grains were measured from a 24 h synthesis FESEM micrograph using image analysis software (Abobe Photoshop).

Thermodynamic Process Simulation

All thermodynamic diagrams were calculated using OLI thermo-chemical simulation software (OLI Systems, Inc., Morris Plains, N.J.).

Phase stability diagrams for the Ca(NO$_3$)$_2$-EDTA-KOH—H$_2$O system in the pres-ence of titanium substrates at 50 and 180° C. were calculated. These diagrams thermodynamically model the Ca(NO$_3$)$_2$-EDTA-TEP-KOH—H$_2$O—Ti system during reactor heating and prior to full hydrolysis of TEP at 180° C. The software database does not contain TEP because there is no reported thermodynamic data for TEP in the literature. Due to the absence of TEP data, the results from the model do not take into account the products of partial TEP hydrolysis, namely 2H$^+$ and 2C$_2$H$_5$OH. After the creation of phase diagrams, the specific pH/[Ca$^{2+}$] point for the 0.232 molal Ca(NO$_3$)$_2$-0.232 molal EDTA-1.852 molal KOH—H$_2$O—Ti system at 50 and 180° C. was calculated and plotted on each respective diagram.

The phase stability diagram for the Ca(NO$_3$)$_2$-EDTA-H$_3$PO$_4$—KOH—H$_2$O system in the presence of a titanium substrate at 180° C. was also calculated. This diagram models the reaction conditions of the Ca(NO$_3$)$_2$-EDTA-TEP-KOH—H$_2$O— Ti system after full hydrolysis of TEP at 180° C.[29]. Since the thermodynamic software database does not include TEP data, H$_3$PO$_4$ was substituted as a component. The use of this acid allows the model to account for products of TEP hydrolysis, PO$_4^{3-}$ and 3H$^+$, without the explicit use of TEP. The third product of TEP hydrolysis, C$_2$H$_5$OH, was ignored due to its dilute state in the solution, 0.561 molal after full TEP hydrolysis. After the creation of the phase diagram the specific pH/Ca$^{2+}$ combination for the 0.232 molal Ca(NO$_3$)$_2$-0.232 molal EDTA-0.187 molal H$_3$PO$_4$-1.852 m KOH—H$_2$O—Ti chemical system at 180° C. was calculated and plotted on the diagram. The phase stability diagram for the Ca(NO$_3$)$_2$-EDTA-H$_3$PO$_4$— KOH—H$_2$O system in the presence of a titanium substrate at the system's isothermal temperature, 200° C. was presented previously.

Results

Film-Substrate Interface

Figure 35:
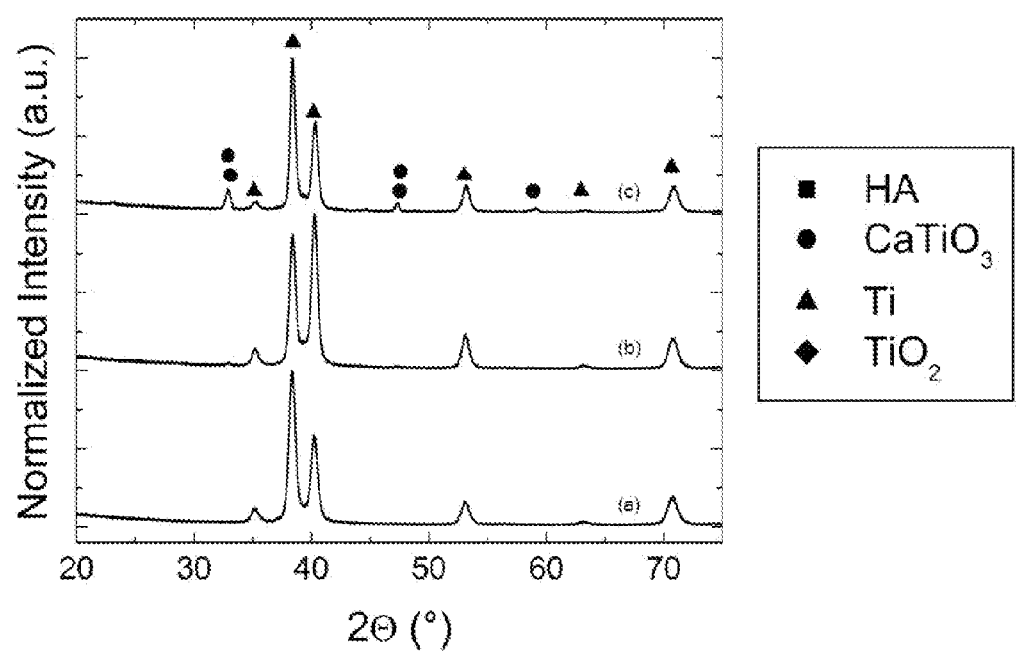
FIG. 35. presents XRD patterns of the $Ti_6A_{14}V$ substrate and films formed on $Ti_6A_{14}V$ substrates after hydrothermal treatment for 0-4 h: (a) 0 h, (b) 2 h, (c) 4 h.
Figure 36:
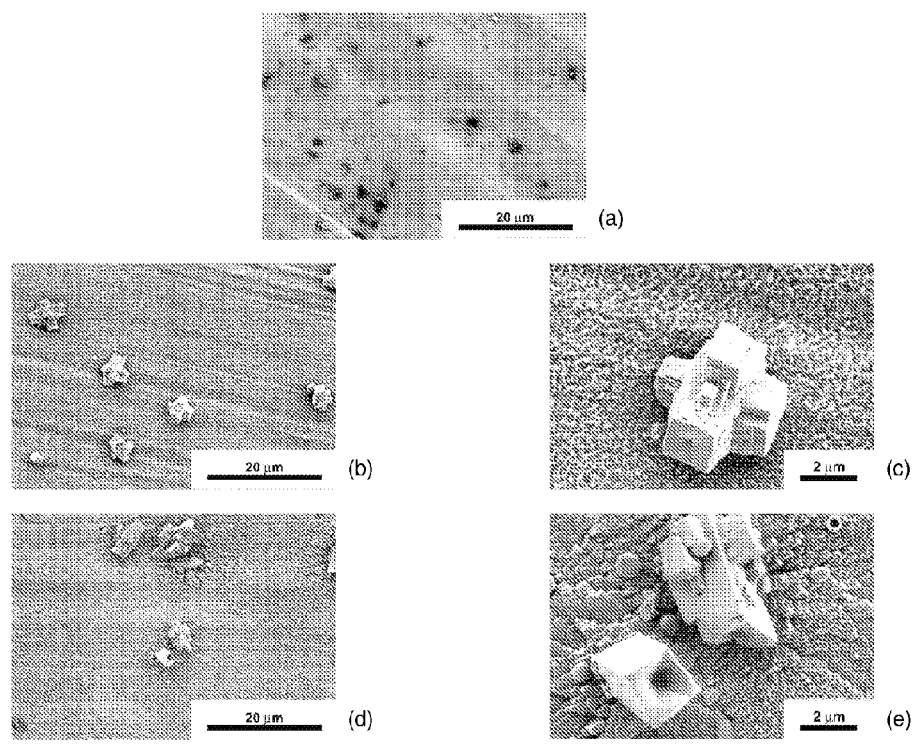
FIG. 36. FESEM micrographs of the $Ti_6A_{14}V$ substrate and films formed on $Ti_6A_{14}V$ substrates after hydrothermal treatment for 0-4 h: (a) 0 h, (b) 2 h, (c) 2 h, (d) 4 h, (e) 4 h.

FIGS. 35 and 36 display time matched X-ray diffraction patterns and scanning electron micrographs of the non-treated Ti$_6$A$_{14}$V substrate and of Ti$_6$A$_{14}$V substrates after 2 and 4 h of hydrothermal treatment, which is prior to full TEP hydrolysis (180° C., 4 h). At 2 h, no phase other than titanium is definitively detected by XRD. FESEM micrographs, however, demonstrate the presence of a nano-pitted film. At 4 h CaTiO$_3$ and titanium are detected by XRD. At this time the substrate surface is covered with a passivating film composed primarily of overlapping inter-grown rectangular plates less than 1 μm in apparent width and thickness, as displayed in FIG. 2. Based on these results it can be concluded that the passivating film is $CaTiO_3$. The film observed at 2 h is likely a thin precursor to the crystalline film observed at 4 h, such as amorphous $CaTiO_3$, that was present in too limited quantity to be definitively detected by XRD.

Figure 37:
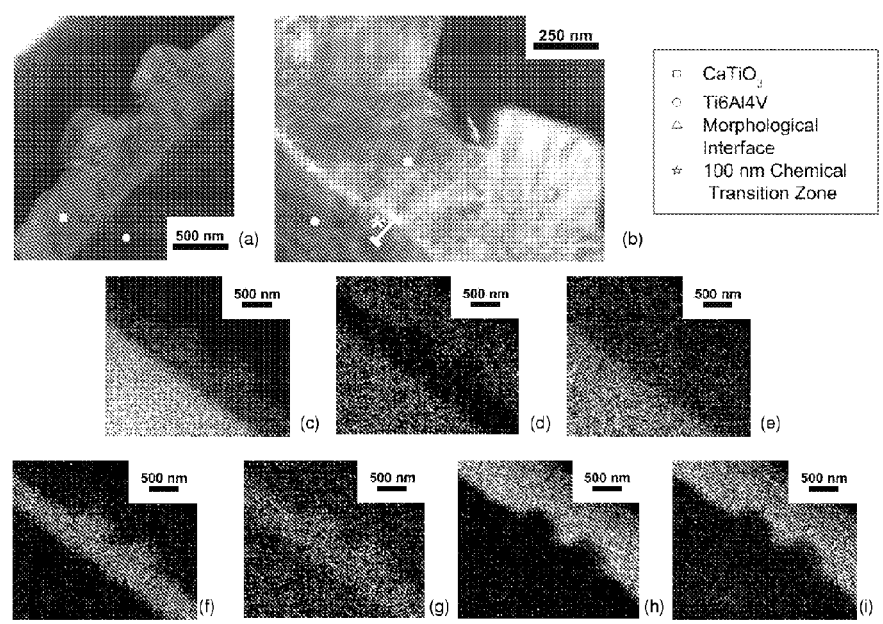
FIG. 37. presents TEM micrographs and EDX maps of a cross-section of a film formed on a $Ti_6A_{14}V$ substrate by hydrothermal synthesis for 6 h: TEM micrographs—(a) & (b), EDX elemental maps—(c) Titanium, (d) Aluminum, (e) Vanadium, (f) Calcium, (g) Oxygen, (h) Phosphorus, (i) Platinum.

Several large rectangular grains are observed by FESEM, in addition to the films formed at 2 and 4 h (FIG. 36). X-ray diffraction phase analysis detection capabilities typically do not enable the detection of phases that compose less than 3-5 wt % of the sample. Therefore, it is possible that these features could represent a second undetected phase such as HA. FIG. 37 displays TEM micrographs and EDX elemental maps of a cross-section of a film at 6 h synthesis time cut from an area containing only the film and rectangular grains observed at 4 h. Energy dispersive X-ray spectroscopy elemental analysis reports that titanium, calcium, and oxygen have overlapping distributions in an area that morphologically corresponds to the film and two protruding rectangular grains. Phosphorus mapping provides no evidence for its presence in either the film or the unidentified rectangular grains. The phosphorus that is observed in the EDX map is a false positive—created due to an overlap in electron energy with platinum that was used to coat the film surface. Thus, it is possible that the passivating film and the rectangular grains at 2 and 4 h are both $CaTiO_3$, and together compose a continuous, phase pure film with an average film thickness of 479+/−27 nm. This finding may also indicate that the small peaks in FIG. 35(b) at ~33 and 47.5° are weak $CaTiO_3$ peaks and not background noise.

Figure 38:
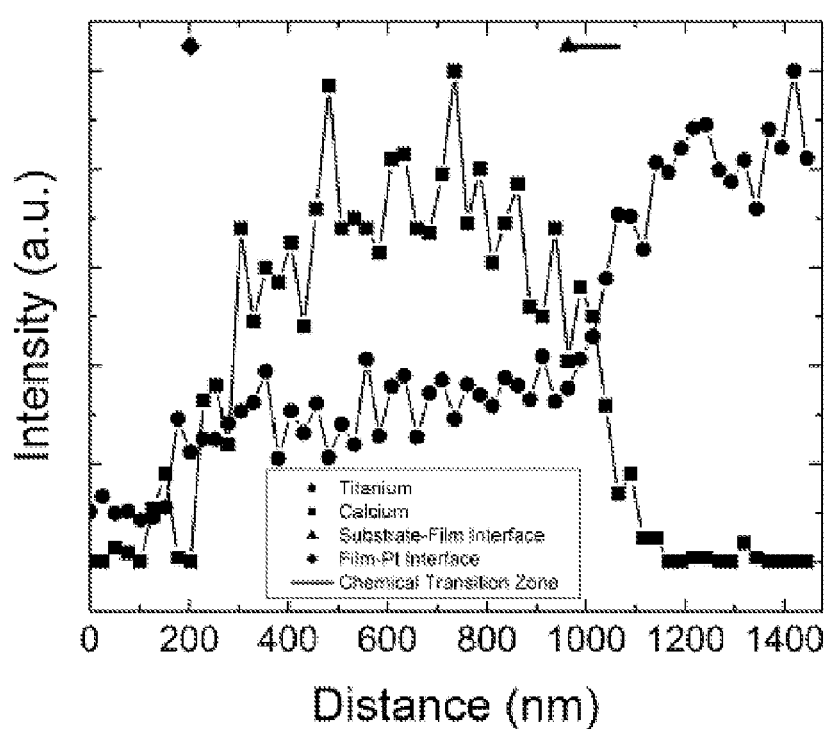
FIG. 38 present the nrmalized EDX line-scan chemical data of a cross-section of a film formed on a $Ti_6A_{14}V$ substrate by hydrothermal synthesis for 6 h. The scan moves from above the deposited film, 0 nm, through the film, and to the bulk substrate, 1400 nm+. Background counts were subtracted at each position.

The structure of the Ti/$CaTiO_3$ interface was analyzed by TEM and EDX line-scan (FIGS. 37 and 38). Transmission electron micrographs display a 20-40 nm bright line that runs the length of the sample. This line was concluded to represent the morphological interface that physically separates the deposited $CaTiO_3$ film from the Ti substrate. Energy dispersive X-ray spectroscopy elemental analysis of the chemical interface indicates that titanium concentration reduces gradually from the bulk Ti substrate on the right hand side of figure (~1000-1500 nm) to the Ti—$CaTiO_3$ morphological interface demarcated by the triangle at the top of the figure (~1000 nm), decreases rapidly across the morphological interface, and reaches a constant value in the $CaTiO_3$ film that corresponding to the left hand side of the figure (~200-1000 nm). From this result, it can be concluded that titanium diffuses from the Ti bulk and through the morphological interface to form $CaTiO_3$. Calcium, concurrently, is found not only in the $CaTiO_3$ film (to the left of the triangle) but also in the morphological interface and in the substrate to a depth of over 100 nm (note the line extending right from the triangle). The physical region of this chemical transition zone is noted with a star in the TEM micrograph in FIG. 37 b. Accordingly, the Ti substrate/$CaTiO_3$ film chemical interface is composed of a layered structure that transitions from the bulk Ti substrate to the $CaTiO_3$ film through a >100 nm chemical transition zone that extends beyond the morphological interface and into the substrate.

Transmission electron micrographs, EDX elemental maps, and EDX elemental line-scan data were obtained from a cross-section near the substrate/film interface of a film synthesized for 46 h. Micrographs, maps, and data were analyzed to determine if subsequent HA film crystallization, after 4 h, altered the $CaTiO_3$ film or the Ti/$CaTiO_3$ interface (data not shown). Transmission electron micrographs display a 90-110 nm bright line that was interpreted to represent the morphological interface that physically separates the deposited $CaTiO_3$ film from the Ti substrate, similar to that seen in the 6 h sample. Energy dispersive X-ray spectroscopy mapping and line scan analysis also reveal results similar to those observed in the 6 h sample, with respect to the chemical interface. Elemental mapping of the film immediately above the substrate demonstrates a continuous several hundred nanometer thick region that contains titanium, calcium, and oxygen, but no phosphorus. Line scan data reveals that titanium diffuses from the bulk Ti substrate and through the morphological interface to form $CaTiO_3$. Line scan data also demonstrate that calcium is present not only in the $CaTiO_3$ film but also in the morphological interface and in the substrate to a depth of over 100 nm. Accordingly, the $CaTiO_3$ film and the Ti/$CaTiO_3$ interfacial structure are maintained at synthesis times up to at least 46 h and are not significantly affected by the subsequent HA film growth process. Thus, it does not appear that a 3-dimensional phase mixture of $CaTiO_3$ and HA is formed at the titanium interface at synthesis times after 4 h.

Hydroxyapatite Film Growth

Figure 39:
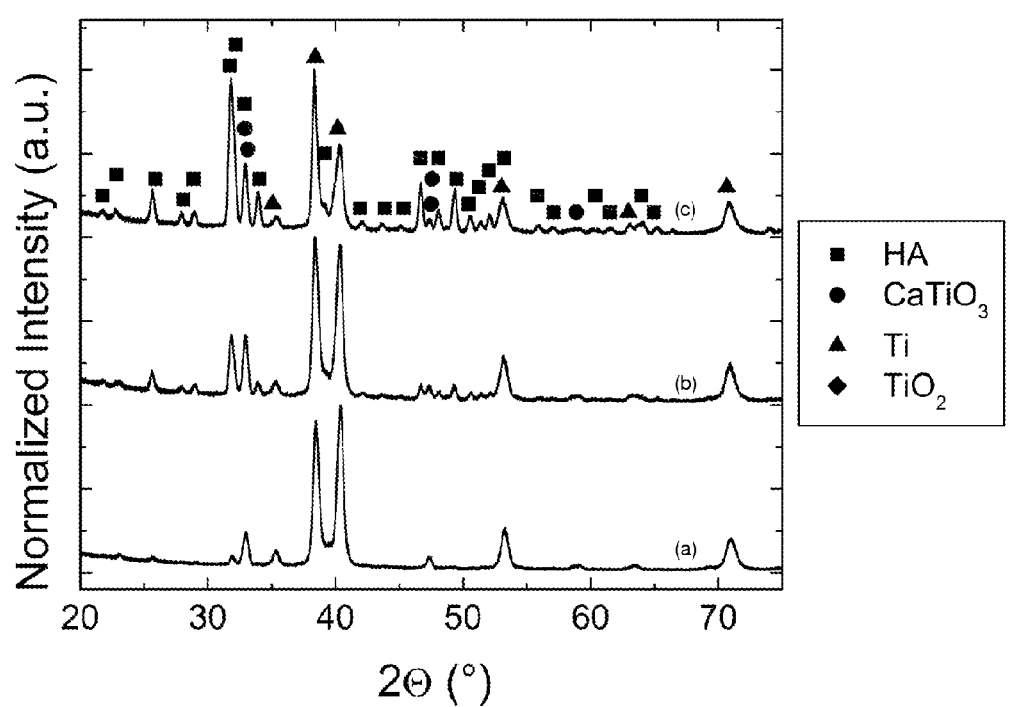
FIG. 39 presents XRD patterns of the $Ti_6A_{14}V$ substrate and films formed on $Ti_6A_{14}V$ substrates after hydrothermal treatment for 6-10 h: (a) 6 h, (b) 8 h, (c) 10 h.
Figure 40:
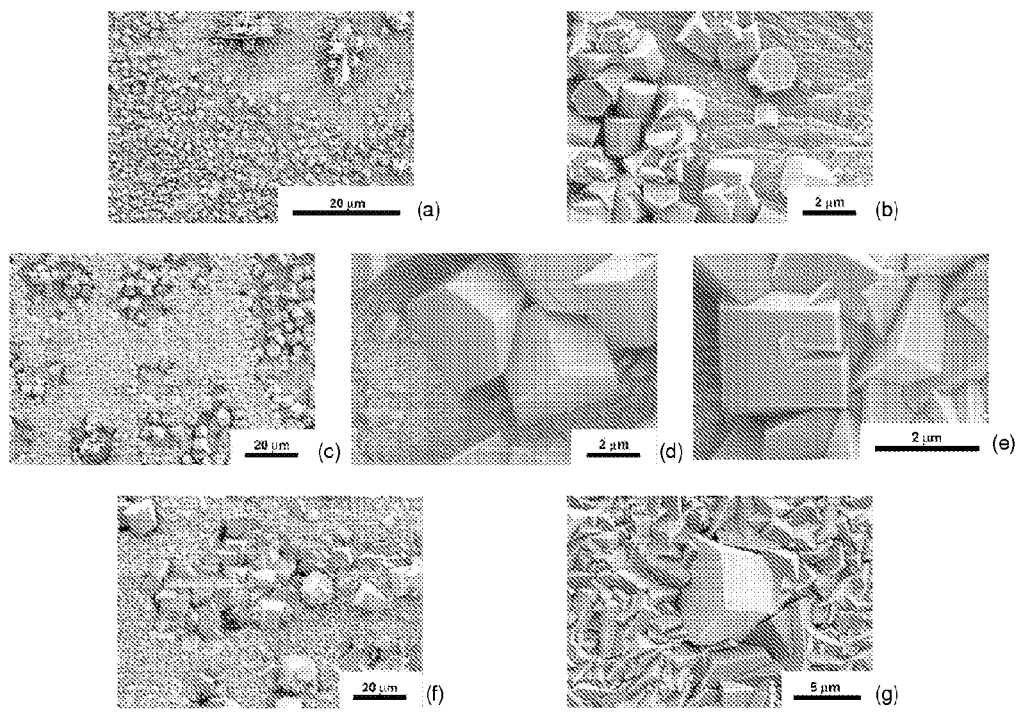
FIG. 40 presents FESEM micrographs of films after hydrothermal treatment for 6-10 h: (a) 6 h, (b) 6 h, (c) 8 h, (d) 8 h, (e) 8 h, (f) 10 h, (g) 10 h.

FIGS. 39 and 40 display corresponding XRD patterns and FESEM micrographs of films deposited on $Ti_6A_{14}V$ substrates for 6, 8, and 10 h by hydrothermal treatment. At 6 h phase analysis demonstrates that the (21 $\bar{3}$ 1) HA peak, at 31.7°, is present along with peaks representing $CaTiO_3$ and Ti. At this time point FESEM demonstrates the formation of hexagonal grains on the underlying $CaTiO_3$ film. Based on this information it may be concluded that the hydrothermal crystallization process presented here deposits hexagonal grains of HA on the $CaTiO_3$ interfacial layer beginning after 4 h synthesis time.

The relationship between hexagonal grain morphology and the pseudo-hexagonal crystallographic unit cell was established by measuring the angles between equivalent faces. Hydroxyapatite is in the 6/m crystal class. One of the typical forms of crystals with this symmetry is the hexagonal prism, which is composed of 6 faces that are parallel to the same principal crystallographic axis. If the hexagonal grains that make up the HA films reported here are single crystals of this form, then Steno's law states that the internal angles between adjacent equivalent faces should be constant. Based on fundamental geometry this angle is 120° for hexagons. The average measurement of the angles between the six equivalent faces of 5 different grains was found to be 120.5°+/−3.6°. Thus, the measured internal angle and the low standard deviation confirm that the hexagons are single crystals of HA. The small observed standard deviation is likely due to limitations in the measurement technique.

As synthesis time increases the XRD peak intensity of HA peaks increases in absolute and relative terms as compared to Ti and $CaTiO_3$ peaks (FIG. 39). Based on XRD fundamentals, peak intensity is a function of the number of diffracting planes. Consequently, the change in HA peak intensity must be related to an increase in coverage and/or thickness of the HA film at reaction times of 6 h or longer. The reduction in the relative peak height of $CaTiO_3$ and Ti is then a result of fewer incident x-rays reaching the $CaTiO_3$ film and Ti substrate and fewer diffracted x-rays escaping the sample as a result of x-ray absorption. FESEM micrographs confirm this conclusion (FIG. 40). From 6 h the originally dispersed hexagonal HA crystals are observed to nucleate and grow until 10 h. At this time a nearly continuous film is formed on top of the initial $CaTiO_3$ film. There is no indication of nucleation and/or growth of the $CaTiO_3$ film or of rectangular $CaTiO_3$ grains during this time. Accordingly, the film formed from 4-10 h is a continuous HA film and not a 3-D $CaTiO_3$/HA phase mixture.

FIG. 40 was examined in further detail to determine the role of nucleation in the formation of the HA film from 4-10 h. At both 6 and 8 h a minority of hexagonal crystals less than 1 μm in size are observed among a majority of larger, micron plus sized, crystals on the surface of the CaTiO$_3$ film. At 10 h no sub-micron grains were observed in the small voids of the nearly continuous film. Accordingly, heterogeneous HA nucleation on CaTiO$_3$ begins sometime after 4 h of hydrothermal treatment and continues either intermittently or continuously until at least 8 h. Concurrently, it may be concluded that the heterogeneous nucleation supersaturation limit for Ca$^{2+}$ and PO$_4^{3-}$, in regard to HA, is crossed soon after 4 h and is maintained continuously or intermittently until at least 8 h.

FIG. 40 was also examined in detail to determine the role of crystal growth in the formation of the HA film from 4-10 h. First, the micrographs reveal that the size of the largest "non-agglomerated" crystals, which are approximately equiaxed, increases from about 1.5-4 μm from 6-8 h. Consequently, the thickness of the incomplete film at 8 h is observed to be approximately 4 μm because the crystals are equiaxed. Second, as crystals grow it is observed that they grow over and around each other, which results in crystals becoming interlocked and the formation of grain clusters with irregular surface morphology. Third, at 8 h the film is continuous with the exception of islands, several microns to tens of microns in diameter, which contain non-interlocked micron-plus sized crystals along with smaller sub-micron crystals. By 10 h, these islands are nearly completely filled in with equiaxed crystals of approximately 10 μm. The film morphology in these areas is observed to be less faceted, however. From these observations it is concluded that the reaction conditions used in this study lead to the formation and growth of equi-axed hexagonal crystals of HA, which grow over and around each other upon impingement. The islands observed at 8 h are potentially a consequence of low nuclei density in some areas at early time points. As a consequence of the low density, crystals are able to grow without impingement from other crystals, leading to the less faceted film morphology observed in some regions at 10 h.

Figure 41:
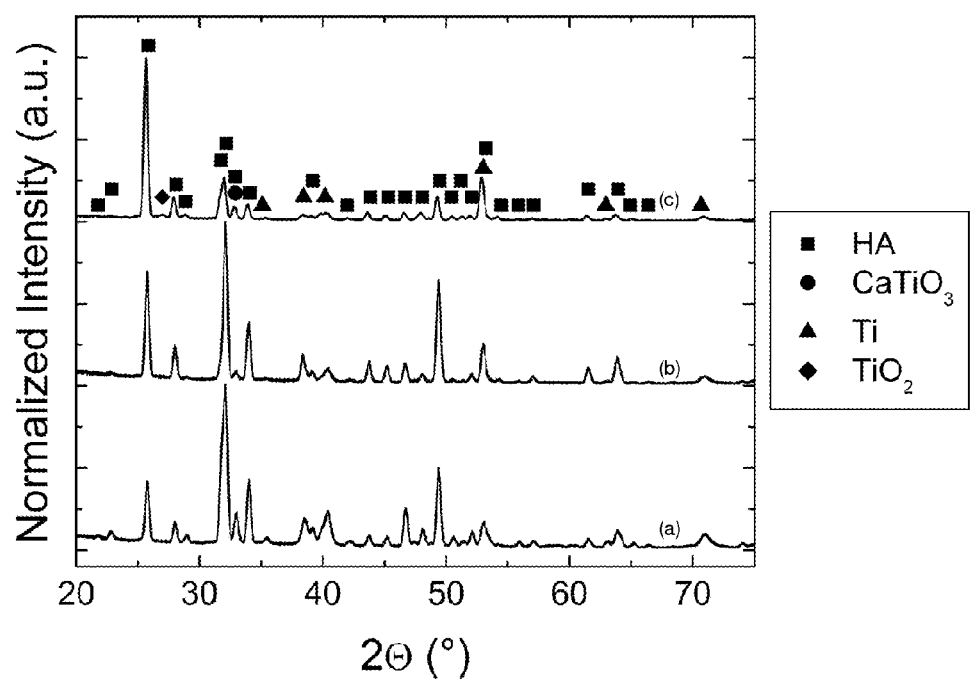
FIG. 41. presents XRD patterns of the $Ti_6A_{14}V$ substrate and films formed on $Ti_6A_{14}V$ substrates after hydrothermal treatment for 12-24 h: (a) 12 h, (b) 14 h, (c) 24 h.

FIG. 41 displays XRD patterns of films deposited on Ti$_6$A$_{14}$V substrates for 12, 14, and 24 h by hydrothermal treatment. As synthesis time increases the XRD peak intensity of HA peaks increases in absolute and relative terms as compared to Ti and CaTiO$_3$ peaks, indicating further film thickening. In addition, the (0002)/(21 $\bar{3}$ 1) XRD peak intensity ratio increases substantially during this time, indicating (0002) crystallographic texturing.

Figure 42:
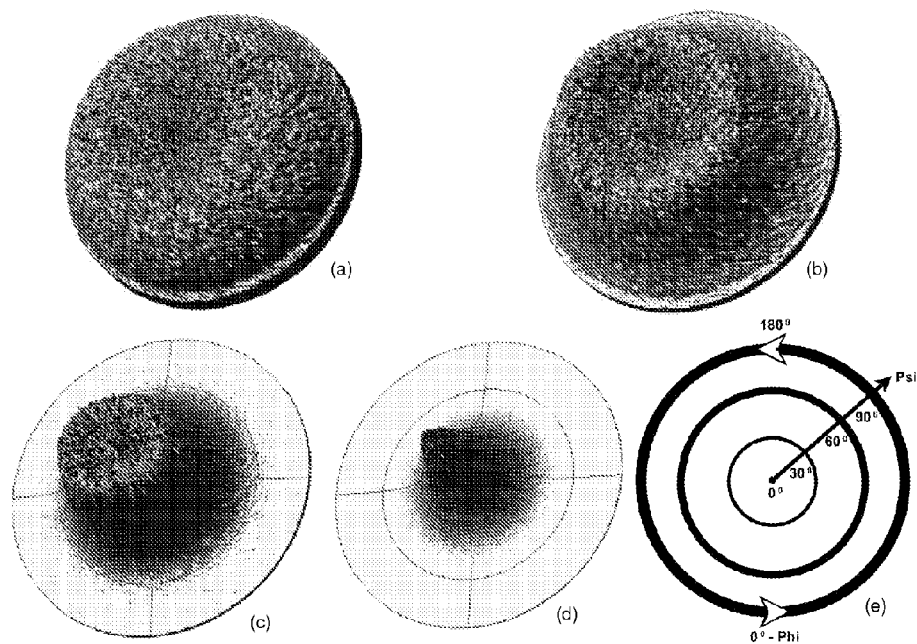
FIG. 42 presents (0002) HA pole figures for films formed on $Ti_6A_{14}V$ substrates after hydrothermal treatment at multiple synthesis time points: (a) 8 h, (b) 10 h, (c) 14 h, (d) 24 h, (e) Legend.
Figure 43:
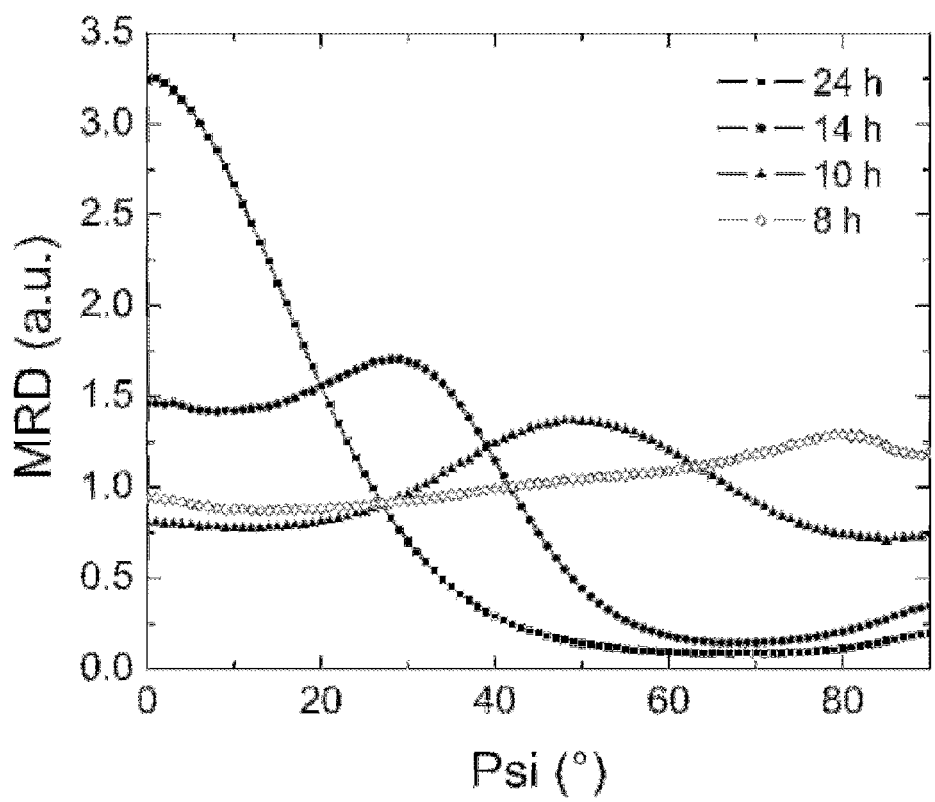
FIG. 43. presents (0002) HA pole figures for films formed on $Ti_6A_{14}V$ substrates after hydrothermal treatment at multiple synthesis time points in terms of MRD.

Pole figures in FIG. 42 report a refinement of the (0002) population distribution relative to the sample surface from 8-24 h. A quantitative examination of the pole figures in terms of MRD is displayed in FIG. 43. The data at 24 h confirm the trend reported in FIG. 42 and demonstrates that the volume fraction of hexagonal HA grains with their (0002) plane parallel to the sample surface (psi=0°) is several multiples greater than expected for a randomly oriented sample. Based on this analysis it is concluded that film thickening after 10 h leads to increasing [0001] crystallographic orientation with synthesis time.

Figure 44:
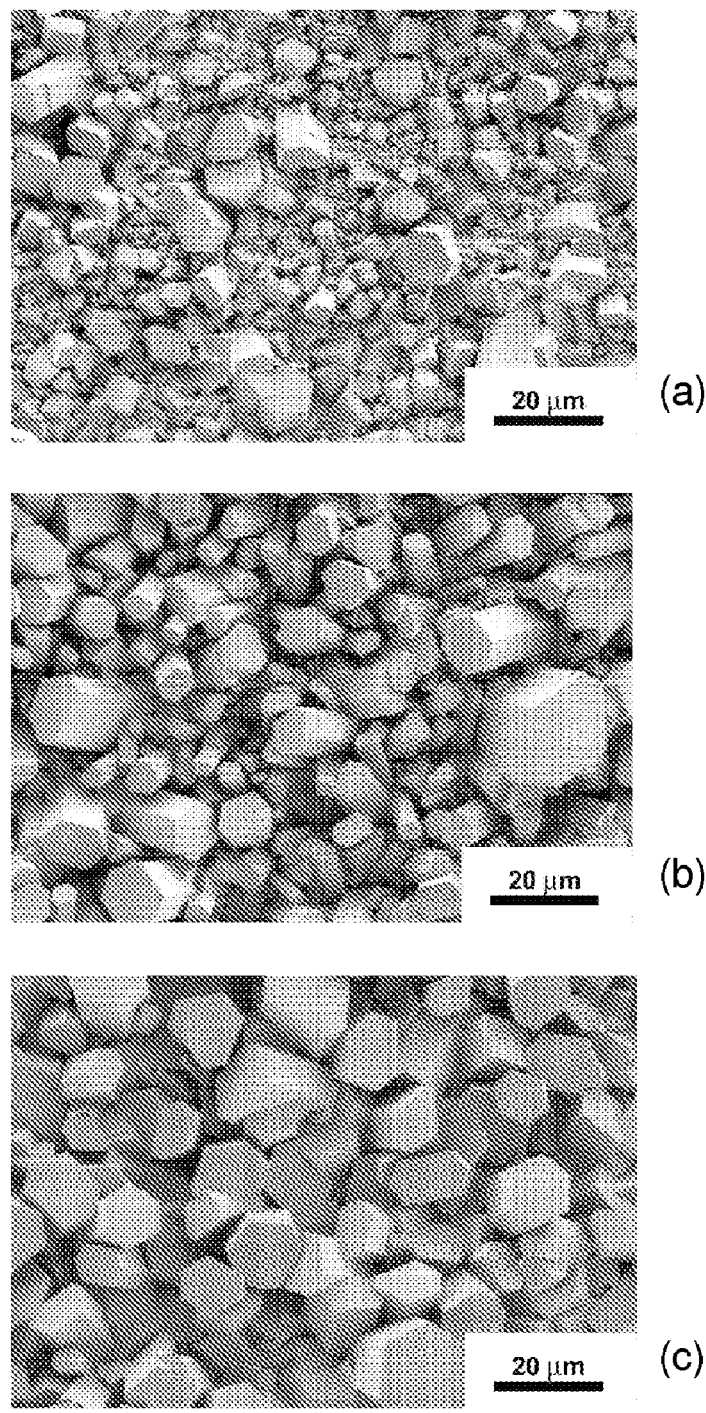
FIG. 44. presents FESEM micrographs of films formed on $Ti_6A_{14}V$ substrates after hydrothermal treatment for 10-24 h: (a) 12 h, (b) 14 h, (c) 24 h.

Time lapsed FESEM micrographs from 12-24 h are displayed in FIG. 44. At 12 h it is observed that a complete and continuous film has formed and that numerous hexagonal rods are protruding from the underlying film. As synthesis time increases from 12-24 h a qualitative increase in hexagonal crystals with their c-axis, [0001] crystallographic direction, perpendicular to the substrate surface is observed. These results agree with XRD/pole figure results, which concluded that film thickening leads to increasing [0001] crystallographic orientation with synthesis time.

Discussion

X-ray diffraction, FESEM, TEM, and EDX results confirmed the formation of a CaTiO$_3$ layer prior to TEP hydrolysis at 4 h synthesis time, validating the first half of the proposed hypothesis (FIGS. 35-38). A mechanism for the formation of CaTiO$_3$ on titanium substrates in high alkaline Ca(EDTA)$^{2-}$ solutions has been proposed previously:

$$Ca(EDTA)^{2-} \leftrightarrow Ca^{2+} + EDTA^{4-} \quad (1)$$

$$Ti + H_2O + 2OH^- \rightarrow TiO_3^{2-} + 2H_2 \quad (2)$$

$$TiO_3^{2-} + Ca^{2+} \rightarrow CaTiO_3 + H_2O \quad (3)$$

However, this mechanism fails to include the well-documented oxide that is present on these titanium substrates. To account for this oxide, authors subjecting titanium substrates to alkali attack prior to biomimetic HA deposition have proposed the following reaction:

$$TiO_2 + OH^- \rightarrow HTiO_3^- \quad (4)$$

This negatively charged species may then react with calcium ions produced from reaction (1) as follows:

$$HTiO_3^- + Ca^{2+} \rightarrow CaTiO_3 + H^+ \quad (5)$$

Figure 45:
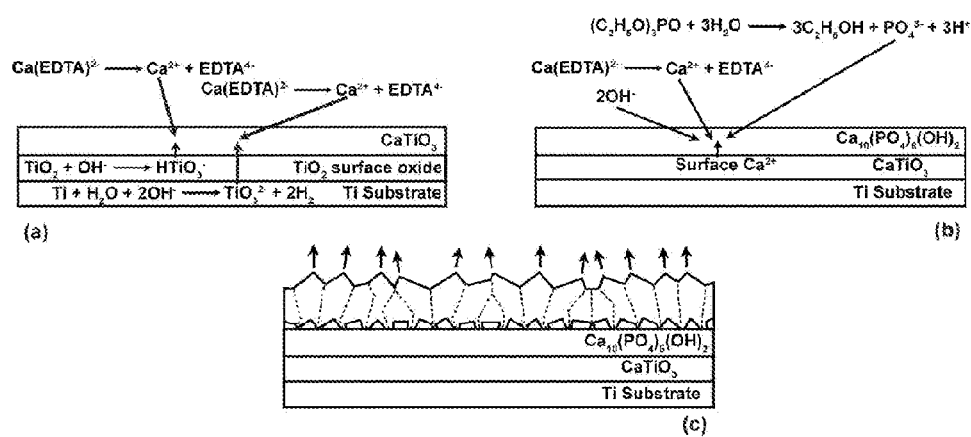
FIG. 45 is a proposed film growth process on $Ti_6A_{14}V$ substrates: (a) $CaTiO_3$ formation below 180° C. and from 0-4 h synthesis time, (b) Continuous HA film formation from 4-10 h synthesis time, (c) Competitive HA film thickening from 10 h on—square facetted grains with a (111) fast growth direction are used to illustrate this process.
Figure 46:
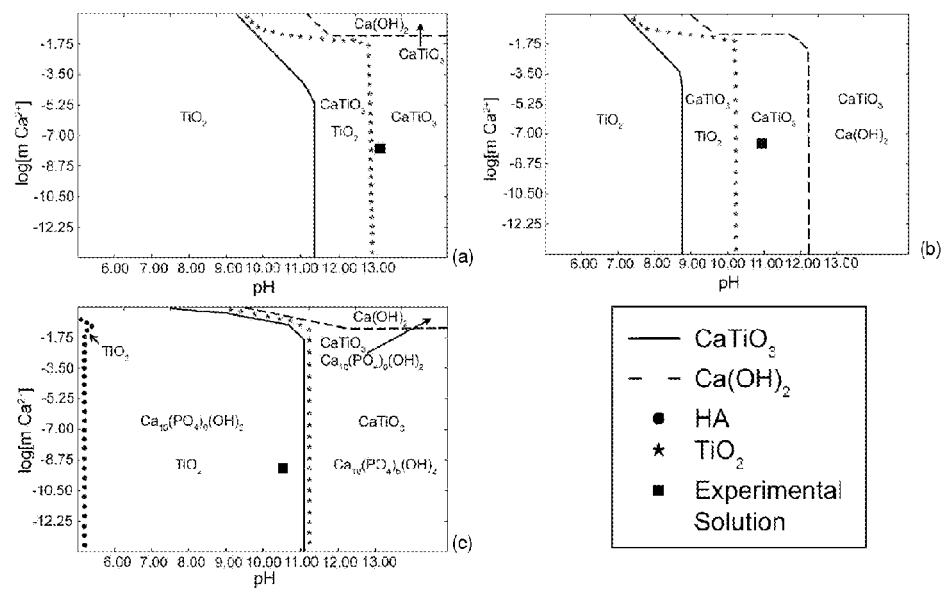
FIG. 46 presents calculated thermo-chemical phase equilibria diagrams for reaction solutions containing (a) 0.232 molal $Ca(NO_3)_2$-0.232 molal EDTA-1.852 molal KOH—$H_2O$ at 50° C. (b) 0.232 molal $Ca(NO_3)_2$-0.232 molal EDTA-1.852 molal KOH—$H_2O$ at 180° C., and (c) 0.232 molal $Ca(NO_3)_2$-0.232 molal EDTA-0.187 molal $H_3PO_4$-1.852 molal KOH—$H_2O$ at 180° C., all in the presence of Titanium.

FIG. 45 graphically displays this crystallization mechanism. The reactions (2) and (4) are believed to occur via a dissolution-precipitation process that creates a negatively charged hydrogel on the titanium substrate surface To determine if there was a thermodynamic basis for the observed result, thermodynamic process simulation software was utilized to create phase stability diagrams based on the reactants and reactant concentrations used in this study. FIGS. 46a and 46b display the computed phase stability diagrams for the Ca(NO$_3$)$_2$-EDTA-TEP-KOH—H$_2$O system in the presence of a titanium substrate at 50 and 180° C., prior to complete TEP hydrolysis. The diagrams illustrate that neither titanium nor its oxide are thermodynamically stable at higher pH. The specific pH/[Ca$^{2+}$] point for the 0.232 molal Ca(NO$_3$)$_2$-0.232 molal EDTA-1.852 molal KOH—H$_2$O—Ti system at both respective temperatures is marked. At both 50 and 180° C. the pH/[Ca$^{2+}$] data point lies in a region where only CaTiO$_3$ is thermodynamically stable. The diagrams demonstrate that the observed formation of the Ti—HA chemical intermediate, CaTiO$_3$, can be explained by fundamental thermodynamics.

X-ray diffraction and FESEM results confirmed that after the hydrolysis of TEP at 4 h and 180° C., hexagonal single crystals of Ca—P phase pure HA are deposited on the initial CaTiO$_3$ film, validating the remainder of the proposed hypothesis (FIGS. 39 and 40). The settling of homogeneously formed crystals onto the film surface is prohibited due to the placement of the sample in the reactor. HA nucleation must therefore occur heterogeneously on the substrate surface. Two mechanisms, electrostatic interactions and epitaxy, have been proposed in the biomimetic literature to explain the heterogeneous nucleation of HA on CaTiO$_3$, which appear applicable to this study. First, Nakamura and coworkers have proposed that heterogeneous HA nucleation occurs on CaTiO$_3$ surfaces in the presence of phosphate ions only after calcium enrichment of the titanate phase and creation of a positive surface charge. In parallel, Hung et al. have demonstrated that hydrothermally crystallized titanium perovskites (ATiO$_3$) have an A-site surface enrichment. Applied here, positively charged calcium ions on the surface of CaTiO$_3$ grains, together with Ca$^{2+}$ ions, PO$_4^{3-}$ ions, and OH$^-$ ions from the solution may take part in heterogeneous nuclei formation in a three-step process, which chemically bonds the HA to CaTiO₃, as demonstrated below: (The italics *Ca²⁺* in equation eight represent calcium on the surface of the CaTiO₃ film)

Ca(EDTA)²⁻ ↔ Ca²⁺ + EDTA⁴⁻     (6)

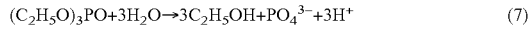

(C₂H₅O)₃PO + 3H₂O → 3C₂H₅OH + PO₄³⁻ + 3H⁺     (7)

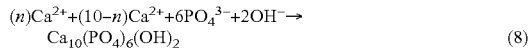

(n)*Ca²⁺* + (10−n)Ca²⁺ + 6PO₄³⁻ + 2OH⁻ → Ca₁₀(PO₄)₆(OH)₂     (8)

FIG. 45b graphically displays this crystallization process. There is a two-dimensional lattice mismatch between the (022) (2X=9.345 Å, 3Y=16.326 Å) plane of CaTiO₃ and the (0001) (X=9.418 Å, Y=16.312 Å) plane of HA of less than 1% and 0.1% respectively, which may enable epitaxial nucleation of HA.

To determine if there was a thermodynamic basis for this result, thermodynamic process simulation software was again utilized. FIG. 46c displays the computed phase stability diagrams for the Ca(NO₃)₂-EDTA-H₃PO₄(TEP)—KOH—H₂O system in the presence of a titanium substrate at 180° C., after complete TEP hydrolysis. The diagram illustrates a wide stability range for HA under these conditions. The specific pH/[Ca²⁺] point for the 0.232 molal Ca(NO₃)₂-0.232 molal EDTA-0.187 molal H₃PO₄-1.852 molal KOH—H₂O system at 180° C. is marked. The diagram demonstrates that the observed formation of Ca—P phase pure HA can be explained by fundamental thermodynamics.

Information regarding HA nucleation in this system may be inferred from FESEM micrographs, which demonstrated an apparent extended nucleation period from 4 h to at least 8 h (FIG. 40). Increasing solution pH has been concluded to slow the dissociation of the Ca-EDTA²⁻ complex. This controlled dissociation enables a solution to maintain a reservoir of Ca²⁺ ions in the form of Ca-EDTA²⁻ that may be released over extended synthesis times. The extended release of Ca²⁺ then enables the heterogeneous supersaturation limit of HA to be breached continuously or intermittently, with respect to Ca²⁺, over an extended period of time. Thus, the inferred extended nucleation period is likely a result of heterogeneously pre-cipitating HA from a homogeneous solution containing Ca-EDTA²⁻ at a high pH (~10.5-11).

Multiple authors have reported that the length and/or aspect ratio of HA crystals formed in solution by non-stirred homogeneous precipitation using EDTA are a function of Ca²⁺ concentration, PO₄³⁻ concentration, EDTA/Ca ratio, temperature, and pH. In general the trend is that crystal length/aspect ratio increases with an increase in each of these variables. Above certain PO₄³⁻ and Ca²⁺ concentrations and temperatures, the trend was reported to reverse, however. Fujishiro et al. attributed the PO₄³⁻ result to changes in HA solubility and the number of nuclei. The Ca²⁺ and temperature result has been attributed to the partial dependence of each variable on the other. Importantly, Fujishiro et al. studying a 0.1 M Ca(NO₃)₂-0.1 M (EDTA)⁴⁻-0.3 M H₃PO₄ system at pH 8 (NH₄OH/HNO₃ adjusted) for 1 h with temperatures that varied from 150 to 225° C. did not see the crystal length/aspect ratio trend reversal that Andes-Verges et al. reports in a 0.05 M Ca(NO₃)₂-0.05 M Na₂(EDTA)-0.03 (NH₄)₂HPO₄³⁻ system at pH 11 (NH₃ adjusted) for 1 h with temperatures that varied from 150° C. to 220° C. Together these results indicates that Ca²⁺ concentration, PO₄³⁻ concentration, EDTA/Ca ratio, temperature, and pH do not strictly dictate crystal length/aspect ratio independently, but rather in concert. Consequently, it can be concluded that the observed formation of low aspect ratio crystals during the formation of the continuous film, 4-10 h, is a function of these reaction conditions.

With the given literature, however, it does not appear possible to specifically determine why low aspect ratio crystals are formed during this period. A comparison to other hydrothermal HA film crystallization processes is not possible either due to a lack of comparable data.

Passive film growth theory and data demonstrate that passive film formation occurs through the formation of a compact primary layer followed by growth of a porous secondary layer. Upon formation of a continuous polycrystalline film (compact primary layer) thickening (secondary layer growth) occurs epitaxially on existing grains and preferentially in certain crystallographic directions resulting in crystallographic texturing that increases with film thickness. Based on this information it was hypothesized that if the films synthesized here follow this growth mechanism, then the [0001] crystallographic orientation of the crystals on the surface of the film may be engineered through the control of synthesis time.

Field emission scanning electron micrograph results confirm the formation of an initial compact primary layer, illustrating that HA crystals nucleate and grow from 4 h until a continuous, passivating, film is formed sometime between 10 and 12 h (FIG. 40, FIG. 44). It has been suggested that a negatively charged surface is required to attract Ca²⁺ ions to a surface and then nucleate and grow HA in a manner that leads to the formation of a continuous passivating uniform film, as presented here. The formation of a continuous CaTiO₃ film prior to HA crystallization, the proposed availability of positively charged calcium ions on the surface of the CaTiO₃, and good CaTiO₃-HA epitaxial matching for HA nuclei formation, however, make this requirement unnecessary for this system. After 10 h, during film thickening (secondary layer growth), XRD, FESEM, and pole figure results demonstrate a refinement of the orientation of HA crystals, such that the population fraction of crystals with their c-axis, or [0001] zone axis, orthogonal to the substrate increases (FIGS. 41-44). This result follows the typical model for polycrystalline film growth, after the formation of a continuous film and confirms the hypothesis offered above. FIG. 11c graphically demonstrates this film growth mechanism. The slow extended release of free Ca²⁺ in this system, which is attributed to the controlled dissociation of the Ca-EDTA²⁺ complex in high pH solutions as discussed above and demonstrated in the extended nucleation period of HA observed in this study and by thermodynamic modeling of free Ca²⁺ concentration in a previous manuscript means that crystal growth is unlikely to occur via Oswald ripening during the synthesis times studied in this manuscript. Thus, the HA film thickening process is concluded to occur by competitive growth in the [0001] HA crystallographic direction. As a result, this growth mechanism provides the opportunity to create HA films composed of hexagonal single crystals with engineered [0001] crystallographic orientation through control of synthesis time. One potential application of controllable crystallographic orientation includes engineering orientation to preferentially increase the surface area of specific HA crystallographic faces presented to the body, such as the bioactive {1 0 1̄ 0} face that is displayed on the 6-equivalent faces of the pseudo-hexagonal lattice.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A method for producing an apatite film on a substrate comprising:
dissolving a source of divalent metal ions, a source of hydroxide ions, and a organophosphate source of reactive phosphate anions in a common solvent to form a solution;
placing a metal substrate into the solution;
heating the solution at a first temperature below the temperature at which said organophosphate undergoes hydrolysis to release reactive phosphate anions but at or above the temperature at which said divalent metal ions react with the substrate in the absence of reactive phosphate anions to form with said metal substrate a layer of a binary oxide of said divalent metal ions and said substrate metal on said metal substrate; and
heating the solution at a second temperature equal to or greater than the temperature at which said organophosphate hydrolysis occurs, so that the organophosphate hydrolyzes to form reactive anions that react with said divalent metal and hydroxide ion sources in solution and with said binary oxide layer to form an apatite layer on said binary oxide layer.

2. The method according to claim 1, wherein the divalent metal ions are chelated.

3. The method according to claim 1, wherein the divalent metal ions are chelated with EDTA.

4. The method according to claim 1, wherein the apatite film passivates the surface of a substrate selected from the group consisting of metals, metal oxides and alloys stable in alkaline media at elevated temperature.

5. The method according to claim 1, wherein the metal comprises titanium.

6. The method according to claim 4, wherein the alloy comprises mild steel, stainless steel, cobalt/chrome, or a titanium alloy.

7. The method according to claim 1, wherein the substrate is selected from the group consisting of porous substrates, wire meshes, wires, rods, bars, ingots, sheets, and free-form shapes.

8. The method according to claim 7, wherein the substrate is selected from the group consisting of titanium, steel, stainless steel, and cobalt-chrome.

9. The method according to claim 1, wherein the divalent metal ions are selected from the group consisting of divalent Group II metals, divalent transition metals, divalent lanthanides and combinations thereof.

10. The method according to claim 1, wherein the divalent metal ions are calcium ions.

11. The method according to claim 10, wherein the source of calcium ions are selected from the group consisting of calcium hydroxide, calcium carbonate, calcium acetate, calcium halides, calcium oxide, calcium nitrate, calcium phosphate and combinations thereof.

12. The method according to claim 1, wherein the organophosphate source comprises one or more compounds having the formula $(RO)_3PO$, wherein each R independently represents hydrogen, an organic hydrocarbon radical or a hydrolysis derivative of organophosphate, provided that at least one R is not a hydrogen.

13. The method according to claim 12, wherein each R group comprises an alkyl group with hydrophilic substituents or a hydrophilic group with an alkyl component.

14. The method according to claim 1, wherein the organophosphate source of reactive phosphates is selected from the group consisting of mono-, di-, and tri-substituted phosphoric acid esters.

15. The method according to claim 1, wherein the organophosphate source comprises one or more compounds selected from the group consisting of tri-ethyl phosphate, tri-methyl phosphate, tri-butyl phosphate and combinations thereof.

16. The method according to claim 1, wherein the reactive anions comprise $PO_4^{3-}$ anions.

17. The method according to claim 1, wherein the hydroxide ion source is selected from the group consisting of ammonium hydroxide, calcium hydroxide, sodium hydroxide, potassium hydroxide, ammonia, calcium oxide, and combinations thereof.

18. The method according to claim 1, wherein the metal substrate is selected from the group consisting of metals, metal alloys and metal oxides.

19. The method according to claim 1, wherein the metal substrate is selected from the group consisting of titanium, titanium alloy, steel, stainless steel, cobalt-chrome, and combinations thereof.

20. The method according to claim 1, wherein the common solvent is selected from the group consisting of water, ethylene glycol, 1,4-butanediol, ethanol, and combinations thereof.

21. The method according to claim 1, wherein the divalent metal anions, organophosphate source and ion concentrations are selected so that the apatite layer is a hydroxyapatite layer.

22. The method according to claim 1, further comprising adding a source of dopant ions to the solution that are selected from the group consisting of divalent dopant ions, trivalent dopant ions and tetravalent dopant ions.

23. An apatite film on a metal substrate prepared by a method according to claim 1.

24. The apatite film of claim 23, characterized in that it is a phase pure hydroxyapatite film.

25. A chromatography column or gas sensor or catalytic support comprising an apatite film on a metal substrate according to claim 23.

26. A method for preparing a metal surface for painting comprising applying an apatite film to the metal surface by a method according to claim 1.

27. A method for protecting a metal surface from corrosion comprising applying an apatite film to the metal surface by a method according to claim 1.

28. A biocompatible hard tissue implant comprising a phase pure hydroxyapatite file on a metal substrate according to claim 24.

* * * * *